US012391759B2

(12) United States Patent
Bosques et al.

(10) Patent No.: US 12,391,759 B2
(45) Date of Patent: Aug. 19, 2025

(54) METHODS RELATED TO ENGINEERED Fc CONSTRUCTS

(71) Applicant: Momenta Pharmaceuticals, Inc., Cambridge, MA (US)

(72) Inventors: Carlos J. Bosques, Arlington, MA (US); James S. Huston, Watertown, MA (US); Jonathan C. Lansing, Reading, MA (US); Leona E. Ling, Winchester, MA (US); James Meador, III, Framingham, MA (US); Daniel Ortiz, Stoneham, MA (US); Laura Rutitzky, Somerville, MA (US); Birgit C. Schultes, Arlington, MA (US)

(73) Assignee: MOMENTA PHARMACEUTICALS, INC., Titusville, NJ (US)

( * ) Notice: Subject to any disclaimer, the term of this patent is extended or adjusted under 35 U.S.C. 154(b) by 1298 days.

(21) Appl. No.: 16/081,829

(22) PCT Filed: Mar. 2, 2017

(86) PCT No.: PCT/US2017/020519
§ 371 (c)(1),
(2) Date: Aug. 31, 2018

(87) PCT Pub. No.: WO2017/151971
PCT Pub. Date: Sep. 8, 2017

(65) Prior Publication Data
US 2022/0153833 A1 May 19, 2022

Related U.S. Application Data

(60) Provisional application No. 62/443,451, filed on Jan. 6, 2017, provisional application No. 62/443,495, filed on Jan. 6, 2017, provisional application No. 62/302,419, filed on Mar. 2, 2016.

(51) Int. Cl.
C07K 16/28 (2006.01)
(52) U.S. Cl.
CPC ........ *C07K 16/283* (2013.01); *C07K 2317/35* (2013.01); *C07K 2317/52* (2013.01)
(58) Field of Classification Search
None
See application file for complete search history.

(56) References Cited

U.S. PATENT DOCUMENTS

| | | | |
|---|---|---|---|
| 4,719,107 A | 1/1988 | Carosella et al. | |
| 5,426,641 A | 6/1995 | Afrashteh et al. | |
| 5,731,168 A | 3/1998 | Carter et al. | |
| 6,737,056 B1 | 5/2004 | Presta | |
| 7,183,076 B2 | 2/2007 | Arathoon et al. | |
| 7,803,769 B2 | 9/2010 | Sullivan et al. | |
| 7,951,917 B1 * | 5/2011 | Arathoon | C07K 16/00 424/134.1 |
| 8,216,805 B2 | 7/2012 | Carter et al. | |
| 8,592,562 B2 | 11/2013 | Kannan et al. | |
| 8,680,237 B2 | 3/2014 | Strome et al. | |
| 9,238,080 B2 | 1/2016 | Nielsen et al. | |
| 10,239,944 B2 | 3/2019 | Bosques et al. | |
| 11,124,573 B2 | 9/2021 | Bosques et al. | |
| 11,155,640 B2 | 10/2021 | Bosques et al. | |
| 11,220,531 B2 | 1/2022 | Bosques et al. | |
| 11,623,964 B2 | 4/2023 | Lansing et al. | |
| 2003/0078385 A1 | 4/2003 | Arathoon | |
| 2006/0074225 A1 | 4/2006 | Block et al. | |
| 2008/0008700 A1 | 1/2008 | Hogarth et al. | |
| 2009/0074839 A1 | 3/2009 | Milankovits | |
| 2009/0304696 A1 | 12/2009 | Lawson et al. | |
| 2010/0093979 A1 | 4/2010 | Lazar | |
| 2010/0143353 A1 | 6/2010 | Mosser et al. | |
| 2010/0216663 A1 | 8/2010 | Kolkman et al. | |
| 2010/0239633 A1 | 9/2010 | Strome | |
| 2010/0286374 A1 | 11/2010 | Kannan | |
| 2011/0262477 A1 | 10/2011 | Cheng et al. | |
| 2011/0311535 A1 | 12/2011 | Dranoff et al. | |
| 2012/0149876 A1 | 6/2012 | Von Kreudenstein et al. | |
| 2012/0219551 A1 | 8/2012 | Johnson et al. | |
| 2012/0244578 A1 | 9/2012 | Kannan et al. | |
| 2013/0156765 A1 | 6/2013 | Block et al. | |
| 2013/0177555 A1 | 7/2013 | Wilkinson et al. | |
| 2014/0024111 A1 | 1/2014 | Kannan et al. | |
| 2014/0051834 A1 | 2/2014 | Hoffman et al. | |
| 2014/0066599 A2 | 3/2014 | Blein et al. | |

(Continued)

FOREIGN PATENT DOCUMENTS

BR PI0620639-5 11/2011
CN 101835802 9/2010

(Continued)

OTHER PUBLICATIONS

Stryer, Biochemistry 4th, WH Freeman, New York. 1995 (Year: 1995).*
Ortiz, Daniel F et al. "Elucidating the interplay between IgG-Fc valency and FcγR activation for the design of immune complex inhibitors." Science translational medicine vol. 8,365 (2016): 365ra158. doi:10.1126/scitranslmed.aaf9418 (Year: 2016).*
Ortiz, Daniel F., et al. "Elucidating the interplay between IgG-Fc valency and FcγR activation for the design of immune complex inhibitors." Science translational medicine 8.365 (2016): 365ra158-365ra158. (Year: 2016).*
Blach-Olszewska, Zofia, and Jerzy Leszek. "Mechanisms of over-activated innate immune system regulation in autoimmune and neurodegenerative disorders." Neuropsychiatric disease and treatment vol. 3,3 (2007): 365-72 (Year: 2007).*

(Continued)

*Primary Examiner* — Zachariah Lucas
*Assistant Examiner* — Lia E Taylor
(74) *Attorney, Agent, or Firm* — Ice Miller LLP

(57) ABSTRACT

The present invention relates to methods of using biologically active Fc domain-containing therapeutic constructs (Fc constructs) to induce immune cell activation of the immune response in a subject, and for example, to treat diseases such as cancers and infections in a subject. Such Fc constructs may include 5 or more Fc domains.

3 Claims, 9 Drawing Sheets
Specification includes a Sequence Listing.

(56) References Cited

U.S. PATENT DOCUMENTS

| | | |
|---|---|---|
| 2014/0105913 A1 | 4/2014 | Strome et al. |
| 2014/0187753 A1 | 7/2014 | Blein et al. |
| 2014/0294817 A1 | 10/2014 | Mosser et al. |
| 2014/0335075 A1 | 11/2014 | Strome et al. |
| 2014/0370012 A1 | 12/2014 | Block et al. |
| 2015/0056185 A1 | 2/2015 | Strome et al. |
| 2015/0184142 A1 | 7/2015 | Hong et al. |
| 2015/0218236 A1 | 8/2015 | Pleass |
| 2016/0229913 A1 | 8/2016 | Bosques et al. |
| 2017/0029505 A1* | 2/2017 | Griffin ................ A61P 1/18 |
| 2019/0225688 A1 | 7/2019 | Bosques et al. |
| 2019/0284305 A1 | 9/2019 | Bosques et al. |
| 2019/0345206 A1 | 11/2019 | Bosques et al. |
| 2021/0221917 A1 | 7/2021 | Lansing et al. |
| 2022/0033499 A1 | 2/2022 | Bosques et al. |
| 2022/0049019 A1 | 2/2022 | Bosques et al. |
| 2022/0267388 A1 | 8/2022 | Bosques et al. |
| 2024/0067757 A1 | 2/2024 | Lansing et al. |

FOREIGN PATENT DOCUMENTS

| | | |
|---|---|---|
| CN | 102549016 | 7/2012 |
| JP | 2007-289200 | 11/2007 |
| JP | 2010-529043 | 8/2010 |
| JP | 2011-508604 | 3/2011 |
| JP | 2011-517456 | 6/2011 |
| JP | 2014-510084 | 4/2014 |
| JP | 2015-527366 | 9/2015 |
| JP | 2015-536317 | 12/2015 |
| JP | 2020-128415 | 8/2020 |
| KR | 2010-0028599 | 3/2010 |
| KR | 2016-0083949 | 7/2016 |
| RU | 2583298 | 5/2016 |
| WO | WO 1997/047732 | 12/1997 |
| WO | WO 01/45746 | 6/2001 |
| WO | WO 2005/077981 | 8/2005 |
| WO | WO 2006/106905 | 10/2006 |
| WO | WO 2008/012543 | 1/2008 |
| WO | WO 2008/131242 | 10/2008 |
| WO | WO 2008/143954 | 11/2008 |
| WO | WO 2008/151088 | 12/2008 |
| WO | WO 2009/089004 | 7/2009 |
| WO | WO 2010/085682 | 7/2010 |
| WO | WO 2010/135521 | 11/2010 |
| WO | WO 2010/135534 | 11/2010 |
| WO | WO 2011/034605 | 3/2011 |
| WO | WO 2011/073692 | 6/2011 |
| WO | WO 2012/006635 | 1/2012 |
| WO | WO 2012/087746 | 6/2012 |
| WO | WO 2012/123949 | 9/2012 |
| WO | WO 2014/031646 | 2/2014 |
| WO | WO 2014/060712 | 4/2014 |
| WO | WO 2015/054958 | 4/2015 |
| WO | WO 2015/095684 | 6/2015 |
| WO | WO 2015/107025 | 7/2015 |
| WO | WO 2015/107026 | 7/2015 |
| WO | WO 2015/132364 | 9/2015 |
| WO | WO 2015/132365 | 9/2015 |
| WO | WO 2015/168643 | 11/2015 |
| WO | WO 2015/184207 | 12/2015 |
| WO | WO 2017/151971 | 9/2017 |
| WO | WO 2017/205434 | 11/2017 |
| WO | WO 2017/205436 | 11/2017 |

OTHER PUBLICATIONS

Dick Jr et al., "C-terminal lysine variants in fully human monoclonal antibodies: investigation of test methods and possible causes," Biotechnology and Bioengineering 2008, 100(6):1132-1143.
European Search Report in Application No. 17760849.4, dated Jan. 11, 2021, 4 pages.
European Office Action in Application No. 17803465.8, dated Jan. 20, 2021, 8 pages.
Kinder et al., "Engineered protease-resistant antibodies with selectable cell-killing functions," J of Biol Chem., Oct. 25, 2013, 288(43):30843-30854.
Armour et al., "Differential binding to human FcγRIIa and FcγRIIb receptors by human IgG wildtype and mutant antibodies," Molecular immunology, 2003, 40(9):585-593.
Chamow et al., "A humanized, bispecific immunoadhesin-antibody that retargets CD3+ effectors to kill HIV-1-infected cells," J. Immunol., 1994, 153:4268-4280 (Abstract Only).
Jain et al., "Fully recombinant IgG2a Fc multimers (stradomers) effectively treat collagen-induced arthritis and prevent idiopathic thrombocytopenia purpura in mice," Arthritis Res Ther., Aug. 20, 2012, 14(4):R192.
Radaev et al., "Recognition of IgG by Fcγ receptor: the role of Fc glycosylation and the binding of peptide inhibitors," Journal of Biological Chemistry, 2001, 276(19):16478-16483.
Rajpal et al., "Introduction: Antibody Structure and Function," Therapeutic Fc-Fusion Proteins, 2014, Chapter 1, 43 pages.
Van Den Bremer et al., "Human IgG is produced in a pro-form that requires clipping of C-terminal lysines for maximal complement activation," mAbs., 2015, 7(4):672-680.
Dall'Acqua et al., "Modulation of the Effector Functions of a Human IgG 1 through Engineering of Its Hinge Region," J. Immunol., 2006, 177:1129-1138.
European Search Report in Application No. 15785583.4, dated Nov. 7, 2017, 12 pages.
International Preliminary Report on Patentability for International Patent Application No. PCT/US2015/028926, mailed Nov. 17, 2016 (12 pages).
International Search Report and Written Opinion for International Application No. PCT/US17/20519, mailed on Aug. 24, 2017, 17 pages.
International Search Report and Written Opinion for International Application No. PCT/US17/34084, mailed on Sep. 14, 2017, 19 pages.
International Search Report and Written Opinion for International Application No. PCT/US17/34087, mailed on Oct. 18, 2017, 20 pages.
International Search Report and Written Opinion for International Application No. PCT/US2015/028926, mailed Oct. 28, 2015 (22 pages).
International Search Report and Written Opinion in International Application No. PCT/US2018/012488, mailed on May 25, 2018, 26 pages.
Kacskovics et al., "Fc receptors in livestock species," Veterinary Immunology and Immunopathology, 2004, 102:351-362.
Lund et al., "Multiple Interactions of Ig with Its Core Oligosaccharide Can Modulate Recognition by Complement and Human Fcγ Receptor I and Influence the Synthesis of Its Oligosaccharide Chains, " The Journal of Immunology, 1996, 157:4963-4969.
Mekhaiel et al., "Polymeric human Fc-fusion proteins with modified effector functions," Scientific Reports, 2011, 1:124 (11 pages).
Mimoto et al., "Novel asymmetrically engineered antibody Fc variant with superior FcγR binding affinity and specificity compared with afucosylated Fc variant," mAbs, 2013, 5:229-236.
Office Action in Israeli Application No. 247442, dated Jun. 3, 2018, 7 pages.
Ortiz et al., "Elucidating the interplay between IgG-Fc valency and FcgR activation for the design of immune complex inhibitors," Science Translational Medicine, 2016, 8:1-13.
Salfeld, "Isotype selection in antibody engineering," Nature Biotech, 2007, 25(12):1369-1372.
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem., 2001, 276:6591-6604.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res., 2007, 67:8882-8890.
Carter "Bispecific human IgG by design," J of Immunol Methods., Feb. 1, 2001, 248(1-2):7-15.

(56) References Cited

OTHER PUBLICATIONS

Crick et al., "A tracer study of the metabolism of p-iodophenyl urethane; the selective localization of radioactive material," Br J Pharmacol Chemother., Mar. 1952, 7(1):142-151.
European Search Report in Application No. 17803463.3, dated Jul. 15, 2020, 11 pages.
European Office Action in Application No. 15785583.4, dated Oct. 12, 2020, 4 pages.
Mestas et al., "Of Mice and Not Men: Differences between Mouse and Human Immunology," J Immunology., 2004, 172(5):2731-2738.
Sowdhamini et al., "Stereochemical modeling of disulfide bridges. Criteria for introduction into proteins by site-directed mutagenesis, " Protein Eng., Nov. 1989, 3(2):95-103.
Anthony, "Identification of a receptor required for the anti-inflammatory activity of IVIG," Proc. Natl. Acad. Sci. U.S.A., Dec. 16, 2008, 105(50):19571-19578.
Atwell et al., "Stable heterodimers from remodeling the domain interface of a homodimer using a phage display library," Biol., Jul. 4, 1997, 270(1):26-35.
Boruchov AM et al., "Activating and inhibitory IgG Fc receptors on human DCs mediate opposing functions," J Clin Invest., Oct. 2005 115(10):2914-2923.
Chu et al., "Inhibition of B cell receptor-mediated activation of primary human B cells by coengagement of CD19 and FcgammaRIIb with Fc-engineered antibodies," Mol Immunol., Sep. 2008, 45(15):3926-3933.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., Apr. 2010, 2(4)3:195-202.
European Search Report in Application No. 17760849.4, dated Sep. 24, 2019, 12 pages.
European Search Report in Application No. 17803465.8, dated Feb. 17, 2020, 12 pages.
Gunadekaran et al., "Enhancing antibody Fc heterodimer formation through electrostatic steering effects: applications to bispecific molecules and monovalent IgG.," J Biol Chem, Jun. 18, 2010, 285(25):19637-19646.
International Preliminary Report on Patentability in International Patent Application No. PCT/US2017/020519, Sep. 4, 2018, 2 pages).
International Preliminary Report on Patentability in International Patent Application No. PCT/US2017/034087, mailed Nov. 27, 2018, 11 pages.
International Preliminary Report on Patentability in International Patent Application No. PCT/US2017/034084, mailed Nov. 27, 2018, 10 pages.
International Preliminary Report on Patentability in International Application No. PCT/US2018/012488, dated Jul. 9, 2019, 10 pages.
Martens et al., "A novel one-armed anti-c-Met antibody inhibits glioblastoma growth in vivo," Clin Cancer Res., 2006, 12(20):6144-6152.
Merchant et al., "An efficient route to human bispecific IgG," Nat Biotechnol, Jul. 1998, 16(7):677-681.
Ridgway et al., "'Knobs-into-holes' engineering of antibody CH3 domains for heavy chain heterodimerization," Protein Eng., Jul. 1996, 9(7):617-612.
Wilson et al., "The structure of an antigenic determinant in a protein," Cell, Jul. 1984, 37(3):767-778.
Zeidler et al., "Simultaneous activation of T cells and accessory cells by a new class of intact bispecific antibody results in efficient tumor cell killing," J Immunol., Aug. 1999, 163(3):1246-1252.
European Search Report in Application No. 18736414.6, dated Nov. 16, 2020, 16 pages.
Grevys et al., "Open Access Fc Engineering of Human IgG1 for Altered Binding to the Neonatal Fc Receptor Affects Fc Effector Functions," The Journal of Immunology, 194(11):5497-5508.
Cai et al., "C-terminal lysine processing of human immunoglobulin G2 heavy chain in vivo," Biotechnol Bioeng., Feb. 2011, 108(2):404-412.
Mimoto et al., "Engineered antibody Fc variant with selectively enhanced FcγRIIb binding over both FcγRIIa(R131) and FcγRIIa(H131)," Protein Eng Des Sel., Oct. 2013, 26(10):589-598.
Nicolaou et al., "Calicheamicin: A Rationally Designed Molecule with Extremely Potent and Selective DNA Cleaving Properties and Apoptosis Inducing Activity," Angew Chem Intl Ed Engl., 1994, 33:183-186.
Extended European Search Report in European Appln. No. 23193565.1, mailed on Feb. 14, 2024, 9 pages.

\* cited by examiner

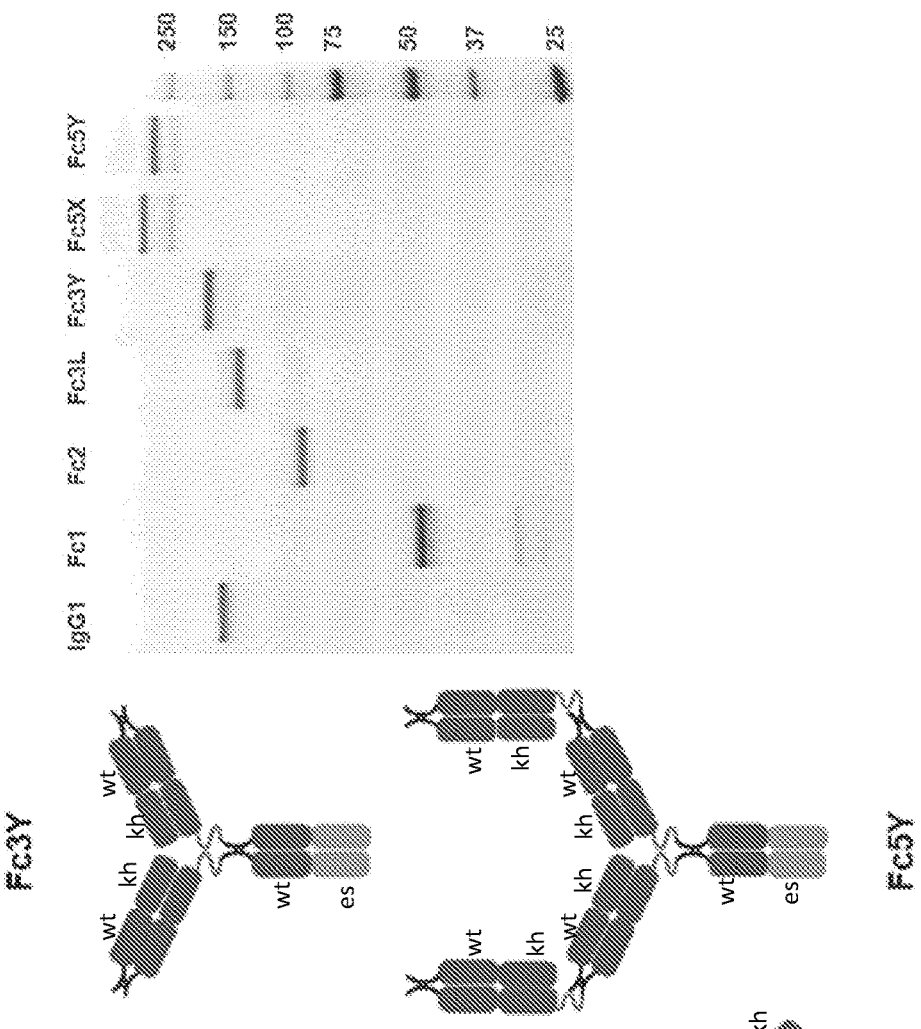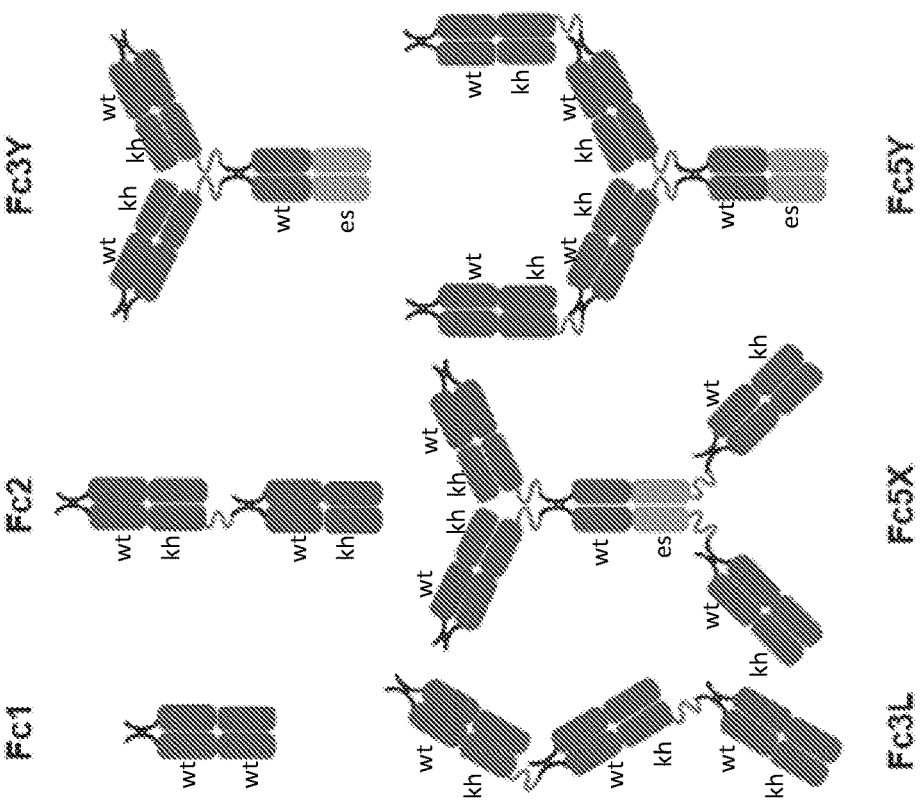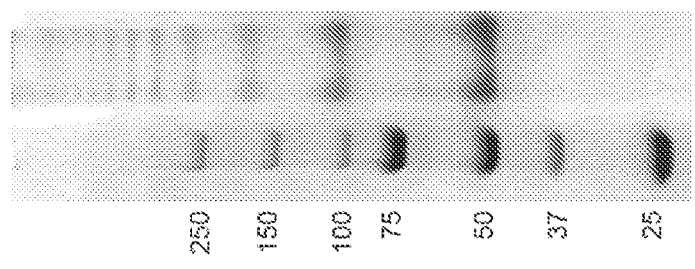
FIG. 1A
FIG. 1B
FIG. 1C

Fc5X

Fc5Y

Fc5Y-invert

METHODS RELATED TO ENGINEERED Fc CONSTRUCTS

CLAIM OF PRIORITY

This application is a national stage application under 35 U.S.C. § 371 of PCT Application No. PCT/US2017/020519, filed Mar. 2, 2017, which claims priority to U.S. Provisional Application No. 62/443,451, filed Jan. 6, 2017, U.S. Provisional Application No. 62/443,495, filed Jan. 6, 2017, and U.S. Provisional Application No. 62/302,419, filed Mar. 2, 2016, of which each of these applications are hereby incorporated by reference in their entirety.

BACKGROUND OF THE INVENTION

Therapeutic proteins that target Fcγ receptors (FcγRs), e.g., Fc-fusion proteins, have become an important drug class.

SUMMARY OF THE INVENTION

The present invention discloses using biologically active Fc domain-containing therapeutic constructs (Fc constructs) to induce immune cell activation of the immune response in a subject. Such Fc constructs may include 5 or more Fc domains, e.g., 5-10 Fc domains (e.g., 5, 6, 7, 8, 9, or 10 Fc domains (e.g., 5 Fc domains)), and have desirable serum half-life, binding affinity, and/or avidity for Fc receptors. These Fc constructs are useful, e.g., to increase phagocytosis of a target cell (i.e., a cancer cell or an infected cell) in a subject and to treat diseases such as cancers and infections in a subject.

In a first aspect, the invention features a method of inducing immune cell activation of the immune response in a subject by administering to the subject a substantially homogenous population of Fc constructs including 5-10 Fc domains.

In some embodiments of the first aspect of the invention, the activation includes Syk phosphorylation in an FcγR-expressing cell. In some embodiments of the first aspect of the invention, the activation includes induction of calcium flux in an FcγR-expressing cell.

In some embodiments of the first aspect of the invention, the activation includes phagocytosis of a target cell in the subject.

In some embodiments of the first aspect of the invention, the FcγR-expressing cell is an immune cell. In some embodiments, the immune cell is a monocyte.

In some embodiments of the first aspect of the invention, the subject has cancer. In some embodiments, the subject has an infection.

In a second aspect, the invention features a method of treating cancer in a subject by administering to the subject a substantially homogenous population of Fc constructs including 5-10 Fc domains.

In some embodiments of the first and second aspects of the invention, the cancer is selected from the group consisting of bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, squamous cell carcinoma, anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor cancer, and soft tissue tumor cancer.

In a third aspect, the invention features a method of treating an infection in a subject by administering to the subject a substantially homogenous population of Fc constructs including 5-10 Fc domains.

In some embodiments of the first and third aspects of the invention, the infection is selected from the group consisting of a bacterial infection, a viral infection, a fungal infection, a helmintic infection, and a protozoal infection.

In a fourth aspect, the invention features a method of protecting against or treating cancer in a subject by administering to the subject (1) an Fc construct including 5-10 Fc domains and (2) an anti-cancer agent.

In some embodiments of the first, second, third, and fourth aspects of the invention, the Fc construct includes 5 Fc domains.

In some embodiments of the first, second, third, and fourth aspects of the invention, the Fc construct includes a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer. A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain. Each of the first and seventh Fc domain monomers includes a complementary dimerization selectivity module that promote dimerization between the first Fc domain monomer and the seventh Fc domain monomer, each of the second and fifth Fc domain monomers includes a complementary dimerization selectivity module that promote dimerization between the second Fc domain monomer and the fifth Fc domain monomer, each of the third and eighth Fc domain monomers includes a complementary dimerization selectivity module that promote dimerization between the third Fc domain monomer and the eighth Fc domain monomer; each of the fourth and ninth Fc domain monomers includes a complementary dimerization selectivity module that promote dimerization between the fourth Fc domain monomer and the ninth Fc domain monomer; and each of the sixth and tenth Fc domain monomers includes a complementary dimerization selectivity module that promote dimerization between the sixth Fc domain monomer and the tenth Fc domain monomer.

In some embodiments of this Fc construct, each of B and B' includes the mutations D399K and K409D, each of A, C, A', and C' includes the mutations S354C, T366W, and E357K, and each of the seventh, eighth, ninth, and tenth Fc domain monomers includes the mutations Y349C, T366S, L368A, Y407V, and K370D.

In some embodiments of this Fc construct, the complementary dimerization selectivity module of the second Fc domain monomer includes a negatively-charged amino acid substitution, the complementary dimerization selectivity module of the fifth Fc domain monomer includes a positively-charged amino acid substitution, the complementary dimerization selectivity module of each of the first, third, fourth, and sixth Fc domain monomers includes an engineered protuberance, and complementary dimerization selectivity module of each of the seventh, eighth, ninth, and tenth Fc domain monomers includes an engineered cavity.

In some embodiments of this Fc construct, the first and second polypeptides have the same amino acid sequence, and the third, fourth, fifth, and sixth polypeptides have the same amino acid sequence.

In some embodiments of this Fc construct, each of the first and second polypeptides has at least 95% sequence identity (e.g., at least 97%, 99%, or 99.5% sequence identity) to the sequence of (SEQ ID NO: 47)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDKLTKNQVSLWCLVK

GFYPSDIAVEWESNGQPENNYKTTPPVLDSDGSFFLYSKLTVDKSRWQQG

NVFSCSVMHEALHNHYTQKSLSLSPGKGGGGGGGGGGGGGGGGGGGDKT

HTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFY

PSDIAVEWESNGQPENNYKTTPPVLKSDGSFFLYSDLTVDKSRWQQGNVF

SCSVMHEALHNHYTQKSLSLSPGKGGGGGGGGGGGGGGGGGGGDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPCRDKLTKNQVSLWCLVKGFYPSD

IAVEWESNGQPENNYKTTPPVLDSDGSFFLYSKLTVDKSRWQQGNVFSCS

VMHEALHNHYTQKSLSLSPG.

In some embodiments of this Fc construct, each of the third, fourth, fifth, and sixth polypeptides has at least 95% sequence identity (e.g., at least 97%, 99%, or 99.5% sequence identity) to the sequence of (SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG.

In some embodiments of the first, second, third, and fourth aspects of the invention, the Fc construct includes a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer. C and C' combine to form a first Fc domain, B and the seventh Fc domain monomer combine to form a second Fc domain, A and the eighth Fc domain monomer combine to form a third Fc domain, B' and the ninth Fc domain monomer combine to form a fourth Fc domain, and A' and the tenth Fc domain monomer combine to form a fifth Fc domain. Each of the third and sixth Fc domain monomers includes complementary dimerization selectivity modules that promote dimerization between the third Fc domain monomer and the sixth Fc domain monomer, each of the second and seventh Fc domain monomers includes complementary dimerization selectivity modules that promote dimerization between the second Fc domain monomer and the seventh Fc domain monomer, each of the first and eighth Fc domain monomers includes complementary dimerization selectivity modules that promote dimerization between the first Fc domain monomer and the eighth Fc domain monomer; each of the fifth and ninth Fc domain monomers includes complementary dimerization selectivity modules that promote dimerization between the fifth Fc domain monomer and the ninth Fc domain monomer; and each of the fourth and tenth Fc domain monomers includes complementary dimerization selectivity modules that promote dimerization between the fourth Fc domain monomer and the tenth Fc domain monomer.

In some embodiments of this Fc construct, each of C and C' includes the mutations D399K and K409D, each of A, B, A', and B' includes the mutations S354C, T366W, and E357K, and each of the seventh, eighth, ninth, and tenth Fc domain monomers includes the mutations Y349C, T366S, L368A, Y407V, and K370D.

In some embodiments of this Fc construct, the complementary dimerization selectivity module of the third Fc domain monomer includes a negatively-charged amino acid substitution, the complementary dimerization selectivity module of the sixth Fc domain monomer includes a positively-charged amino acid substitution, the complementary dimerization selectivity module of each of the first, second, fourth, and fifth Fc domain monomers includes an engineered protuberance, and complementary dimerization selectivity module of each of the seventh, eighth, ninth, and tenth Fc domain monomers includes an engineered cavity.

In some embodiments of this Fc construct, the first and second polypeptides have the same amino acid sequence, and the third, fourth, fifth, and sixth polypeptides have the same amino acid sequence.

In some embodiments of this Fc construct, each of the first and second polypeptides has at least 95% sequence identity (e.g., at least 97%, 99%, or 99.5% sequence identity) to the sequence of (SEQ ID NO: 48)
DKTHTCPPCPAPELLGGPSVFLFPPKPKDTLMISRTPEVTVVVDVSHEDP

EVKFNWYVDGVEVHNAKTKPREEQYNSTYRVVSVLTVLHQDWLNGKEYKC

KVSNKALPAPIEKTISKAKGQPREPQVYTLPPCRDKLTKNQVSLWCLVKG

```
FYPSDIAVEWESNGQPENNYKTTPPVLDSDGSFFLYSKLTVDKSRWQQGN

VFSCSVMHEALHNHYTQKSLSLSPGKGGGGGGGGGGGGGGGGGGGDKTH

TCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVS

NKALPAPIEKTISKAKGQPREPQVYTLPPCRDKLTKNQVSLWCLVKGFYP

SDIAVEWESNGQPENNYKTTPPVLDSDGSFFLYSKLTVDKSRWQQGNVFS

CSVMHEALHNHYTQKSLSLSPGKGGGGGGGGGGGGGGGGGGGGDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLKSDGSFFLYSDLTVDKSRWQQGNVFSCSV

MHEALHNHYTQKSLSLSPG.
```

In some embodiments of this Fc construct, each of the third, fourth, fifth, and sixth polypeptides has at least 95% sequence identity (e.g., at least 97%, 99%, or 99.5% sequence identity) to the sequence of

```
                                        (SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG.
```

In some embodiments of the first, second, third, and fourth aspects of the invention, the Fc construct includes a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer. A and A' combine to form a first Fc domain, B and the seventh Fc domain monomer combine to form a second Fc domain, C and the eighth Fc domain monomer combine to form a third Fc domain, B' and the ninth Fc domain monomer combine to form a fourth Fc domain, and C' and the tenth Fc domain monomer combine to form a fifth Fc domain. Each of the first and fourth Fc domain monomers includes complementary dimerization selectivity modules that promote dimerization between the first Fc domain monomer and the fourth Fc domain monomer, each of the second and seventh Fc domain monomers includes complementary dimerization selectivity modules that promote dimerization between the second Fc domain monomer and the seventh Fc domain monomer, each of the third and eighth Fc domain monomers includes complementary dimerization selectivity modules that promote dimerization between the third Fc domain monomer and the eighth Fc domain monomer; each of the fifth and ninth Fc domain monomers includes complementary dimerization selectivity modules that promote dimerization between the fifth Fc domain monomer and the ninth Fc domain monomer; and each of the sixth and tenth Fc domain monomers includes complementary dimerization selectivity modules that promote dimerization between the sixth Fc domain monomer and the tenth Fc domain monomer.

In some embodiments of this Fc construct, each of A and A' includes the mutations D399K and K409D, each of B, C, B', and C' includes the mutations S354C, T366W, and E357K, and each of the seventh, eighth, ninth, and tenth Fc domain monomers includes the mutations Y349C, T366S, L368A, Y407V, and K370D.

In some embodiments of this Fc construct, the complementary dimerization selectivity module of the first Fc domain monomer includes a negatively-charged amino acid substitution, the complementary dimerization selectivity module of the fourth Fc domain monomer includes a positively-charged amino acid substitution, the complementary dimerization selectivity module of each of the second, third, fifth, and sixth Fc domain monomers includes an engineered protuberance, and complementary dimerization selectivity module of each of the seventh, eighth, ninth, and tenth Fc domain monomers includes an engineered cavity.

In some embodiments of this Fc construct, the first and second polypeptides have the same amino acid sequence, and the third, fourth, fifth, and sixth polypeptides have the same amino acid sequence.

In some embodiments of this Fc construct, each of the first and second polypeptides has at least 95% sequence identity (e.g., at least 97%, 99%, or 99.5% sequence identity) to the sequence of

```
                                        (SEQ ID NO: 49)
DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLKS

DGSFFLYSDLTVDKSRWQQGNVFSCSVMHEALHNHYTQKSLSLSP

GKGGGGGGGGGGGGGGGGGGGDKTHTCPPCPAPELLGGPSVFLF

PPKPKDTLMISRTPEVTCVVVDVSHEDPEVKFNWYVDGVEVHNAK

TKPREEQYNSTYRVVSVLTVLHQDWLNGKEYKCKVSNKALPAPIE

KTISKAKGQPREPQVYTLPPCRDKLTKNQVSLWCLVKGFYPSDIA

VEWESNGQPENNYKTTPPVLDSDGSFFLYSKLTVDKSRWQQGNVF

SCSVMHEALHNHYTQKSLSLSPGKGGGGGGGGGGGGGGGGGGGGD

KTHTCPPCPAPELLGGPSVFLFPPKPKDTLMISRTPEVTCVVVDV

SHEDPEVKFNWYVDGVEVHNAKTKPREEQYNSTYRVVSVLTVLHQ

DWLNGKEYKCKVSNKALPAPIEKTISKAKGQPREPQVYTLPPCRD

KLTKNQVSLWCLVKGFYPSDIAVEWESNGQPENNYKTTPPVLDSD

GSFFLYSKLTVDKSRWQQGNVFSCSVMHEALHNHYTQKSLSLSPG.
```

In some embodiments of this Fc construct, each of the third, fourth, fifth, and sixth polypeptides has at least 95% sequence identity (e.g., at least 97%, 99%, or 99.5% sequence identity) to the sequence of (SEQ ID NO: 42)
DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

DELTKNQVSLSCAVDGFYPSDIAVEWESNGQPENNYKTTPPVLDS

DGSFFLVSKLTVDKSRWQQGNVFSCSVMHEALHNHYTQKSLSLSP

G.

In some embodiments of any one of the three Fc constructs described above that are used in methods of the invention, A consists of an Fc domain monomer. In some embodiments, B consists of an Fc domain monomer. In some embodiments, C consists of an Fc domain monomer. In some embodiments, A' consists of an Fc domain monomer. In some embodiments, B' consists of an Fc domain monomer. In some embodiments, C' consists of an Fc domain monomer. In some embodiments, the third polypeptide consists of an Fc domain monomer. In some embodiments, the fourth polypeptide consists of an Fc domain monomer. In some embodiments, the fifth polypeptide consists of an Fc domain monomer. In some embodiments, the sixth polypeptide consists of an Fc domain monomer.

In some embodiments of any one of the three Fc constructs described above that are used in methods of the invention, the Fc construct further includes an IgG $C_L$ antibody constant domain and an IgG $C_H1$ antibody constant domain, wherein the IgG $C_L$ antibody constant domain is attached to the N-terminus of the IgG $C_H1$ antibody constant domain by way of a linker and the IgG $C_H1$ antibody constant domain is attached to the N-terminus of A by way of a linker. In some embodiments, the Fc construct further includes a second IgG $C_L$ antibody constant domain and a second IgG $C_H1$ antibody constant domain, wherein the second IgG $C_L$ antibody constant domain is attached to the N-terminus of the second IgG $C_H1$ antibody constant domain by way of a linker and the second IgG $C_H1$ antibody constant domain is attached to the N-terminus of A' by way of a linker.

In some embodiments of any one of the three Fc constructs described above that are used in methods of the invention, the first polypeptide and the second polypeptide of the Fc construct have the same amino acid sequence and wherein the third polypeptide, the fourth polypeptide, the fifth polypeptide, and the sixth polypeptide of the Fc construct have the same amino acid sequence.

In some embodiments of any one of the three Fc constructs described above that are used in methods of the invention, one or more of the Fc domain monomers includes an IgG hinge domain, an IgG $C_H2$ antibody constant domain, and an IgG $C_H3$ antibody constant domain. In some embodiments, each of the Fc domain monomers includes an IgG hinge domain, an IgG $C_H2$ antibody constant domain, and an IgG $C_H3$ antibody constant domain. In some embodiments, the IgG is of a subtype selected from the group consisting of IgG1, IgG2a, IgG2b, IgG3, and IgG4. In some embodiments, the IgG is IgG1.

In some embodiments of any one of the three Fc constructs described above that are used in methods of the invention, the linker L1, L2, L1', and/or L2' is a bond. In some embodiments, the linker L1, L2, L1', and/or L2' is a spacer. In some embodiments, the spacer is 3-200 amino acids in length. In some embodiments, the spacer includes the sequence of any one of SEQ ID NOs: 1-24. In some embodiments, the sequence consists of any one of SEQ ID NOs: 1, 2, and 3.

In some embodiments of any one of the three Fc constructs described above that are used in methods of the invention, the linker L1, L2, L1', and/or L2' includes at least 4, at least 8, or at least 12 glycines. In some embodiments, the linker L1, L2, L1', and/or L2' includes 4-30 (e.g., 8-30 or 12-30 glycines). In some embodiments, the linker L1, L2, L1', and/or L2' has the sequence of (SEQ ID NO: 38)
GGGGGGGGGGGGGGGGGGGG.

In some embodiments of any one of the three Fc constructs described above that are used in methods of the invention, the N-terminal Asp in one or more of the first, second, third, fourth, fifth, and sixth polypeptides is mutated to Gln. In some embodiments, the N-terminal Asp in each of the first, second, third, fourth, fifth, and sixth polypeptides is mutated to Gln.

In some embodiments of any one of the three Fc constructs described above that are used in methods of the invention, one or more of the first, second, third, fourth, fifth, and sixth polypeptides lack a C-terminal lysine. In some embodiments, each of the first, second, third, fourth, fifth, and sixth polypeptides lacks a C-terminal lysine.

In some embodiments of any one of the three Fc constructs described above that are used in methods of the invention, at least one of the first, second, third, fourth, fifth, and sixth Fc domains includes an amino acid modification at position I253. In some embodiments, every one of the first, second, third, fourth, fifth, and sixth Fc domains includes an amino acid modification at position I253. In some embodiments, each of the amino acid modifications at position I253 is independently selected from the group consisting of I253A, I253C, I253D, I253E, I253F, I253G, I253H, I253I, I253K, I253L, I253M, I253N, I253P, I253Q, I253R, I253S, I253T, I253V, I253W, and I253Y. In some embodiments, each of the amino acid modifications at position I253 is independently I253A.

In some embodiments of any one of the three Fc constructs described above that are used in methods of the invention, at least one of the first, second, third, fourth, fifth, and sixth Fc domains includes an amino acid modification at position R292. In some embodiments, every one of the first, second, third, fourth, fifth, and sixth Fc domains includes an amino acid modification at position R292. In some embodiments, each of the amino acid modifications at position R292 is independently selected from the group consisting of R292D, R292E, R292L, R292P, R292Q, R292R, R292T, and R292Y. In some embodiments, each of the amino acid modifications at position R292 is independently R292P.

In some embodiments of the first, second, third, and fourth aspects of the invention, the Fc construct further includes an albumin-binding peptide. In some embodiments, the albumin-binding peptide is joined to the N-terminus or C-terminus of one or more of the polypeptides of the Fc construct by way of a linker. In some embodiments, the albumin-binding peptide is joined to the N-terminus or C-terminus of the first polypeptide or the second polypeptide of the Fc construct by way of a linker. In some embodiments, the albumin-binding peptide is joined to the C-terminus of the first polypeptide or the second polypeptide of the Fc construct by way of a linker. In some embodiments, the albumin-binding peptide includes the sequence of SEQ ID NO: 25. In some embodiments, the albumin-binding peptide consists of the sequence of SEQ ID NO: 25.

In some embodiments of the first, second, third, and fourth aspects of the invention, the Fc construct further includes a purification peptide. In some embodiments, the purification peptide is joined to the N-terminus or C-terminus of one or more of the polypeptides of the Fc construct by way of a linker. In some embodiments, the purification peptide is joined to the N-terminus or C-terminus of the first polypeptide or the second polypeptide of the Fc construct by way of a linker. In some embodiments, the purification peptide is joined to the C-terminus of the first polypeptide or the second polypeptide of the Fc construct by way of a linker. In some embodiments, the purification peptide includes a hexa-histidine peptide, a FLAG peptide, a myc peptide, or a hemagglutinin (HA) peptide. In some embodiments, the purification peptide includes the sequence of any one of SEQ ID NOs: 26-29.

In some embodiments of the first and second aspects of the invention, the method further includes administering to the subject an anti-cancer agent.

In some embodiments of the first, second, and fourth aspects of the invention, the Fc construct and the anti-cancer agent are administered substantially simultaneously (as separate entities). In some embodiments of the first, second, and fourth of the invention, the Fc construct and the anti-cancer agent are administered separately. In some embodiments, the Fc construct is administered first, followed by administering of the anti-cancer agent. In some embodiments, the anti-cancer agent is administered first, followed by administering of the Fc construct. In some embodiments, the Fc construct and the anti-cancer agent are administered substantially simultaneously, followed by administering of the Fc construct or the anti-cancer agent alone. In some embodiments, the Fc construct or the anti-cancer agent is administered first, followed by administering of the Fc construct and the anti-cancer agent substantially simultaneously as separate entities.

In some embodiments of the first, second, and fourth aspects of the invention, an anti-cancer agent is joined (i.e., covalently conjugated) to the Fc construct. In some embodiments, the anti-cancer agent is joined to the N-terminus or C-terminus of one or more of the polypeptides by way of a linker. In some embodiments, the anti-cancer agent is joined to the N-terminus or C-terminus of the first polypeptide or the second polypeptide by way of a linker. In some embodiments, the anti-cancer agent is joined to the C-terminus of the first polypeptide or the second polypeptide by way of a linker.

In some embodiments, the anti-cancer agent is a cancer antigen. In some embodiments, the cancer antigen is selected from the group consisting of CD20, prostate-specific antigen (PSA), Her2, CD35, and vascular endothelial growth factor (VEGF). In some embodiments, the anti-cancer agent is selected from the group consisting of an anti-PD-1 antibody, an anti-CTLA-4 (cytotoxic T-lymphocyte-associated protein 4) antibody, and an anti-LAG3 antibody. Examples of other anti-cancer agents are described in detail further herein.

In some embodiments of the first and third aspects of the invention, the method further includes administering to the subject an anti-infective agent.

In some embodiments of the first and third aspects of the invention, the Fc construct and the anti-infective agent are administered substantially simultaneously (as separate entities). In some embodiments of the first and third aspects of the invention, the Fc construct and the anti-infective agent are administered separately. In some embodiments, the Fc construct is administered first, followed by administering of the anti-cancer agent. In some embodiments, the anti-cancer agent is administered first, followed by administering of the Fc construct. In some embodiments of the first and third aspects of the invention, the Fc construct and the anti-infective agent are administered substantially simultaneously (as separate entities), followed by administering of the Fc construct or the anti-infective agent alone. In some embodiments, the Fc construct or the anti-infective agent is administered first, followed by administering of the Fc construct and the anti-infective agent substantially simultaneously (as separate entities).

In some embodiments of the first and third aspects of the invention, an anti-infective agent is joined (i.e., covalently conjugated) to the Fc construct. In some embodiments, the anti-infective agent is joined to the N-terminus or C-terminus of one or more of the polypeptides by way of a linker. In some embodiments, the anti-infective agent is joined to the N-terminus or C-terminus of the first polypeptide or the second polypeptide by way of a linker. In some embodiments, the anti-infective agent is joined to the C-terminus of the first polypeptide or the second polypeptide by way of a linker.

In some embodiments of the first and third aspects of the invention, the anti-infective agent is selected from the group consisting of an anti-bacterial agent, an anti-viral agent, an anti-fungal agent, an anti-helmintic agent, and an anti-protozoal agent. In some embodiments, the anti-infective agent is a microbial antigen (i.e., a microbe component such as a protein or nucleic acid).

In some embodiments, the anti-bacterial agent is selected from the group consisting of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin clavulanate, ampicillin/sulbactam, piperacillin/tazobactam, ticarcillin/clavulanate, bacitracin, colistin, polymyxin b, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (tmp-smx), sulfonamidochrysoidine, demeclocycline, doxycycline, minocycline, oxytetracycline, tetracycline, clofazimine, dapsone, capreomycin, cycloserine, ethambutol(bs), ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.

In some embodiments, the anti-viral agent is selected from the group consisting of abacavir, aciclovir, acyclovir, adefovir, amantadine, amprenavir, ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, fusion inhibitor, ganciclovir, ibacitabine, imunovir, idoxuridine, imiquimod, indinavir, inosine, interferon type iii, interferon type ii, interferon type i, lamivudine, lopinavir, loviride, maraviroc, moroxydine, methisazone, nelfinavir, nevirapine, nexavir, nitazoxanide, novir, oseltamivir, peginterferon alfa-2a, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

In some embodiments, the anti-fungal agent is selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, triazoles, albaconazole, efinaconazole, epoxiconazole, fluconazole, isavuconazole, itraconazole, posaconazole, propiconazole, ravuconazole, terconazole, voriconazole, thiazoles, abafungin, amorolfin, butenafine, naftifine, terbinafine, anidulafungin, caspofungin, micafungin, ciclopirox, flucytosine, griseofulvin, tolnaftate, and undecylenic acid.

In some embodiments, the anti-helmintic agent is selected from the group consisting of albendazole, mebendazole, thiabendazole, fenbendazole, triclabendazole, flubendazole, abamectin, diethylcarbamazine, ivermectin, suramin, pyrantel pamoate, levamisole, niclosamide, oxyclozanide, praziquantel, octadepsipeptide, an aminoacetonitrile derivative, monepantel, spiroindole, derquantel, and pelletierine sulphate.

In some embodiments, the anti-protozoal agent is selected from the group consisting of eflornithine, furazolidone, melarsoprol, metronidazole, ornidazole, paromomycin sulfate, pentamidine, pyrimethamine, tinidazole, and nifursemizone.

In some embodiments, the microbial antigen is a bacterial antigen, a fungal antigen, a parasitic antigen, or a viral antigen. In some embodiments, the bacterial antigen is an encapsulated bacterial antigen. In some embodiments, the antigen is selected from the group consisting of a *Streptococcus* antigen, a *Candida* antigen, a *Cryptococcus* antigen, a *Brucella* antigen, a *Salmonella* antigen, a *Staphylococcus* antigen, a *Porphyromonas* antigen, a *Burkholderia* antigen, a *Bacillus* antigen, a Mycobacteria antigen, a *Shigella* antigen, a *Pseudomonas* antigen, a *Bordetella* antigen, a *Clostridium* antigen, a Norwalk virus antigen, a *Bacillus anthracis* antigen, a *Mycobacterium tuberculosis* antigen, a human immunodeficiency virus (HIV) antigen, a *Chlamydia* antigen, a human Papillomavirus antigen, an influenza virus antigen, a Paramyxovirus antigen, a Herpes virus antigen, a Cytomegalovirus antigen, a Varicella-Zoster virus antigen, an Epstein-Barr virus antigen, a Hepatitis virus antigen, a *Plasmodium* antigen, a *Trichomonas* antigen, a sexually transmitted disease antigen, an aerosol-transmitted disease antigen, a viral encephalitis disease antigen, a protozoal disease antigen, a fungal disease antigen, and a bacterial disease antigen.

In a fifth aspect, the invention provides an immunogenic composition including an anti-cancer agent and an Fc construct described herein, e.g., an Fc construct including 5-10 Fc domains (e.g., 5, 6, 7, 8, 9, or 10 Fc domains). In some embodiments, the Fc construct includes 5 Fc domains. In some embodiments of the fifth aspect of the invention, the anti-cancer agent is a cancer antigen (e.g., CD20, prostate-specific antigen (PSA), Her2, CD35, and vascular endothelial growth factor (VEGF)). In some embodiments, the anti-cancer agent is an anti-PD-1 antibody, an anti-CTLA-4 (cytotoxic T-lymphocyte-associated protein 4) antibody, or an anti-LAG3 antibody. Examples of other anti-cancer agents are described in detail further herein.

In a sixth aspect, the invention provides an immunogenic composition including an anti-infective agent and an Fc construct described herein, e.g., an Fc construct including 5-10 Fc domains (e.g., 5, 6, 7, 8, 9, or 10 Fc domains). In some embodiments, the Fc construct includes 5 Fc domains. In some embodiments of the sixth aspect of the invention, the anti-infective agent is selected from the group consisting of an anti-bacterial agent, an anti-viral agent, an anti-fungal agent, an anti-helmintic agent, and an anti-protozoal agent. In some embodiments, the anti-infective agent is a microbial antigen (i.e., a microbe component such as a protein or nucleic acid). Examples of anti-infective agents are described in detail further herein.

Definitions:

As used herein, the term "Fc domain monomer" refers to a polypeptide chain that includes at least a hinge domain and second and third antibody constant domains ($C_H2$ and $C_H3$) or functional fragments thereof (e.g., fragments that that capable of (i) dimerizing with another Fc domain monomer to form an Fc domain and (ii) binding to an Fc receptor). The Fc domain monomer can be any immunoglobulin antibody isotype, including IgG, IgE, IgM, IgA, or IgD (e.g., IgG). Additionally, the Fc domain monomer can be an IgG subtype (e.g., IgG1, IgG2a, IgG2b, IgG3, or IgG4) (e.g., IgG1). In some embodiments, an Fc domain monomer does not include any portion of an immunoglobulin that is capable of acting as an antigen-recognition region, e.g., a variable domain or a complementarity determining region (CDR). In some embodiments, an Fc domain monomer includes a portion of an immunoglobulin that is capable of acting as an antigen-recognition region, e.g., a variable domain or a CDR. Fc domain monomers can contain as many as ten changes from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art.

As used herein, the term "Fc domain" refers to a dimer of two Fc domain monomers that is capable of binding an Fc receptor. In the wild-type Fc domain, the two Fc domain monomers dimerize by the interaction between the two $C_H3$ antibody constant domains, as well as one or more disulfide bonds that form between the hinge domains of the two dimerizing Fc domain monomers.

In the present invention, the term "Fc construct" refers to associated polypeptide chains forming 2 or more Fc domains as described herein. In some embodiments, an Fc construct includes 5 or more Fc domains, e.g., 5-10 Fc domains (e.g., 5, 6, 7, 8, 9, or 10 Fc domains (e.g., 5 Fc domains)). Fc constructs described herein can include Fc domain monomers that have the same or different sequences. In some embodiments, some Fc domains in an Fc construct (e.g., an Fc construct including 5-10 Fc domains (e.g., 5, 6, 7, 8, 9, or 10 Fc domains (e.g., 5 Fc domains))) include IgG1 or IgG1-derived Fc domain monomers, while other Fc domains in the Fc construct include IgG2 or IgG2-derived Fc domain monomers. In some embodiments, some Fc domains in an Fc construct (e.g., an Fc construct including 5-10 Fc domains (e.g., 5, 6, 7, 8, 9, or 10 Fc domains (e.g., 5 Fc domains))) include a "protuberance-into-cavity pair," while other Fc domains in the Fc construct do not include a "protuberance-into-cavity pair." In some embodiments, the Fc constructs described herein do not include an antigen-recognition region, e.g., a variable domain ($V_H$, $V_L$, a complementarity determining region (CDR), or a hypervariable region (HVR)). In some embodiments, the Fc constructs described herein include an antigen-recognition region, e.g., a variable domain ($V_H$, $V_L$, a CDR, or a HVR). An Fc domain forms the minimum structure that binds to an Fc receptor, e.g., FcγRI, FcγRIIa, FcγRIIb, FcγRIIIa, FcγRIIIb, FcγRIV.

As used herein, the term "antibody constant domain" refers to a polypeptide that corresponds to a constant region domain of an antibody (e.g., a $C_L$ antibody constant domain, a $C_H1$ antibody constant domain, a $C_H2$ antibody constant domain, or a $C_H3$ antibody constant domain).

As used herein, the term "antigen-recognition region" refers to the portions of the light and heavy chains of an antibody that are responsible for the recognition and binding of an antibody to an antigen. The antigen-recognition region includes the variable domains of the light and heavy chains (Fab), which include the complementary determining regions (CDRs, e.g., CDR L1, CDR L2, CDR L3, CDR H1, CDR H2, and CDR H3) and framework regions (FRs).

As used herein, the term "promote" means to encourage and to favor, e.g., to favor the formation of an Fc domain from two Fc domain monomers which have higher binding affinity for each other than for other, distinct Fc domain monomers. As is described herein, two Fc domain monomers that combine to form an Fc domain can have compatible amino acid modifications (e.g., engineered protuberances and engineered cavities) at the interface of their respective $C_H3$ antibody constant domains. The compatible amino acid modifications promote or favor the selective interaction of such Fc domain monomers with each other relative to with other Fc domain monomers which lack such amino acid modifications or with incompatible amino acid modifications. This occurs because, due to the amino acid modifications at the interface of the two interacting $C_H3$ antibody constant domains, the Fc domain monomers to have a higher affinity toward each other than to other Fc domain monomers lacking amino acid modifications.

As used herein, the term "a dimerization selectivity module" refers to a sequence of the Fc domain monomer that facilitates the favored pairing between two Fc domain monomers.

"Complementary" dimerization selectivity modules are dimerization selectivity modules that promote or favor the selective interaction of two Fc domain monomers with each other. Complementary dimerization selectivity modules can have the same or different sequences. Exemplary complementary dimerization selectivity modules are described herein.

As used herein, the term "engineered cavity" refers to the substitution of at least one of the original amino acid residues in the $C_H3$ antibody constant domain with a different amino acid residue having a smaller side chain volume than the original amino acid residue, thus creating a three dimensional cavity in the $C_H3$ antibody constant domain. The term "original amino acid residue" refers to a naturally occurring amino acid residue encoded by the genetic code of a wild-type $C_H3$ antibody constant domain.

As used herein, the term "engineered protuberance" refers to the substitution of at least one of the original amino acid residues in the $C_H3$ antibody constant domain with a different amino acid residue having a larger side chain volume than the original amino acid residue, thus creating a three dimensional protuberance in the $C_H3$ antibody constant domain. The term "original amino acid residues" refers to naturally occurring amino acid residues encoded by the genetic code of a wild-type $C_H3$ antibody constant domain.

As used herein, the term "protuberance-into-cavity pair" describes an Fc domain including two Fc domain monomers, wherein the first Fc domain monomer includes an engineered cavity in its $C_H3$ antibody constant domain, while the second Fc domain monomer includes an engineered protuberance in its $C_H3$ antibody constant domain. In a protuberance-into-cavity pair, the engineered protuberance in the $C_H3$ antibody constant domain of the first Fc domain monomer is positioned such that it interacts with the engineered cavity of the $C_H3$ antibody constant domain of the second Fc domain monomer without significantly perturbing the normal association of the dimer at the inter-$C_H3$ antibody constant domain interface.

As used herein, the term "heterodimeric Fc domain" refers to an Fc domain that is formed by the heterodimerization of two Fc domain monomers, wherein the two Fc domain monomers contain different reverse charge mutations (see, e.g., mutations in Table 2A) and/or protuberance-into-cavity mutations that promote the favorable formation of these two Fc domain monomers. For example, as shown in FIG. 4, in an Fc construct having five Fc domains, a heterodimeric Fc domain may be formed by Fc domain monomers 404 and 418, 408 and 420, 412 and 422, or 416 and 424.

As used herein, the term "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). For example, as shown in FIG. 4, in an Fc construct having five Fc domains, a homodimeric Fc domain may be formed by Fc domain monomers 406 and 414.

As used herein, the term "heterodimerizing selectivity module" refers to engineered protuberances, engineered cavities, and certain reverse charge amino acid substitutions that can be made in the $C_H3$ antibody constant domains of Fc domain monomers in order to promote favorable heterodimerization of two Fc domain monomers that have compatible heterodimerizing selectivity modules. Fc domain monomers containing heterodimerizing selectivity modules may combine to form a heterodimeric Fc domain. Examples of heterodimerizing selectivity modules are shown in Tables 1 and 2A.

As used herein, the term "homodimerizing selectivity module" refers to reverse charge mutations in an Fc domain monomer in at least two positions within the ring of charged residues at the interface between $C_H3$ domains that promote homodimerization of the Fc domain monomer to form a homodimeric Fc domain. Examples of homodimerizing selectivity modules are shown in Tables 2B and 2C.

As used herein, the term "joined" is used to describe the combination or attachment of two or more elements, components, or protein domains, e.g., polypeptides, by means including chemical conjugation, recombinant means, and chemical bonds, e.g., disulfide bonds and amide bonds. For example, two single polypeptides can be joined to form one contiguous protein structure through chemical conjugation, a chemical bond, a peptide linker, or any other means of covalent linkage. In some embodiments, a first Fc domain monomer is joined to a second Fc domain monomer by way of a peptide linker, wherein the N-terminus of the peptide linker is joined to the C-terminus of the first Fc domain monomer through a chemical bond, e.g., a peptide bond, and the C-terminus of the peptide linker is joined to the N-terminus of the second Fc domain monomer through a chemical bond, e.g., a peptide bond. In other embodiments, the N-terminus of an albumin-binding peptide is joined to the C-terminus of the $C_H3$ antibody constant domain of an Fc domain monomer by way of a linker in the same fashion as mentioned above.

As used herein, the term "associated" is used to describe the interaction, e.g., hydrogen bonding, hydrophobic interaction, or ionic interaction, between polypeptides (or sequences within one single polypeptide) such that the polypeptides (or sequences within one single polypeptide) are positioned to form an Fc construct that has at least one Fc domain, e.g., 5-10 Fc domains (e.g., 5, 6, 7, 8, 9, or 10 Fc domains (e.g., 5 Fc domains)). For example, six polypeptides, e.g., two polypeptides each including three Fc domain monomers and four polypeptides each including one Fc domain monomer, associate to form an Fc construct that has five Fc domains (e.g., as shown in FIGS. 4-6). The association between polypeptides does not include covalent interactions.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 3-200 amino acid, 3-150 amino acid, or 3-100 amino acid sequence) occurring between two polypeptides or polypeptide domains to provide space and/or flexibility between the two polypeptides or polypeptide domains. An amino acid spacer is part of the primary sequence of a polypeptide (e.g., joined to the spaced polypeptides or polypeptide domains via the polypeptide backbone). The formation of disulfide bonds, e.g., between two hinge regions or two Fc domain monomers that form an Fc domain, is not considered a linker.

As used herein, the term "glycine spacer" refers to a linker containing only glycines that joins two Fc domain monomers in tandem series. A glycine spacer may contain at least 4, 8, or 12 glycines (e.g., 4-30, 8-30, 12-30, 12-50, 12-100, or 12-200 glycines; e.g., 12-30, 4, 5, 6, 7, 8, 9, 10, 11, 12, 13, 14, 15, 16, 17, 18, 19, 20, 21, 22, 23, 24, 25, 26, 27, 28, 29, or 30 glycines). In some embodiments, a glycine spacer has the sequence of GGGGGGGGGGGGGGG (SEQ ID NO: 37) or GGGGGGGGGGGGGGGGGGG (SEQ ID NO: 38).

As used herein, a "substantially homogenous population" of polypeptides of an Fc construct is one in which at least 50% of the polypeptides or Fc constructs in a composition (e.g., a cell culture medium or a pharmaceutical composition) have the same number of Fc domains and the same Fc domain structure, as determined by non-reducing SDS gel electrophoresis or size exclusion chromatography. A substantially homogenous population of polypeptides of an Fc construct may be obtained prior to purification, or after Protein A or Protein G purification, or after any Fab or Fc-specific affinity chromatography only. In various embodiments, at least 55%, 60%, 65%, 70%, 75%, 80%, or 85% of the polypeptides or Fc constructs in the composition have the same number of Fc domains. In other embodiments, up to 85%, 90%, 92%, 95%, 97%, 98%, 99%, or 99.5% of the polypeptides or Fc constructs in the composition have the same number of Fc domains.

As used herein, the term "multimer" refers to a molecule including at least two associated Fc constructs described herein.

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments, an albumin-binding peptide is fused to the N- or C-terminus of an Fc domain monomer to increase the serum half-life of the Fc construct. An albumin-binding peptide can be fused, either directly or through a linker, to the N- or C-terminus of an Fc domain monomer.

As used herein, the term "purification peptide" refers to a peptide of any length that can be used for purification, isolation, or identification of a polypeptide. A purification peptide may be joined to a polypeptide to aid in purifying the polypeptide and/or isolating the polypeptide from, e.g., a cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct are described in detail further herein.

As used herein, the term "anti-cancer agent" refers to a natural or synthetic agent that is used in combination with an Fc construct described herein in methods of treating and/or protecting against cancer. The phrase "in combination with an Fc construct" refers to (1) the anti-cancer agent is administered in addition to the Fc construct as a separate entity, i.e., the anti-cancer agent is administered together (i.e., substantially simultaneously) with the Fc construct or administered separately from the Fc construct, or (2) the anti-cancer agent is joined (i.e., covalently conjugated) to the Fc construct and the conjugate is administered in methods of treating and/or protecting against cancer. In some embodiments, an anti-cancer agent may be capable of preventing and/or treating cancer, or inhibiting the development and/or progression of cancer. In some embodiments, an anti-cancer agent may inhibit the proliferation of and/or kill cancer cells. An anti-cancer agent may be a small molecule, a peptide, or a protein.

In some embodiments, an anti-cancer agent may be a cancer antigen. A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. A cancer antigen may be associated with a specific type of tumor, such as a lymphoma, a carcinoma, a sarcoma, or a melanoma. A cancer antigen may elicit immune responses against the cancer (i.e., a cancerous tumor).

In some embodiments, an anti-cancer agent may be a fragment antigen-binding (Fab) domain, which recognizes and binds to antigens (e.g., cancer antigens).

In some embodiments, an anti-cancer agent may be an agent that inhibits and/or down regulates the activity of a protein that prevents immune cell activation. Examples of proteins that prevent immune cell activation include, but are not limited to, PD-1 (programmed cell death protein 1), CTLA-4 (cytotoxic T-lymphocyte-associated protein 4), and LAG3 (lymphocyte-activation protein 3). An anti-cancer agent may be an anti-PD-1 antibody, an anti-CTLA-4 antibody, or an anti-LAG3 antibody.

Other examples of anti-cancer agents are described in detailed further herein.

As used herein, the term "anti-infective agent" refers to an agent that is used in combination with an Fc construct described herein in methods of treating an infection. The phrase "in combination with an Fc construct" refers to (1) the anti-infective agent is administered in addition to the Fc construct as a separate entity, i.e., the anti-infective agent is administered together (i.e., substantially simultaneously) with the Fc construct or administered separately from the Fc construct, or (2) the anti-infective agent is joined (i.e., covalently conjugated) to the Fc construct and the conjugate is administered in methods of treating an infection. In some embodiments, an anti-infective agent prevents and/or treats an infection in a subject. An anti-infective agent may be an agent that prevents the entrance of a pathogen (e.g., bacteria, viruses, fungi, helminths, protozoans) into a subject's cells, tissues, or organs, inhibits the growth of a pathogen in a subject's cells, tissues, or organs, and/or kills a pathogen that is inside a subject's cells, tissues, or organs. In some embodiments, an anti-infective agent may be an anti-bacterial agent, an anti-viral agent, an anti-fungal agent, an anti-helmintic agent, and an anti-protozoal agent. In some embodiments, the anti-infective agent is a microbial antigen (i.e., a microbe component such as a protein or nucleic acid). Examples of anti-infective agents are described in detail further herein.

As used herein, the phrase "immune cell activation of the immune response" refers to an immune response that is induced or activated by the binding of an immune complex or an Fc construct to an Fcγ receptor (FcγR) (e.g., an activating FcγR, e.g., FcγRI, FcγRIIa, FcγRIIc, FcγRIIIa, or FcγRIIIb) on a cell (e.g., an immune cell (e.g., a monocyte)). An immune complex is an antigen-antibody complex formed from the binding of an antibody to an antigen. An immune complex often has multiple Fc domains, which aggregate FcγRs and inhibit or activate cellular processes that play critical roles in inflammation, infection, and other diseases. An Fc construct having 5 or more Fc domains, e.g., 5-10 Fc domains (e.g., 5, 6, 7, 8, 9, or 10 Fc domains (e.g., 5 Fc domains)), is able to bind to FcγRs and induce activating FcγR (e.g., FcγRI, FcγRIIa, FcγRIIc, FcγRIIIa, or FcγRIIIb) signaling on immune cells (e.g., a monocyte). As described in detail further herein, measurement of certain downstream signaling events, such as kinase phosphorylation (e.g., Syk phosphorylation) and calcium influx in the FcγR-expressing cell may be used to detect immune cell activation of an immune response caused by the binding of an immune complex or an Fc construct. For example, immune cell activation of the immune response is induced if the level of kinase phosphorylation (e.g., Syk phosphorylation) or the level of calcium influx of the cell is at least 5 fold, e.g., 5-100 fold (e.g., 5-100, 10-95, 15-90, 20-85, 25-80, 30-75, 35-70, 40-65, 45-60, or 50-55 fold; e.g., 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, or 100-fold) higher than the level of kinase phosphorylation (e.g., Syk phosphorylation) or calcium influx of the cell without any activation by the immune complex or the Fc construct.

As used herein, the term "phagocytosis" refers a form of endocytosis, in which a cell, often a phagocyte (e.g., a monocyte), engulfs another cell, a particle, or a pathogen (e.g., a microbe or a parasite) to form a phagosome. In the immune system, phagocytosis is a major mechanism used to remove diseased cells (e.g., a cancer cell, an infected cell, or a dead cell), pathogens, and cell debris. A cell that is targeted to be phagocytosed by another cell (e.g., a phagocyte (e.g., a monocyte)) is referred to as a target cell. For example, an immune cell (e.g., a monocyte) activated by the binding of an Fc construct (e.g., an Fc construct having 5-10 Fc domains) to the FcγRs (e.g., FcγRI, FcγRIIa, FcγRIIc, FcγRIIIa, or FcγRIIIb) on the immune cell may phagocytose a target cell, which may be a cancer cell or an infected cell in a subject.

As used herein, "increase" or "increasing" phagocytosis of a target cell refers to the increase in phagocytosis induced by the binding of an Fc construct, e.g., an Fc constructing having 5-10 Fc domains (e.g., 5, 6, 7, 8, 9, or 10 Fc domains (e.g., 5 Fc domains)), to FcγRs (e.g., FcγRI, FcγRIIa, FcγRIIc, FcγRIIIa, or FcγRIIIb) on an immune cell (e.g., a monocyte) relative the level of phagocytosis that occur without Fc construct induction. For example, phagocytosis of a target cell is increased if the level of phagocytosis is at least 10%, e.g., 10-100% (e.g., 10-100%, 15-95%, 20-90%, 25-85%, 30-80%, 35-75%, 40-70%, 45-65%, or 50-60%; e.g., 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) higher than the level of phagocytosis that occur without Fc construct induction.

As used herein, the term "protecting against cancer" refers to preventing a subject from developing cancer or decreasing the risk that a subject may develop cancer. Prophylactic drugs used in methods of protecting against cancer in a subject are often administered to the subject prior to any detection of cancer. In some embodiments of methods of protecting against cancer, a subject (e.g., a subject at risk of developing cancer) may be administered prophylactic drugs (e.g., an Fc construct comprising 5-10 Fc domains (e.g., 5 Fc domains) and an anti-cancer agent) to prevent the cancer development or decrease the risk of cancer development.

As used herein, the term "treating cancer" refers to a therapeutic treatment of cancer in a subject. A therapeutic treatment slows the progression of cancer, improves the subject's outcome, and/or eliminates the cancer.

As used herein, the term "treating an infection" refers to a therapeutic treatment of an infection in a subject. A therapeutic treatment slows the progression of the infection, improves the subject's outcome, and/or eliminates the infection.

As used herein, the term "infection" refers to the invasion of a subject's cells, tissues, and/or organs by a pathogen, such as bacteria, viruses, fungi, helminths, protozoans, arthropods, and other microbes, parasites, and worms. In some embodiments, the pathogen may grow, multiply, and/or produce toxins in the subject's cells, tissues, and/or organs. In some embodiments, the subject may develop a negative reaction (i.e., an allergic reaction or an immune response) to the pathogen. Examples of infections include, but are not limited to, a bacterial infection, a viral infection, a fungal infection, a helmintic infection, and a protozoal infection.

As used herein, the term "bacterial infection" refers to an infection caused by one or more bacteria. Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus Enteritis (e.g., Enteritis *salmonella*), and bacteria in the genus *Salmonella* (e.g., *Salmonella typhi*).

As used herein, the term "viral infection" refers to an infection caused by one or more viruses. Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitus C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus).

As used herein, the term "fungal infection" refers to an infection caused one or more fungi. Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticillioides, F. oxysporum*).

As used herein, the term "helmintic infection" refers to an infection caused by one or more helminths. Examples of helminths include, but are not limited to, tapeworms (cestodes), roundworms (nematodes), flukes (trematodes), and monogeneans.

As used herein, the term "protozoal infection" refers to an infection caused by one or more protozoans. Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand. A single polynucleotide is translated into a single polypeptide.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "amino acid positions" refers to the position numbers of amino acids in a protein or protein domain. The amino acid positions for antibody or Fc constructs are numbered using the Kabat numbering system (Kabat et al., *Sequences of Proteins of Immunological Interest*, National Institutes of Health, Bethesda, Md., ed 5, 1991).

As used herein, the term "amino acid modification" refers to an alteration of an Fc domain polypeptide sequence that, compared with a reference sequence (e.g., a wild-type, unmutated, or unmodified Fc sequence) may have an effect on the pharmacokinetics (PK) and/or pharmacodynamics (PD) properties, serum half-life, effector functions (e.g., cell lysis (e.g., antibody-dependent cell-mediated toxicity (ADCC) and/or complement dependent cytotoxicity activity (CDC)), phagocytosis (e.g., antibody dependent cellular phagocytosis (ADCP) and/or complement-dependent cellular cytotoxicity (CDCC)), immune activation, and T-cell activation), affinity for Fc receptors (e.g., Fc-gamma receptors (FcγR) (e.g., FcγRI (CD64), FcγRIIa (CD32), FcγRIIb (CD32), FcγRIIIa (CD16a), and/or FcγRIIIb (CD16b)), Fc-alpha receptors (FcaR), Fc-epsilon receptors (FcγR), and/or to the neonatal Fc receptor (FcRn)), affinity for proteins involved in the compliment cascade (e.g., C1q), post-translational modifications (e.g., glycosylation, sialylation), aggregation properties (e.g., the ability to form dimers (e.g., homo- and/or heterodimers) and/or multimers), and the biophysical properties (e.g., alters the interaction between $C_H1$ and $C_L$, alters stability, and/or alters sensitivity to temperature and/or pH) of an Fc construct, and may promote improved efficacy of treatment of immunological and inflammatory diseases, cancers, and infections. An amino acid modification includes amino acid substitutions, deletions, and/or insertions. In some embodiments, an amino acid modification is the modification of a single amino acid. In other embodiment, the amino acid modification is the modification of multiple (e.g., more than one) amino acids. The amino acid modification may comprise a combination of amino acid substitutions, deletions, and/or insertions. Included in the description of amino acid modifications, are genetic (i.e., DNA and RNA) alterations such as point mutations (e.g., the exchange of a single nucleotide for another), insertions and deletions (e.g., the addition and/or removal of one or more nucleotides) of the nucleotide sequence that codes for an Fc polypeptide.

In certain embodiments, at least one (e.g., one, two, three, four, or five) Fc domain within an Fc construct includes an amino acid modification. In some instances the at least one Fc domain includes one or more (e.g., two, three, four, five, six, seven, eight, nine, ten, or twenty or more) amino acid modifications.

As used herein, the term "percent (%) identity" refers to the percentage of amino acid (or nucleic acid) residues of a candidate sequence, e.g., the sequence of an Fc domain monomer in an Fc construct described herein, that are identical to the amino acid (or nucleic acid) residues of a reference sequence, e.g., the sequence of a wild-type Fc domain monomer, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

100×(fraction of A/B)

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity (e.g., 50% to 100%, 60% to 100%, 70% to 100%, 80% to 100%, 90% to 100%, 92% to 100%, 95% to 100%, 97% to 100%, 99% to 100%, or 99.5% to 100% identity), across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

In some embodiments, an Fc domain monomer in an Fc construct described herein (e.g., an Fc construct having at least one Fc domain, e.g., 5-10 Fc domains (e.g., 5, 6, 7, 8, 9, or 10 Fc domains (e.g., 5 Fc domains))) may have a sequence that is at least 95% identical (e.g., at least 97%, 99%, or 99.5% identical) to the sequence of a wild-type Fc domain monomer (e.g., SEQ ID NO: 39). In some embodiments, an Fc domain monomer in an Fc construct described herein (e.g., an Fc construct having at least one Fc domain, e.g., 5-10 Fc domains (e.g., 5, 6, 7, 8, 9, or 10 Fc domains (e.g., 5 Fc domains))) may have a sequence that is at least 95% identical (e.g., at least 97%, 99%, or 99.5% identical) to the sequence of any one of SEQ ID NOs: 40-46. In certain embodiments, an Fc domain monomer in the Fc construct may have a sequence that is at least 95% identical (e.g., at least 97%, 99%, or 99.5% identical) to the sequence of SEQ ID NO: 42, 45, and 46.

In some embodiments, a polypeptide having three Fc domain monomers in an Fc construct described herein (e.g., polypeptides 402 and 410 in FIG. 4; polypeptides 502 and 510 in FIG. 5; polypeptides 602 and 610 in FIG. 6) may have a sequence that is at least 95% identical (e.g., at least 97%, 99%, or 99.5% identical) to the sequence of any one of SEQ ID NOs: 47-49. In certain embodiments, a polypeptide having three Fc domain monomers in an Fc construct described herein may have a sequence that is at least 95% identical (e.g., at least 97%, 99%, or 99.5% identical) to the sequence of SEQ ID NO: 47.

In some embodiments, a spacer between two Fc domain monomers may have a sequence that is at least 75% identical (e.g., 75%, 77%, 79%, 81%, 83%, 85%, 87%, 89%, 91%, 93%, 95%, 97%, 99%, 99.5%, or 100% identical) to the sequence of any one of SEQ ID NOs: 1-24 and 30-38 (e.g., SEQ ID NOs: 38) described further herein.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding desired domains which can then combine to form a desired Fc construct.

As used herein, "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the term "pharmaceutical composition" refers to a medicinal or pharmaceutical formulation that contains at least one active ingredient as well as one or more excipients and diluents to enable the active ingredient suitable for the method of administration. The pharmaceutical composition of the present invention includes pharmaceutically acceptable components that are compatible with the Fc construct. The pharmaceutical composition is typically in aqueous form for intravenous or subcutaneous administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present invention, the pharmaceutically acceptable carrier must provide adequate pharmaceutical stability to the Fc construct. The nature of the carrier differs with the mode of administration. For example, for oral administration, a solid carrier is preferred; for intravenous administration, an aqueous solution carrier (e.g., WFI, and/or a buffered solution) is generally used.

DESCRIPTION OF THE DRAWINGS

FIG. 1A shows a non-reducing SDS-PAGE analysis of protein products generated from uncontrolled multimerization of tandem weight Fc domains.

FIG. 1B shows schematic representations of Fc constructs Fc1, Fc2, Fc3L, Fc3Y, Fc5X, and Fc5Y (wild-type Fc $C_H2$ and $C_H3$ domains are labeled with "Wt;" $C_H3$ domains engineered with knobs and holes for heterodimerization are labeled with "kh;" and $C_H3$ domains engineered with homodimerizing electrostatic steering mutations are labeled with "es").

FIG. 1C shows a non-reducing SDS-PAGE analysis of IgG1 and Fc constructs Fc1, Fc2, Fc3L, Fc3Y, Fc5X, and Fc5Y.

DETAILED DESCRIPTION OF THE INVENTION

Figure 1D:
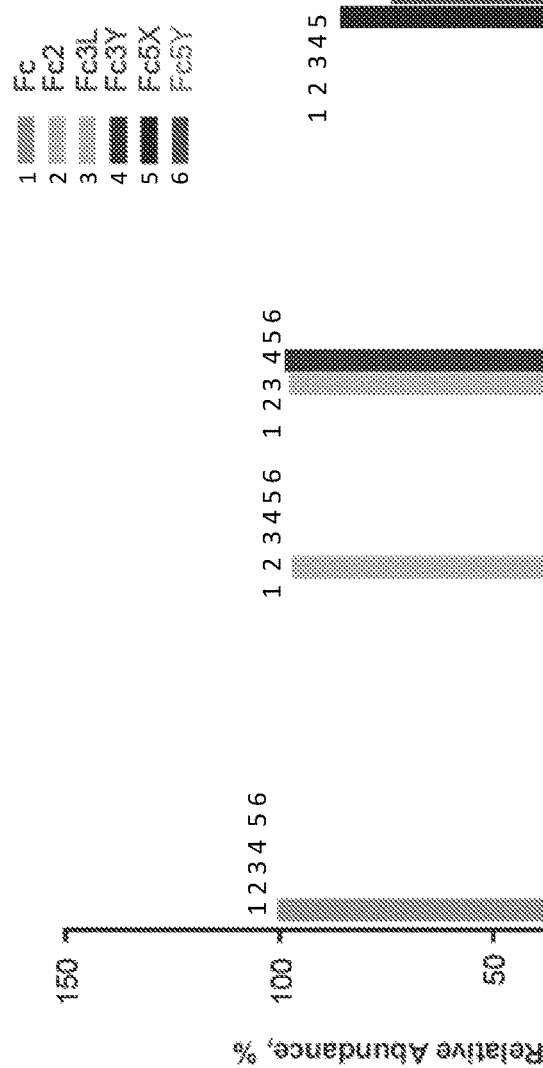
FIG. 1D shows a capillary electrophoresis-SDS (CE-SDS) analysis of Fc constructs Fc1, Fc2, Fc3L, Fc3Y, Fc5X, and Fc5Y.

Therapeutic Fc constructs that include 5 or more Fc domains, e.g., 5-10 Fc domains (e.g., 5, 6, 7, 8, 9, or 10 Fc domains (e.g., 5 Fc domains)), of IgG can be used to induce immune cell activation of the immune response in a subject, to increase phagocytosis of a target cell (i.e., a cancer cell or an infected cell) in a subject, and to treat cancer and an infection in a subject.

I. Activation and Inhibition of Fcγ Receptors

Fc-gamma receptors (FcγRs) bind the Fc portion of immunoglobulin G (IgG) and play important roles in immune activation and regulation. For example, the manifold IgG Fc domains in immune complexes (ICs) engage multiple FcγRs with high avidity, thus triggering signaling cascades that regulate immune cell activation. The human FcγR family contains several activating receptors (FcγRI, FcγRIIa, FcγRIIc, FcγRIIIa, and FcγRIIIb) and one inhibitory receptor (FcγRIIb); all except FcγRI bind to the IgG Fc domain. FcγR signaling is mediated by intracellular domains that contain immune tyrosine activating motifs (ITAMs) for activating FcγRs and immune tyrosine inhibitory motifs (ITIM) for inhibitory receptor FcγRIIb. FcγR crosslinking by ICs results in ITAM phosphorylation by Src family kinases; this activates Syk family kinases and induces downstream signaling networks, which include PI3K and Ras pathways. FcγRIIb inhibitory signaling involves ITIM phosphorylation followed by the recruitment and activation of inhibitory SH2-domain-containing phosphatases and SH2-domain-containing inositol polyphosphate 5' phosphatase. The balance of activating and inhibitory signals modulates immune cell activation and regulates effector functions, which include phagocytosis and antibody-dependent cell-mediated cytotoxicity (ADCC).

Initial therapeutic development of FcγR antagonism was based on designing antibodies that targeted specific FcγRs. Subsequently, the concept of using Fc-polymers was introduced to mimic an immunomodulatory mechanism of intravenous immunoglobulin (IVIg). This approach offers the advantage of antagonism of multiple FcγRs rather than a single receptor. However, rational drug design has been somewhat hampered by an incomplete understanding of the molecular mechanisms that underlie FcγR activation. Therefore, a better understanding of the molecular determinants that control FcγR activation is important for the design of optimal FcγR antagonists. Previous explorations of FcγR activation thresholds relied on ill-defined ICs or IC mimics. Wide molecular weight (MW) distributions are generally expected from common approaches such as heat-aggregation, anti-IgG crosslinking of IgG, or polyclonal antibody-antigen complexes. Narrower MW distributions may be expected from chemically conjugating bovine serum albumin to an antigen, although the size distributions have been generally ill-defined and have not varied linearly with conjugation ratios. Moreover, non-covalent IC mimics may redistribute in size upon purification or dilution. The limited control of aggregate sizes, potential alterations in folding, and limited characterization of IC mimics have hampered determination of the molecular requirements for FcγR activation in these studies.

The present invention describes using a panel of engineered Fc constructs with well-defined size and structure for FcγR activation. Analyses of these Fc constructs in cellular assays revealed that Fc constructs containing five or more Fc domains, e.g., 5-10 Fc domains (e.g., 5, 6, 7, 8, 9, or 10 Fc domains (e.g., 5 Fc domains)), are able to induce activating FcγR (e.g., FcγRI, FcγRIIa, FcγRIIc, FcγRIIIa, and FcγRIIIb) signaling on immune cells.

II. Methods of Using Fc Constructs

Figure 2B:
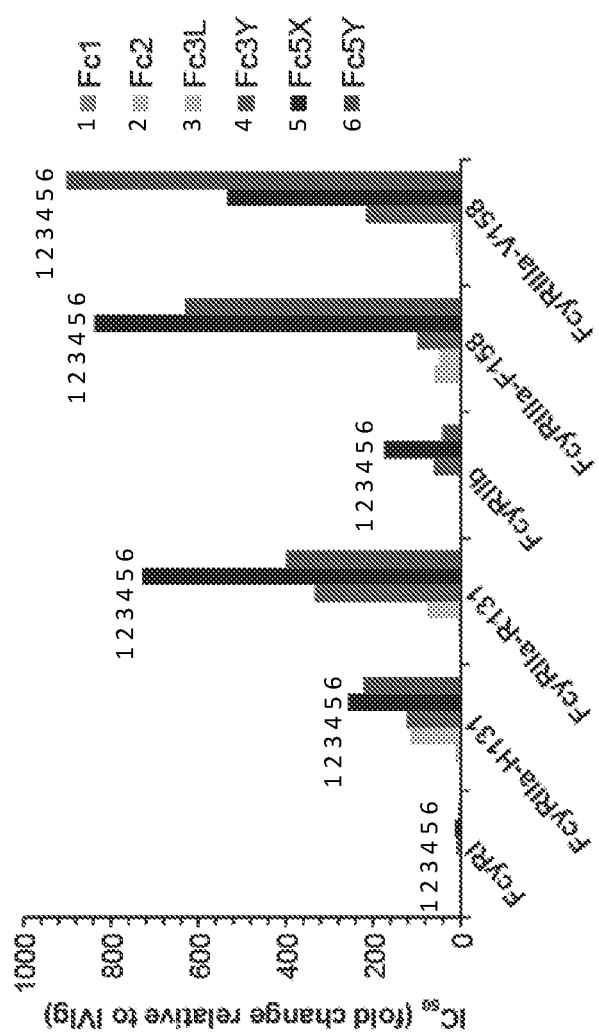
FIG. 2B shows the relative binding of Fc constructs Fc1, Fc2, Fc3L, Fc3Y, Fc5X, and Fc5Y to FcγRI, FcγRIIa-H131, FcγRIIa-R131, FcγRIIb, FcγRIIIa-F158, and FcγRIIIa-V158 using the time-resolved fluorescence resonance energy transfer competitive binding assay.

The invention discloses methods of inducing immune cell activation of the immune response in a subject by administering to the subject a substantially homogenous population of Fc constructs (Fc constructs having 5 or more Fc domains, such as 5-10 Fc domains (e.g., 5, 6, 7, 8, 9, or 10 Fc domains (e.g., 5 Fc domains))). Engineered Fc constructs including 5 or more Fc domains, e.g., 5-10 Fc domains (e.g., 5, 6, 7, 8, 9, or 10 Fc domains (e.g., 5 Fc domains)), may bind to activating Fcγ receptors (e.g., FcγRI, FcγRIIa, FcγRIIc, FcγRIIIa, and FcγRIIIb; FIG. 2B) to induce an immune response. As demonstrated in Example 2 and FIGS. 3A-3D, Fc constructs having 5 Fc domains (Fc5X and Fc5Y) have the ability to activate Syk phosphorylation and calcium flux from primary THP-1 monocytes. Activated monocytes and their differentiated macrophages have the ability to phagocytose or kill target cells.

The invention therefore provides methods of treatment that may be used to treat subjects who are suffering from diseases and disorders such as cancers and infections. In some embodiments, Fc constructs including 5-10 Fc domains (e.g., 5, 6, 7, 8, 9, or 10 Fc domains (e.g., 5 Fc domains)) may be administered to a subject in a therapeutically effective amount to phagocytose or kill cancer cells or infected cells in the subject.

Cancers that are amenable to treatment according to the methods of the invention include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, squamous cell carcinoma, anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor cancer, and soft tissue tumor cancer.

Infections that are amenable to treatment according to the methods of the invention include, but are not limited to, a bacterial infection, a viral infection, a fungal infection, a helmintic infection, and a protozoal infection.

Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus Enteritis (e.g., Enteritis *salmonella*), and bacteria in the genus *Salmonella* (e.g., *Salmonella typhi*).

Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitus C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus).

Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticillioides, F. oxysporum*).

Examples of helminths include, but are not limited to, tapeworms (cestodes), roundworms (nematodes), flukes (trematodes), and monogeneans.

Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

III. Combination Therapy

The methods described herein further include administering an anti-cancer agent or an anti-infective agent in combination with an Fc construct, e.g., an Fc construct including 5-10 Fc domains (e.g., 5, 6, 7, 8, 9, or 10 Fc domains (e.g., 5 Fc domains)). The phrase "in combination with an Fc construct" refers to (1) the anti-cancer agent or anti-infective agent is administered in addition to the Fc construct as a separate entity, i.e., the anti-cancer or anti-infective agent is administered together (i.e., substantially simultaneously) with the Fc construct or administered separately from the Fc construct, or (2) the anti-cancer or anti-infective agent is joined (i.e., covalently conjugated) to the Fc construct and the conjugate is administered in methods described herein.

In some embodiments, the methods further include administering to the subject an anti-cancer agent. In some embodiments, the Fc construct including 5-10 Fc domains (e.g., 5, 6, 7, 8, 9, or 10 Fc domains (e.g., 5 Fc domains)) and the anti-cancer agent are administered substantially simultaneously (as separate entities). In some embodiments, the Fc construct including 5-10 Fc domains (e.g., 5, 6, 7, 8, 9, or 10 Fc domains (e.g., 5 Fc domains)) and the anti-cancer agent are administered separately. In some embodiments, the Fc construct is administered first, followed by administering of the anti-cancer agent. In some embodiments, the anti-cancer agent is administered first, followed by administering of the Fc construct. In some embodiments, the Fc construct and the anti-cancer agent are administered substantially simultaneously (as separate entities), followed by administering of the Fc construct or the anti-cancer agent alone. In some embodiments, the Fc construct or the anti-cancer agent is administered first, followed by administering of the Fc construct and the anti-cancer agent substantially simultaneously (as separate entities).

In some embodiments, the methods include administering a conjugate of an Fc construct (e.g., an Fc construct including 5-10 Fc domains (e.g., 5, 6, 7, 8, 9, or 10 Fc domains (e.g., 5 Fc domains))) and an anti-cancer agent. Fc constructs described herein used in methods of the invention may be joined (i.e., covalently conjugated) to anti-cancer agents. One or more anti-cancer agents may be joined to an Fc construct through chemical means, e.g., chemical conjugation. If desired, a spacer can be inserted between the Fc construct and the anti-cancer agent. Examples of spacers that can be used join an anti-cancer agent to an Fc construct are described in detail further herein.

In some embodiments, the methods further include administering to the subject an anti-infective agent. In some embodiments, the Fc construct including 5-10 Fc domains (e.g., 5, 6, 7, 8, 9, or 10 Fc domains (e.g., 5 Fc domains)) and the anti-infective agent are administered substantially simultaneously (as separate entities). In some embodiments, the Fc construct including 5-10 Fc domains (e.g., 5, 6, 7, 8, 9, or 10 Fc domains (e.g., 5 Fc domains)) and the anti-infective agent are administered separately. In some embodiments, the Fc construct is administered first, followed by administering of the anti-infective agent. In some embodiments, the anti-infective agent is administered first, followed by administering of the Fc construct. In some embodiments, the Fc construct and the anti-infective agent are administered substantially simultaneously (as separate entities), followed by administering of the Fc construct or the anti-infective agent alone. In some embodiments, the Fc construct or the anti-infective agent is administered first, followed by administering of the Fc construct and the anti-infective agent substantially simultaneously (as separate entities). In some embodiments, the anti-infective agent is selected from the group consisting of an anti-bacterial agent, an anti-viral agent, an anti-fungal agent, an anti-helmintic agent, and an anti-protozoal agent. In some embodiments, the anti-infective agent is a microbial antigen (i.e., a microbe component such as a protein or nucleic acid). Examples of anti-infective agents are described in detail further herein.

In some embodiments, the methods include administering a conjugate of an Fc construct (e.g., an Fc construct including 5-10 Fc domains (e.g., 5, 6, 7, 8, 9, or 10 Fc domains (e.g., 5 Fc domains))) and an anti-infective agent. Fc constructs described herein used in methods of the invention may be joined (i.e., covalently conjugated) to anti-infective agents. One or more anti-infective agents may be joined to an Fc construct through chemical means, e.g., chemical conjugation. If desired, a spacer can be inserted between the Fc construct and the anti-infective agent. Examples of spacers that can be used join an anti-infective agent to an Fc construct are described in detail further herein.

IV. Fc Domain Monomers

An Fc domain monomer includes a hinge domain, a $C_H2$ antibody constant domain, and a $C_H3$ antibody constant domain. The Fc domain monomer can be of immunoglobulin antibody isotype IgG, IgE, IgM, IgA, or IgD. The Fc domain monomer may also be of any immunoglobulin antibody isotype (e.g., IgG1, IgG2a, IgG2b, IgG3, or IgG4). The Fc domain monomers may also be hybrids, e.g., with the hinge and $C_H2$ from IgG1 and the $C_H3$ from IgA, or with the hinge and $C_H2$ from IgG1 but the $C_H3$ from IgG3. A dimer of Fc domain monomers is an Fc domain (further defined herein) that can bind to an Fc receptor, e.g., FcγRIIIa, which is a receptor located on the surface of leukocytes. In the present invention, the $C_H3$ antibody constant domain of an Fc domain monomer may contain amino acid substitutions at the interface of the $C_H3$-$C_H3$ antibody constant domains to promote their association with each other. In some embodiments, an Fc domain monomer includes an additional moiety, e.g., an albumin-binding peptide or a purification peptide, attached to the N- or C-terminus. In some embodiments, an Fc domain monomer does not contain any type of antibody variable region, e.g., $V_H$, $V_L$, a complementarity determining region (CDR), or a hypervariable region (HVR). In some embodiments, an Fc domain monomer contains an antibody variable region, e.g., $V_H$, $V_L$, a complementarity determining region (CDR), or a hypervariable region (HVR).

In some embodiments, an Fc domain monomer in an Fc construct described herein (e.g., an Fc construct having 5-10 Fc domains (e.g., 5 Fc domains)) may have a sequence that is at least 95% identical (e.g., at least 97%, 99%, or 99.5% identical) to the sequence of a wild-type Fc domain monomer (SEQ ID NO: 39). In some embodiments, an Fc domain monomer in an Fc construct described herein (e.g., an Fc construct having five Fc domains) may have a sequence that is at least 95% identical (e.g., at least 97%, 99%, or 99.5% identical) to the sequence of any one of SEQ ID NOs: 40-46. In certain embodiments, an Fc domain monomer in the Fc construct may have a sequence that is at least 95% identical (e.g., at least 97%, 99%, or 99.5% identical) to the sequence of any one of SEQ ID NOs: 42, 45, and 46.

```
SEQ ID NO: 39:
wild-type human IgG1 Fc domain monomer amino
acid sequence
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GK

SEQ ID NO: 40
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLSLSP

GK

SEQ ID NO: 41
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLSLSP

G
```

-continued

SEQ ID NO: 42
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

DELTKNQVSLSCAVDGFYPSDIAVEWESNGQPENNYKTTPPVLDS

DGSFFLVSKLTVDKSRWQQGNVFSCSVMHEALHNHYTQKSLSLSP

G

SEQ ID NO: 43
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPCR

DELTKNQVSLWCLVKGFYPSDIAVEWESNGQPENNYKTTPPVLDS

DGSFFLYSKLTVDKSRWQQGNVFSCSVMHEALHNHYTQKSLSLSP

GK

SEQ ID NO: 44
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLKS

DGSFFLYSDLTVDKSRWQQGNVFSCSVMHEALHNHYTQKSLSLSP

GK

SEQ ID NO: 45
DKTHTCPPCPAPELLGGPSVFLFPPKPKDILMISRTPEVICVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLKS

DGSFFLYSDLTVDKSRWQQGNVFSCSVMHEALHNHYTQKSLSLSP

G

SEQ ID NO: 46
DKTHTCPPCPAPELLGGPSVFLFPPKPKDILMISRTPEVICVVVD

VSHEDPEVKFNVVYVDGVEVHNAKTKPREEQYNSTYRVVSVLTVL

HQDWLNGKEYKCKVSNKALPAPIEKTISKAKGQPREPQVYTLPPC

RDKLIKNQVSLWCLVKGFYPSDIAVEVVESNGQPENNYKTTPPVL

DSDGSFFLYSKLTVDKSRWQQGNVFSCSVMHEALHNHYTQKSLSL

SPGK

V. Fc Domains

As defined herein, an Fc domain includes two Fc domain monomers that are dimerized by the interaction between the $C_H3$ antibody constant domains. In some embodiments, an Fc domain does not include a variable region of an antibody, e.g., $V_H$, $V_L$, CDR, or HVR. In some embodiments, an Fc domain includes a variable region of an antibody, e.g., $V_H$, $V_L$, CDR, or HVR. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcε receptors (FcεR)), and/or the neonatal Fc receptor (FcRn). In some embodiments, an Fc domain of the present invention binds to an Fcγ receptor (e.g., FcγRI (CD64), FcγRIIa (CD32), FcγRIIb (CD32), FcγRIIIa (CD16a), FcγRIIIb (CD16b)), and/or FcγRIV and/or the neonatal Fc receptor (FcRn).

VI. Dimerization Selectivity Modules

In the present invention, a dimerization selectivity module is the part of the Fc domain monomer that facilitates the preferred pairing of two Fc domain monomers to form an Fc domain. Specifically, a dimerization selectivity module is that part of the $C_H3$ antibody constant domain of an Fc domain monomer which includes amino acid substitutions positioned at the interface between interacting $C_H3$ antibody constant domains of two Fc domain monomers. In a dimerization selectivity module, the amino acid substitutions make favorable the dimerization of the two $C_H3$ antibody constant domains as a result of the compatibility of amino acids chosen for those substitutions. The ultimate formation of the favored Fc domain is selective over other Fc domains which form from Fc domain monomers lacking dimerization selectivity modules or with incompatible amino acid substitutions in the dimerization selectivity modules. This type of amino acid substitution can be made using conventional molecular cloning techniques well-known in the art, such as QuikChange® mutagenesis.

In some embodiments, a dimerization selectivity module includes an engineered cavity (described further herein) in the $C_H3$ antibody constant domain. In other embodiments, a dimerization selectivity module includes an engineered protuberance (described further herein) in the $C_H3$ antibody constant domain. To selectively form an Fc domain, two Fc domain monomers with compatible dimerization selectivity modules, e.g., one $C_H3$ antibody constant domain containing an engineered cavity and the other $C_H3$ antibody constant domain containing an engineered protuberance, combine to form a protuberance-into-cavity pair of Fc domain monomers. Engineered protuberances and engineered cavities are examples of heterodimerizing selectivity modules, which can be made in the $C_H3$ antibody constant domains of Fc domain monomers in order to promote favorable heterodimerization of two Fc domain monomers that have compatible heterodimerizing selectivity modules.

In other embodiments, an Fc domain monomer with a dimerization selectivity module containing positively-charged amino acid substitutions and an Fc domain monomer with a dimerization selectivity module containing negatively-charged amino acid substitutions may selectively combine to form an Fc domain through the favorable electrostatic steering (described further herein) of the charged amino acids. In some embodiments, an Fc domain monomer may include one or more of the following positively-charged and negatively-charged amino acid substitutions: K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids. In some embodiments, reverse charge amino acid substitutions may be used as heterodimerizing selectivity modules, wherein two Fc domain monomers containing different, but compatible, reverse charge amino acid substitutions combine to form a heterodimeric Fc domain. Specific dimerization selectivity modules are further listed, without limitation, in Tables 1 and 2A-2C described further below.

In other embodiments, two Fc domain monomers include homodimerizing selectivity modules containing identical reverse charge mutations in at least two positions within the ring of charged residues at the interface between $C_H3$ domains. Homodimerizing selectivity modules are reverse charge amino acid substitutions that promote the homodimerization of Fc domain monomers to form a homodimeric Fc domain. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. In one embodiment, an Fc domain includes Fc domain monomers including the double mutants K409D/D399K, K392D/D399K, E357K/K370E, D356K/K439D, K409E/D399K, K392E/D399K, E357K/K370D, or D356K/K439E. In another embodiment, an Fc domain includes Fc domain monomers including quadruple mutants combining any pair of the double mutants, e.g., K409D/D399K/E357K/K370E. Examples of homodimerizing selectivity modules are further shown in Tables 2B and 2C.

In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer charge mutation K370D and engineered cavities Y349C, T366S, L368A, and Y407V and another Fc domain monomer containing reversed charge mutation E357K and engineered protuberances S354C and T366W may selectively combine to form an Fc domain.

The formation of such Fc domains is promoted by the compatible amino acid substitutions in the $C_H3$ antibody constant domains. Two dimerization selectivity modules containing incompatible amino acid substitutions, e.g., both containing engineered cavities, both containing engineered protuberances, or both containing the same charged amino acids at the $C_H3$-$C_H3$ interface, will not promote the formation of a heterodimeric Fc domain.

Furthermore, other methods used to promote the formation of Fc domains with defined Fc domain monomers include, without limitation, the LUZ-Y approach (International Patent Application Publication No. WO2011034605) which includes C-terminal fusion of a monomer α-helices of a leucine zipper to each of the Fc domain monomers to allow heterodimer formation, as well as strand-exchange engineered domain (SEED) body approach (Davis et al., *Protein Eng Des Sel.* 23:195-202, 2010) that generates Fc domain with heterodimeric Fc domain monomers each including alternating segments of IgA and IgG $C_H3$ sequences.

VII. Engineered Cavities and Engineered Protuberances

The use of engineered cavities and engineered protuberances (or the "knob-into-hole" strategy) is described by Carter and co-workers (Ridgway et al., Protein Eng. 9:617-612, 1996; Atwell et al., J Mol Biol. 270:26-35, 1997; Merchant et al., Nat Biotechnol. 16:677-681, 1998). The knob and hole interaction favors heterodimer formation, whereas the knob-knob and the hole-hole interaction hinder homodimer formation due to steric clash and deletion of favorable interactions. The "knob-into-hole" technique is also disclosed in U.S. Pat. No. 5,731,168.

In the present invention, engineered cavities and engineered protuberances are used in the preparation of the Fc constructs described herein. An engineered cavity is a void that is created when an original amino acid in a protein is replaced with a different amino acid having a smaller side-chain volume. An engineered protuberance is a bump that is created when an original amino acid in a protein is replaced with a different amino acid having a larger side-chain volume. Specifically, the amino acid being replaced is in the $C_H3$ antibody constant domain of an Fc domain monomer and is involved in the dimerization of two Fc domain monomers. In some embodiments, an engineered cavity in one $C_H3$ antibody constant domain is created to accommodate an engineered protuberance in another $C_H3$ antibody constant domain, such that both $C_H3$ antibody constant domains act as dimerization selectivity modules (e.g., heterodimerizing selectivity modules) (described above) that promote or favor the dimerization of the two Fc domain monomers. In other embodiments, an engineered cavity in one $C_H3$ antibody constant domain is created to better accommodate an original amino acid in another $C_H3$ antibody constant domain. In yet other embodiments, an engineered protuberance in one $C_H3$ antibody constant domain is created to form additional interactions with original amino acids in another $C_H3$ antibody constant domain.

An engineered cavity can be constructed by replacing amino acids containing larger side chains such as tyrosine or tryptophan with amino acids containing smaller side chains such as alanine, valine, or threonine. Specifically, some dimerization selectivity modules (e.g., heterodimerizing selectivity modules) (described further above) contain engineered cavities such as Y407V mutation in the $C_H3$ antibody constant domain. Similarly, an engineered protuberance can be constructed by replacing amino acids containing smaller side chains with amino acids containing larger side chains. Specifically, some dimerization selectivity modules (e.g., heterodimerizing selectivity modules) (described further above) contain engineered protuberances such as T366W mutation in the $C_H3$ antibody constant domain. In some embodiments, engineered cavities and engineered protuberances are also combined with inter-$C_H3$ domain disulfide bond engineering to enhance heterodimer formation. In some embodiments, the cavity Fc contains an Y349C mutation, and the protuberance Fc contains an S354C mutation. In some embodiments, an Fc domain monomer containing engineered cavities Y349C, T366S, L368A, and Y407V may selectively combine with another Fc domain monomer containing engineered protuberances S354C and T366W to form an Fc domain. Other engineered cavities and engineered protuberances, in combination with either disulfide bond engineering or structural calculations (mixed HA-TF) are included, without limitation, in Table 1.

TABLE 1

| Strategy | $C_H3$ antibody constant domain of Fc domain monomer 1 | $CH_3$ antibody constant domain at Fc domain monomer 2 | Reference |
|---|---|---|---|
| Engineered cavities and protuberances ("knob-into-hole") | Y407T | T366Y | U.S. Pat. No. 8,216,805 |
|  | Y407A | T366W | U.S. Pat. No. 8,216,805 |
|  | F405A | T394W | U.S. Pat. No. 8,216,805 |
|  | Y407T | T366Y | U.S. Pat. No. 8,216,805 |
|  | T394S | F405W | U.S. Pat. No. 8,216,805 |
|  | T394W:Y407T | T366Y:F405A | U.S. Pat. No. 8,216,805 |
|  | T394S:Y407A | T366W:F405W | U.S. Pat. No. 8,216,805 |
|  | T366W:T394S | F405W:Y407A | U.S. Pat. No. 8,216,805 |
| Engineered cavities and protuberances ("knob-into-hole"), S-S engineering | T366S.L36SA:Y407V:Y349C | T366W:S354C | Zeidler et al., J Immonol 163:1246-52. 1999 |
| Mixed HA-TF | S364H:F405A | Y349T:T394F | WO2006106905 |

Replacing an original amino acid residue in the $C_H3$ antibody constant domain with a different amino acid residue can be achieved by altering the nucleic acid encoding the original amino acid residue. The upper limit for the number of original amino acid residues that can be replaced is the total number of residues in the interface of the $C_H3$ antibody constant domains, given that sufficient interaction at the interface is still maintained.

VIII. Electrostatic Steering

Electrostatic steering is the utilization of favorable electrostatic interactions between oppositely charged amino acids in peptides, protein domains, and proteins to control the formation of higher ordered protein molecules. A method of using electrostatic steering effects to alter the interaction of antibody domains to reduce for formation of homodimer in favor of heterodimer formation in the generation of bi-specific antibodies is disclosed in U.S. Patent Application Publication No. 2014-0024111.

In the present invention, electrostatic steering is used to control the dimerization of Fc domain monomers and the formation of Fc constructs. In particular, to control the dimerization of Fc domain monomers using electrostatic steering, one or more amino acid residues that make up the $C_H3$-$C_H3$ interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In other embodiments, a negatively-charged amino acid in the interface is replaced with a positively-charged amino acid. The charged amino acids may be introduced to one of the interacting $C_H3$ antibody constant domains, or both. By introducing charged amino acids to the interacting $C_H3$ antibody constant domains, dimerization selectivity modules (described further above) are created that can selectively form dimers of Fc domain monomers as controlled by the electrostatic steering effects resulting from the interaction between charged amino acids.

In some embodiments, to create a dimerization selectivity module including reversed charges that can selectively form dimers of Fc domain monomers as controlled by the electrostatic steering effects, the two Fc domain monomers may be selectively formed through heterodimerization or homodimerization. For example, an Fc domain monomer having amino acid Asp399 in the $C_H3$ antibody constant domain replaced with Lys, and amino acid Lys409 replaced with Asp may form a homodimeric Fc domain.

Heterodimerization of Fc Domain Monomers

Heterodimerization of Fc domain monomers can be promoted by introducing different, but compatible, mutations in the two Fc domain monomers, such as the charge residue pairs included, without limitation, in Table 2A. In some embodiments, an Fc domain monomer may include one of the following positively-charged and negatively-charged amino acid substitutions: D356K, D356R, E357K, E357R, K370D, K370E, K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids.

Figure 4:
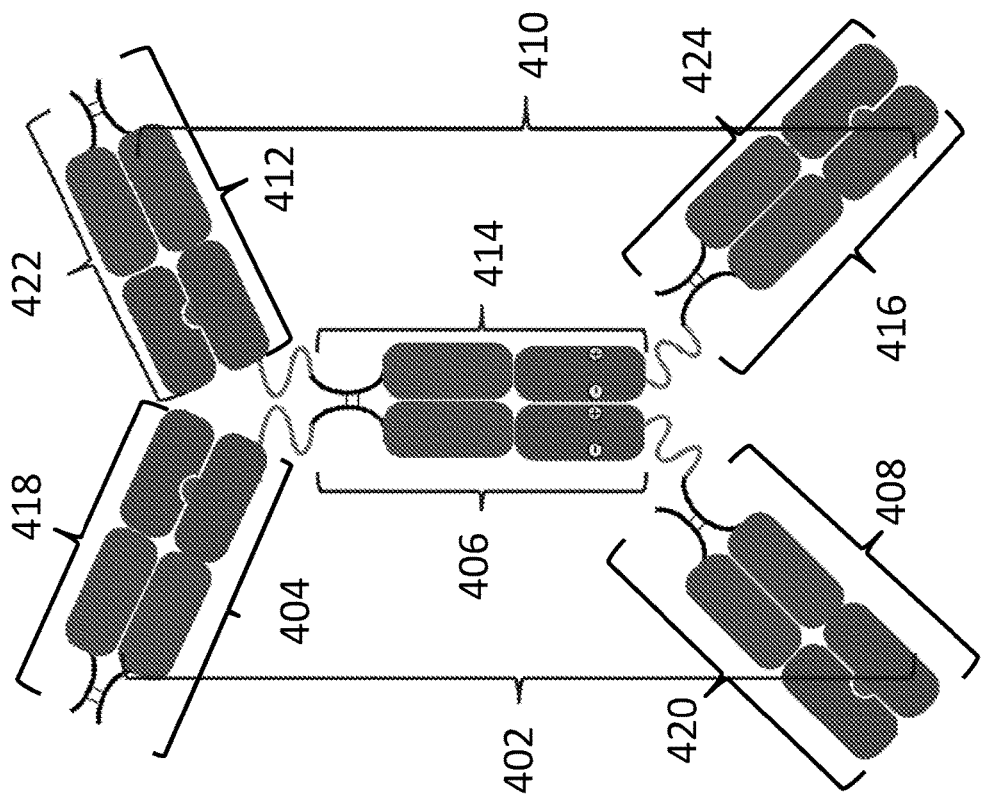
FIG. 4 is an illustration of an Fc construct containing five Fc domains formed from six polypeptides (Fc5X). The first and second polypeptides (402 and 410) each contain three Fc domain monomers (404, 406, 408, and 412, 414, 416, respectively) joined in a tandem series. Specifically, in polypeptide 402 or 410, a first protuberance-containing Fc domain monomer (404 or 412) is connected to a second Fc domain monomer containing different charged amino acids at the $C_H3$-$C_H3$ interface than the wild-type sequence (406 or 414), which is connected to a third protuberance-containing Fc domain monomer (408 or 416). The third through sixth polypeptides (418, 420, 422, and 424) each contain a cavity-containing Fc domain monomer and form an Fc domain with each of Fc domain monomers 404, 408, 412 and 416, respectively.

For example, in an Fc construct having five Fc domains, four of the five Fc domains may be formed by the heterodimerization of two Fc domain monomers, as promoted by the electrostatic steering effects. A "heterodimeric Fc domain" refers to an Fc domain that is formed by the heterodimerization of two Fc domain monomers, wherein the two Fc domain monomers contain different reverse charge mutations (heterodimerizing selectivity modules) (see, e.g., mutations in Table 2A) that promote the favorable formation of these two Fc domain monomers. For example, as shown in FIG. 4, in an Fc construct having five Fc domains, a heterodimeric Fc domain formed by Fc domain monomers 404 and 418, 408 and 420, 412 and 422, or 416 and 424. A heterodimeric Fc domain may be formed by an Fc domain monomer containing E357K and another Fc domain monomer containing K370D.

??TABLE 2A

| Reverse charge mutation(s) in $C_H3$ antibody constant domain of Fc domain monomer 1 | Reverse charge mutation(s) in $C_H3$ antibody constant domain of Fc domain monomer 2 |
|---|---|
| K409D | D399K |
| K409D | D399R |
| K409E | D399K |
| K409E | D399R |
| K392D | D399K |
| K392D | D399R |
| K392E | D399K |
| K392E | D399R |
| K370D | E357K |
| K370D | E357R |
| K370E | E357K |

TABLE 2A-continued

| Reverse charge mutation(s) in $C_H3$ antibody constant domain of Fc domain monomer 1 | Reverse charge mutation(s) in $C_H3$ antibody constant domain of Fc domain monomer 2 |
|---|---|
| K370E | E357R |
| K370D | D356K |
| K370D | D356R |
| K370E | D356K |
| K370E | D356R |
| K409D, K392D | D399K, E356K |
| K370E, K409D, K439E | E356K, E357K, D399K |

Homodimerization of Fc Domain Monomers

Homodimerization of Fc domain monomers can be promoted by introducing the same electrostatic steering mutations (homodimerizing selectivity modules) in both Fc domain monomers in a symmetric fashion, such as the double mutants K409D/D399K or K392D/D399K. In some embodiments, two Fc domain monomers include homodimerizing selectivity modules containing identical reverse charge mutations in at least two positions within the ring of charged residues at the interface between $C_H3$ domains. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. Electrostatic steering mutations that may be introduced into an Fc domain monomer to promote its homodimerization are shown, without limitation, in Tables 2B and 2C. In one embodiment, an Fc domain includes two Fc domain monomers each including the double reverse charge mutants (Table 2B), e.g., K409D/D399K. In another embodiment, an Fc domain includes two Fc domain monomers each including quadruple reverse mutants (Table 2C), e.g., K409D/D399K/K370D/E357K.

For example, in an Fc construct having five Fc domains, one of the five Fc domains may be formed by the homodimerization of two Fc domain monomers, as promoted by the electrostatic steering effects. A "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). For example, as shown in FIG. 4, in an Fc construct having five Fc domains, a homodimeric Fc domain may be formed by Fc domain monomers 406 and 414. A homodimeric Fc domain may be formed by two Fc domain monomers each containing the double mutants K409D/D399K.

TABLE 2B

| Reverse charge mutation(s) in $C_H3$ antibody constant domain of each of the two Fc domain monomers in a homodimeric Fc domain |
|---|
| K409D/D399K |
| K409D/D399R |
| K409E/D399K |
| K409E/D399R |
| K392D/D399K |
| K392D/D399R |
| K392E/D399K |
| K392E/D399R |
| K370D/E357K |
| K370D/E357R |
| K370E/E357K |
| K370E/E357R |
| K370D/D356K |

TABLE 2B-continued

| Reverse charge mutation(s) in $C_H3$ antibody constant domain of each of the two Fc domain monomers in a homodimeric Fc domain |
|---|
| K370D/D356R |
| K370E/D356K |
| K370E/D356R |

TABLE 20

| Reverse charge mutation(s) in $C_H3$ antibody constant domain of each of the two Fc domain monomers in a homodimeric Fc domain | Reverse charge mutation(s) in $C_H3$ antibody constant domain of each of the two Fc domain monomers in a homodimeric Fc domain |
|---|---|
| K409D/D399K/K370D/E357K | K392D/D399K/K370D/E357K |
| K409D/D399K/K370D/E357R | K392D/D399K/K370D/E357R |
| K409D/D399K/K370E/E357K | K392D/D399K/K370E/E357K |
| K409D/D399K/K370E/E357R | K392D/D399K/K370E/E357R |
| K409D/D399K/K370D/D356K | K392D/D399K/K370D/D356K |
| K409D/D399K/K370D/D356R | K392D/D399K/K370D/D356R |
| K409D/D399K/K370E/D356K | K392D/D399K/K370E/D356K |
| K409D/D399K/K370E/D356R | K392D/D399K/K370E/D356R |
| K409D/D399R/K370D/E357K | K392D/D399R/K370D/E357K |
| K409D/D399R/K370D/E357R | K392D/D399R/K370D/E357R |
| K409D/D399R/K370E/E357K | K392D/D399R/K370E/E357K |
| K409D/D399R/K370E/E357R | K392D/D399R/K370E/E357R |
| K409D/D399R/K370D/D356K | K392D/D399R/K370D/D356K |
| K409D/D399R/K370D/D356R | K392D/D399R/K370D/D356R |
| K409D/D399R/K370E/D356K | K392D/D399R/K370E/D356K |
| K409D/D399R/K370E/D356R | K392D/D399R/K370E/D356R |
| K409E/D399K/K370D/E357K | K392E/D399K/K370D/E357K |
| K409E/D399K/K370D/E357R | K392E/D399K/K370D/E357R |
| K409E/D399K/K370E/E357K | K392E/D399K/K370E/E357K |
| K409E/D399K/K370E/E357R | K392E/D399K/K370E/E357R |
| K409E/D399K/K370D/D356K | K392E/D399K/K370D/D356K |
| K409E/D399K/K370D/D356R | K392E/D399K/K370D/D356R |
| K409E/D399K/K370E/D356K | K392E/D399K/K370E/D356K |
| K409E/D399K/K370E/D356R | K392E/D399K/K370E/D356R |
| K409E/D399R/K370D/E357K | K392E/D399R/K370D/E357K |
| K409E/D399R/K370D/E357R | K392E/D399R/K370D/E357R |
| K409E/D399R/K370E/E357K | K392E/D399R/K370E/E357K |
| K409E/D399R/K370E/E357R | K392E/D399R/K370E/E357R |
| K409E/D399R/K370D/D356K | K392E/D399R/K370D/D356K |
| K409E/D399R/K370D/D356R | K392E/D399R/K370D/D356R |
| K409E/D399R/K370E/D356K | K392E/D399R/K370E/D356K |
| K409E/D399R/K370E/D356R | K392E/D399R/K370E/D356R |

IX. Linkers

In the present invention, a linker is used to describe a linkage or connection between polypeptides or protein domains and/or associated non-protein moieties. In some embodiments, a linker is a linkage or connection between at least two Fc domain monomers, for which the linker connects the C-terminus of the $C_H3$ antibody constant domain of a first Fc domain monomer to the N-terminus of the hinge domain of a second Fc domain monomer, such that the two Fc domain monomers are joined to each other in tandem series. In other embodiments, a linker is a linkage between an Fc domain monomer and any other protein domains that are attached to it. For example, a linker can attach the C-terminus of the $C_H3$ antibody constant domain of an Fc domain monomer to the N-terminus of an albumin-binding peptide. In another example, a linker can connect the C-terminus of a $C_H1$ antibody constant domain to the N-terminus of the hinge domain of an Fc domain monomer. In yet other embodiments, a linker can connect two individual protein domains (not including an Fc domain), for example, the C-terminus of a $C_L$ antibody constant domain can be attached to the N-terminus of a $C_H1$ antibody constant domain by way of a linker.

A linker can be a simple covalent bond, e.g., a peptide bond, a synthetic polymer, e.g., a polyethylene glycol (PEG) polymer, or any kind of bond created from a chemical reaction, e.g. chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two Fc domain monomer, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

Spacer

In the present invention, a linker between two Fc domain monomers can be an amino acid spacer including 3-200 amino acids (e.g., 3-200, 3-180, 3-160, 3-140, 3-120, 3-100, 3-90, 3-80, 3-70, 3-60, 3-50, 3-45, 3-40, 3-35, 3-30, 3-25, 3-20, 3-15, 3-10, 3-9, 3-8, 3-7, 3-6, 3-5, 3-4, 4-200, 5-200, 6-200, 7-200, 8-200, 9-200, 10-200, 15-200, 20-200, 25-200, 30-200, 35-200, 40-200, 45-200, 50-200, 60-200, 70-200, 80-200, 90-200, 100-200, 120-200, 140-200, 160-200, or 180-200 amino acids). In some embodiments, a linker between two Fc domain monomers is an amino acid spacer containing at least 12 amino acids, such as 12-200 amino acids (e.g., 12-200, 12-180, 12-160, 12-140, 12-120, 12-100, 12-90, 12-80, 12-70, 12-60, 12-50, 12-40, 12-30, 12-20, 12-19, 12-18, 12-17, 12-16, 12-15, 12-14, or 12-13 amino acids) (e.g., 14-200, 16-200, 18-200, 20-200, 30-200, 40-200, 50-200, 60-200, 70-200, 80-200, 90-200, 100-200, 120-200, 140-200, 160-200, 180-200, or 190-200 amino acids). In some embodiments, a linker between two Fc domain monomers is an amino acid spacer containing 12-30 amino acids (e.g., 12, 13, 14, 15, 16, 17, 18, 19, 20, 21, 22, 23, 24, 25, 26, 27, 28, 29, or 30 amino acids). Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 1), GGSG (SEQ ID NO: 2), or SGGG (SEQ ID NO: 3). In certain embodiments, a spacer can contain 2 to 12 amino acids including motifs of GS, e.g., GS, GSGS (SEQ ID NO: 4), GSGSGS (SEQ ID NO: 5), GSGSGSGS (SEQ ID NO: 6), GSGSGSGSGS (SEQ ID NO: 7), or GSGSGSGSGSGS (SEQ ID NO: 8). In certain other embodiments, a spacer can contain 3 to 12 amino acids including motifs of GGS, e.g., GGS, GGSGGS (SEQ ID NO: 9), GGSGGSGGS (SEQ ID NO: 10), and GGSGGSGGSGGS (SEQ ID NO: 11). In yet other embodiments, a spacer can contain 4 to 12 amino acids including motifs of GGSG (SEQ ID NO: 2), e.g., GGSGGGSG (SEQ ID NO: 12), or GGSGGGSGGGSG (SEQ ID NO: 13). In other embodiments, a spacer can contain motifs of GGGGS (SEQ ID NO: 1), e.g., GGGGSGGGGSGGGGS (SEQ ID NO: 14). In certain embodiments, a spacer is SGGGSGGGSGGGSGGGSGGG (SEQ ID NO: 24).

In some embodiments, a spacer between two Fc domain monomers contains only glycine residues, e.g., at least 4 glycine residues (e.g., 4-200, 4-180, 4-160, 4-140, 4-40, 4-100, 4-90, 4-80, 4-70, 4-60, 4-50, 4-40, 4-30, 4-20, 4-19, 4-18, 4-17, 4-16, 4-15, 4-14, 4-13, 4-12, 4-11, 4-10, 4-9, 4-8, 4-7, 4-6 or 4-5 glycine residues) (e.g., 4-200, 6-200, 8-200, 10-200, 12-200, 14-200, 16-200, 18-200, 20-200, 30-200, 40-200, 50-200, 60-200, 70-200, 80-200, 90-200, 100-200, 120-200, 140-200, 160-200, 180-200, or 190-200 glycine residues). In certain embodiments, a spacer has 4-30 glycine residues (e.g., 4, 5, 6, 7, 8, 9, 10, 11, 12, 13, 14, 15, 16, 17, 18, 19, 20, 21, 22, 23, 24, 25, 26, 27, 28, 29, or 30 glycine residues). In some embodiments, a spacer containing only glycine residues may not be glycosylated (e.g., O-linked glycosylation, also referred to as O-glycosylation) or may have a decreased level of glycosylation (e.g., a decreased level of O-glycosylation) (e.g., a decreased level of O-glycosylation with glycans such as xylose, mannose, sialic acids, fucose (Fuc), and/or galactose (Gal) (e.g., xylose)) as compared to, e.g., a spacer containing one or more serine residues (e.g., SGGGSGGGSGGGSGGGSGGG (SEQ ID NO: 24)).

In some embodiments, a spacer containing only glycine residues may not be O-glycosylated (e.g., O-xylosylation) or may have a decreased level of O-glycosylation (e.g., a decreased level of O-xylosylation) as compared to, e.g., a spacer containing one or more serine residues (e.g., SGGGSGGGSGGGSGGGSGGG (SEQ ID NO: 24)).

In some embodiments, a spacer containing only glycine residues may not undergo proteolysis or may have a decreased rate of proteolysis as compared to, e.g., a spacer containing one or more serine residues (e.g., SGGGSGGGSGGGSGGGSGGG (SEQ ID NO: 24)).

In certain embodiments, a spacer can contain motifs of GGGG (SEQ ID NO: 30), e.g., GGGGGGGG (SEQ ID NO: 31), GGGGGGGGGGGG (SEQ ID NO: 32), GGGGGGGGGGGGGGGG (SEQ ID NO: 33), or GGGGGGGGGGGGGGGGGGGG (SEQ ID NO: 34). In certain embodiments, a spacer can contain motifs of GGGGG (SEQ ID NO: 35), e.g., GGGGGGGGGG (SEQ ID NO: 36), GGGGGGGGGGGGGGG (SEQ ID NO: 37), or GGGGGGGGGGGGGGGGGGGG (SEQ ID NO: 38). In certain embodiments, a spacer is GGGGGGG-GGGGGGGGGGGGG (SEQ ID NO: 38).

In other embodiments, a spacer can also contain amino acids other than glycine and serine, e.g., GENLYFQSGG (SEQ ID NO: 15), SACYCELS (SEQ ID NO: 16), RSIAT (SEQ ID NO: 17), RPACKIPNDLKQKVMNH (SEQ ID NO: 18), GGSAGGSGSGSSGGSSGASGTGTAG-GTGSGSGTGSG (SEQ ID NO: 19), AAANSSI-DLISVPVDSR (SEQ ID NO: 20), or GGSGGGSEGGGSEGGGSEGGGSEGGGSGGGS (SEQ ID NO: 21). In certain embodiments in the present invention, a 12-, 18-, or 20-amino acid peptide spacer is used to connect two Fc domain monomers in tandem series. The 12-, 18-, and 20-amino acid peptide spacers consist of sequences GGGSGGGSGGGS (SEQ ID NO: 22), GGSGGGSGGGSGGGSGGS (SEQ ID NO: 23), and SGGGSGGGSGGGSGGGSGGG (SEQ ID NO: 24), respectively.

In certain embodiments in the present invention, a 12- or 20-amino acid peptide spacer may be used to connect two Fc domain monomers in tandem series (e.g., polypeptides 404 and 406 in FIG. 4). The 12- and 20-amino acid peptide spacers may consist of sequences GGGSGGGSGGGS (SEQ ID NO: 22) and SGGGSGGGSGGGSGGGSGGG (SEQ ID NO: 24), respectively. In other embodiments, an 18-amino acid peptide spacer consisting of sequence GGSGGGSGGGSGGGSGGS (SEQ ID NO: 23) may be used.

In some embodiments, a spacer between two Fc domain monomers may have a sequence that is at least 75% identical (e.g., at least 77%, 79%, 81%, 83%, 85%, 87%, 89%, 91%, 93%, 95%, 97%, 99%, or 99.5% identical) to the sequence of any one of SEQ ID NOs: 1-24 and 30-38 described above. In certain embodiments, a spacer between two Fc domain monomers may have a sequence that is at least 80% identical (e.g., at least 82%, 85%, 87%, 90%, 92%, 95%, 97%, 99%, or 99.5% identical) to the sequence of any one of SEQ ID NOs: 14, 24, 37, and 38. In certain embodiments, a spacer between two Fc domain monomers may have a sequence that is at least 80% identical (e.g., at least 82%, 85%, 87%, 90%, 92%, 95%, 97%, 99%, or 99.5%) to the sequence of SEQ ID NO: 37 or 38.

X. Serum Protein-Binding Peptides

Binding to serum protein peptides can improve the pharmacokinetics of protein pharmaceuticals, and in particular the Fc constructs described here may be fused with serum protein-binding peptides.

As one example, albumin-binding peptides that can be used in the methods and compositions described here are generally known in the art. In one embodiment, the albumin binding peptide includes the sequence DICLPRWGCLW (SEQ ID NO: 25). In some embodiments, the albumin binding peptide has a sequence that is at least 80% identical (e.g., 80%, 90%, or 100% identical) to the sequence of SEQ ID NO: 25.

In the present invention, albumin-binding peptides may be attached to the N- or C-terminus of certain polypeptides in the Fc construct by way of a linker. In some embodiments, an albumin-binding peptide may be attached to the N- or C-terminus (e.g., C-terminus) of one or more polypeptides in an Fc construct (e.g., Fc construct Fc5X, Fc5Y, or Fc5Y-invert) (FIGS. 4-6, respectively) by way of a linker. In some embodiments, an albumin-binding peptide may be attached to the N- or C-terminus (e.g., C-terminus) of the first polypeptide or the second polypeptide in an Fc construct (e.g., Fc construct Fc5X, Fc5Y, or Fc5Y-invert) (FIGS. 4-6, respectively) by way of a linker. In some embodiments, an albumin-binding peptide may be attached to the C-terminus of the first polypeptide or the second polypeptide in an Fc construct (e.g., Fc construct Fc5X, Fc5Y, or Fc5Y-invert) (FIGS. 4-6, respectively) by way of a linker.

Albumin-binding peptides can be fused genetically to Fc constructs or attached to Fc constructs through chemical means, e.g., chemical conjugation. If desired, a spacer can be inserted between the Fc construct and the albumin-binding peptide. Without being bound to a theory, it is expected that inclusion of an albumin-binding peptide in an Fc construct of the invention may lead to prolonged retention of the therapeutic protein through its binding to serum albumin.

XI. Anti-Cancer Agents

In some embodiments of the methods of the invention, anti-cancer agents may be used in combination with Fc constructs including 5-10 Fc domains (e.g., 5, 6, 7, 8, 9, or 10 Fc domains (e.g., 5 Fc domains)). In some embodiments, the anti-cancer agent is administered in addition to the Fc construct as a separate entity, i.e., the anti-cancer agent is administered together (i.e., substantially simultaneously) with the Fc construct or administered separately from the Fc construct. In some embodiments, the anti-cancer agent is joined (i.e., covalently conjugated) to the Fc construct and the conjugate is administered in methods of treating and/or protecting against cancer.

In some embodiments, Fc constructs described herein may be joined (i.e., covalently attached) to anti-cancer agents. One or more anti-cancer agents may be joined (i.e., covalently attached) to an Fc construct through chemical means, e.g., chemical conjugation. If desired, a spacer can be inserted between the Fc construct and the anti-cancer agent. In some embodiments, an anti-cancer agent is joined to the N-terminus or C-terminus (e.g., C-terminus) of one or more of the polypeptides of an Fc construct described herein (e.g., an Fc construct including 5-10 Fc domains (e.g., 5, 6, 7, 8, 9, or 10 Fc domains (e.g., 5 Fc domains))) by way of a linker.

The anti-cancer agent may be covalently conjugated to a polypeptide of the Fc construct by reaction of complementary functional groups on each species. The anti-cancer agent and/or the Fc construct may be functionalized to contain the complementary functional groups or the functional groups may be groups already present on the anti-cancer agent and/or the Fc construct. Examples of pairs of complementary functional groups include, but are not limited to, amine and carboxylic acid, thiol and maleimide, azide and alkyne, and alkene and tetrazine. The two functional groups can then react to through synthetic chemistry means to form a chemical bond, thus connecting the anti-cancer agent and the Fc construct together. Such chemical conjugation procedures are routine for those skilled in the art. For example, an amine functional group may be attached synthetically to an anti-cancer agent. The amine group on the anti-cancer agent may react with the carboxylic acid group at the C-terminus of a polypeptide of the Fc construct to form a conjugate of the Fc-construct and the anti-cancer agent.

Anti-cancer agents may be cancer antigens. A cancer antigen is an antigen that is expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. A cancer antigen may be associated with a specific type of tumor, such as a lymphoma, a carcinoma, a sarcoma, or a melanoma. A cancer antigen may elicit immune responses against the cancer (i.e., a cancerous tumor). Examples of cancer antigens include, but are not limited to, CD20, prostate-specific antigen (PSA), Her2, CD35, and vascular endothelial growth factor (VEGF). Other examples of cancer antigens include MART-1/Melan-A, gp100, adenosine deaminase-binding protein (ADAbp), FAP, cyclophilin b, colorectal associated antigen (CRC)-0017-1A/GA733, carcinoembryonic antigen (CEA), CAP-1, CAP-2, etv6, AML1, T cell receptor/CD3-zeta chain, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05, GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, a member of the mucin (MUC) family (e.g., MUC1), p21ras, RCAS1, α-fetoprotein, ε-cadherin, .α-catenin, β-catenin, γ-catenin, p120ctn, gp100.sup.Pme1117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus (HPV) proteins or peptides (e.g., HPV peptides as described above), Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, and c-erbB-2.

In some embodiments, an anti-cancer agent may be a fragment antigen-binding (Fab) domain, which recognizes and binds to antigens (e.g., cancer antigens). An Fc construct described herein, e.g., Fc constructs including 5-10 Fc domains (e.g., 5, 6, 7, 8, 9, or 10 Fc domains (e.g., 5 Fc domains)), may be joined (i.e., covalently conjugated) to a Fab domain. An Fc construct conjugated to a Fab domain may bind to an activating FcγR (e.g., FcγRI, FcγRIIa, FcγRIIc, FcγRIIIa, or FcγRIIIb) to induce destruction of cancer cells and/or tissues.

In some embodiments, an anti-cancer agent may be an agent that inhibits and/or down regulates the activity of a protein that prevents immune cell activation. Examples of such anti-cancer agents include, but are not limited to, an anti-PD-1 antibody (e.g., nivolumab, pembrolizumab), an anti-CTLA-4 (cytotoxic T-lymphocyte-associated protein 4) antibody, and an anti-LAG3 antibody.

Other examples of anti-cancer agents include, but are not limited to, alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammal I and calicheamicin omegall (see, e.g., Nicolaou et al. *Angew. Chem Intl. Ed. Engl.*, 33: 183-186 (1994)); CDP323, an oral alpha-4 integrin inhibitor; dynemicin, including dynemicin A; an esperamicin; neocarzinostatin chromophore and related chromoprotein enediyne antibiotic chromophores), aclacinomysins, actinomycin, authramycin, azaserine, bleomycin, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, 5-azacytidine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2', 2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™), and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPA-MUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

In some embodiments, an anti-cancer agent is cisplatin, carboplatin, oxaliplatin, bleomycin, mitomycin C, calicheamicins, maytansinoids, doxorubicin, idarubicin, daunorubicin, epirubicin, busulfan, carmustine, lomustine, semustine, methotrexate, 6-mercaptopurine, fludarabine, 5-azacytidine, pentostatin, cytarabine, gemcitabine, 5-fluorouracil, hydroxyurea, etoposide, teniposide, topotecan, irinotecan, chlorambucil, cyclophosphamide, ifosfamide, melphalan, bortezomib, vincristine, vinblastine, vinorelbine, paclitaxel, or docetaxel.

XII. Anti-Infective Agents

In some embodiments of the methods of the invention, anti-infective agents may be used in combination with Fc constructs including 5-10 Fc domains (e.g., 5, 6, 7, 8, 9, or 10 Fc domains (e.g., 5 Fc domains)). In some embodiments, the anti-infective agent is administered in addition to the Fc construct as a separate entity, i.e., the anti-infective agent is administered together (i.e., substantially simultaneously) with the Fc construct or administered separately from the Fc construct. In some embodiments, the anti-infective agent is joined (i.e., covalently conjugated) to the Fc construct and the conjugate is administered in methods of treating an infection.

In some embodiments, Fc constructs described herein may be joined (i.e., covalently conjugated) to anti-infective agents. One or more anti-infective agents may be joined (i.e., covalently conjugated) to an Fc construct through chemical means, e.g., chemical conjugation. If desired, a spacer can be inserted between the Fc construct and the anti-infective agent. In some embodiments, an anti-infective agent is joined to the N-terminus or C-terminus (e.g., C-terminus) of one or more of the polypeptides of an Fc construct described herein (e.g., an Fc construct including 5-10 Fc domains (e.g., 5, 6, 7, 8, 9, or 10 Fc domains (e.g., 5 Fc domains))) by way of a linker.

The anti-infective agent may be covalently conjugated to a polypeptide of the Fc construct by reaction of complementary functional groups on each species. The anti-infective agent and/or the Fc construct may be functionalized to contain the complementary functional groups or the functional groups may be groups already present on the anti-infective agent and/or the Fc construct. Examples of pairs of complementary functional groups include, but are not limited to, amine and carboxylic acid, thiol and maleimide, azide and alkyne, and alkene and tetrazine. The two functional groups can then react to through synthetic chemistry means to form a chemical bond, thus connecting the anti-infective agent and the Fc construct together. Such chemical conjugation procedures are routine for those skilled in the art. For example, an amine functional group may be attached synthetically to an anti-infective agent. The amine group on the anti-infective agent may react with the carboxylic acid group at the C-terminus of a polypeptide of the Fc construct to form a conjugate of the Fc-construct and the anti-infective agent.

An anti-infective agent may be an anti-bacterial agent, an anti-viral agent, an anti-fungal agent, an anti-helmintic agent, or an anti-protozoal agent. In some embodiments, the anti-infective agent is a microbial antigen. Examples of anti-bacterial agents include, but are not limited to, amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin clavulanate, ampicillin/sulbactam, piperacillin/tazobactam, ticarcillin/clavulanate, bacitracin, colistin, polymyxin b, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole (tmp-smx), sulfonamidochrysoidine, demeclocycline, doxycycline, minocycline, oxytetracycline, tetracycline, clofazimine, dapsone, capreomycin, cycloserine, ethambutol(bs), ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.

Examples of anti-viral agents include, but are not limited to, abacavir, aciclovir, acyclovir, adefovir, amantadine, amprenavir, ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, fusion inhibitor, ganciclovir, ibacitabine, imunovir, idoxuridine, imiquimod, indinavir, inosine, interferon type iii, interferon type ii, interferon type i, lamivudine, lopinavir, loviride, maraviroc, moroxydine, methisazone, nelfinavir, nevirapine, nexavir, nitazoxanide, novir, oseltamivir, peginterferon alfa-2a, penciclovir, peramivir, pleconaril, podophyllotoxin, raltegravir, ribavirin, rimantadine, ritonavir, pyramidine, saquinavir, sofosbuvir, stavudine, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Examples of anti-fungal agents include, but are not limited to, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, triazoles, albaconazole, efinaconazole, epoxiconazole, fluconazole, isavuconazole, itraconazole, posaconazole, propiconazole, ravuconazole, terconazole, voriconazole, thiazoles, abafungin, amorolfin, butenafine, naftifine, terbinafine, anidulafungin, caspofungin, micafungin, ciclopirox, flucytosine, griseofulvin, tolnaftate, and undecylenic acid.

Examples of anti-helmintic agents include, but are not limited to, albendazole, mebendazole, thiabendazole, fenbendazole, triclabendazole, flubendazole, abamectin, diethylcarbamazine, ivermectin, suramin, pyrantel pamoate, levamisole, niclosamide, oxyclozanide, praziquantel, octadepsipeptide, an aminoacetonitrile derivative, monepantel, spiroindole, derquantel, and pelletierine sulphate.

Examples of anti-protozoal agents include, but are not limited to, eflornithine, furazolidone, melarsoprol, metronidazole, ornidazole, paromomycin sulfate, pentamidine, pyrimethamine, tinidazole, and nifursemizone.

Examples of microbial antigens include, but are not limited to, a bacterial antigen, a fungal antigen, a parasitic antigen, or a viral antigen. in some embodiments, the bacterial antigen is an encapsulated bacterial antigen. In some embodiments, the antigen is selected from the group consisting of a *Streptococcus* antigen, a *Candida* antigen, a *Cryptococcus* antigen, a *Brucella* antigen, a *Salmonella* antigen, a *Staphylococcus* antigen, a *Porphyromonas* antigen, a *Burkholderia* antigen, a *Bacillus* antigen, a Mycobacteria antigen, a *Shigella* antigen, a *Pseudomonas* antigen, a *Bordetella* antigen, a *Clostridium* antigen, a Norwalk virus antigen, a *Bacillus anthracis* antigen, a *Mycobacterium tuberculosis* antigen, a human immunodeficiency virus (HIV) antigen, a *Chlamydia* antigen, a human Papillomavirus antigen, an Influenza virus antigen, a *Paramyxovirus* antigen, a Herpes virus antigen, a Cytomegalovirus antigen, a Varicella-Zoster virus antigen, an Epstein-Barr virus antigen, a Hepatitis virus antigen, a *Plasmodium* antigen, a *Trichomonas* antigen, a sexually transmitted disease antigen, an aerosol-transmitted disease antigen, a viral encephalitis disease antigen, a protozoal disease antigen, a fungal disease antigen, and a bacterial disease antigen.

XIII. Fc Constructs

In general, the invention features using Fc constructs having 5 or more Fc domains, e.g., 5-10 Fc domains (e.g., 5, 6, 7, 8, 9, or 10 Fc domains (e.g., 5 Fc domains)), in methods of inducing immune cell activation of the immune response in a subject, increasing phagocytosis of a target cell (i.e., a cancer cell or an infected cell) in a subject, or treating cancer or an infection in a subject. The Fc constructs having 5-10 Fc domains (e.g., 5, 6, 7, 8, 9, or 10 Fc domains (e.g., 5 Fc domains)) may have greater binding affinity and/or avidity than a single wild-type Fc domain for an Fc receptor. Amino acids at the interface of two interacting $C_H3$ antibody constant domains may be engineered such that the two Fc domain monomers of an Fc domain selectively form a dimer with each other, thus preventing the formation of unwanted multimers or aggregates. As shown in FIG. 1A, proteins generated from uncontrolled multimerization of tandem weight Fc domains display a wide ladder of species on SDS-PAGE, of which the target protein (100 kDa) is only a minor component. As shown in FIG. 1C, this random multimerization is avoided using the present constructs. In lanes 2-7 of the SDS-PAGE gel of FIG. 1C, a single, major protein band is evident with a molecular weight corresponding to each of the engineered Fc constructs (Fc1, Fc2, Fc3L, Fc3Y, Fc5X, or Fc5Y). Schematic representations of Fc construct Fc1, Fc2, Fc3L, Fc3Y, Fc5X, and Fc5Y are shown in FIG. 1B. In FIG. 1B, wild-type Fc $C_H2$ and $C_H3$ domains are labeled with "Wt;" $C_H3$ domains engineered with knobs and holes for heterodimerization are labeled with "kh;" and $C_H3$ domains engineered with homodimerizing electrostatic steering mutations are labeled with "es." An Fc construct includes an even number of Fc domain monomers, with each pair of Fc domain monomers forming an Fc domain. An Fc construct includes, at a minimum, one functional Fc domain formed from a dimer of two Fc domain monomers. In some embodiments, the Fc constructs described herein do not include an antigen-recognition region, e.g., a variable domain (e.g., $V_H$, $V_L$, a hypervariable region (HVR)) or a complementarity determining region (CDR). In some embodiments, the Fc constructs described herein include an antigen-recognition region, e.g., a variable domain (e.g., $V_H$, $V_L$, a HVR) or a CDR.

The Fc constructs described herein facilitate the preparation of homogenous pharmaceutical compositions. In some embodiments, the Fc constructs described herein facilitate the preparation of homogenous pharmaceutical compositions by incorporating structural features (for example, glycine spacers) that significantly improve manufacturing outcome.

Accordingly, the invention features pharmaceutical compositions that include a substantially homogenous population of an Fc construct described herein (e.g., an Fc construct having 5 or more Fc domains, e.g., 5-10 Fc domains (e.g., 5, 6, 7, 8, 9, or 10 Fc domains (e.g., 5 Fc domains))). Homogeneity is an important aspect of a pharmaceutical composition as it influences the pharmacokinetics and in vivo performance of the composition. Traditionally, in the manufacture of pharmaceutical products, there exists the problem of product heterogeneity that may be caused by several factors depending on how the product is produced. For example, the pharmaceutical product may undergo random product cleavage, proteolysis, degradation, and/or aggregation, off-target association of subunits, and/or inefficient protein folding. Different organisms having different biosynthetic processes or cellular machineries that are used to produce the pharmaceutical product may also cause heterogeneity in the product. Often, the initial culture containing the desired pharmaceutical product needs to undergo a rigorous purification process to produce a less heterogenous composition containing the pharmaceutical product.

In some embodiments, the Fc constructs described herein have structural features that significantly improve the folding efficiency of the Fc constructs and minimize off-target association of the subunits, thus, leading to pharmaceutical compositions containing these Fc constructs with high homogeneity. Having a high degree of homogeneity ensures the safety, efficacy, uniformity, and reliability of the pharmaceutical composition. Having a high degree of homogeneity also minimizes potential aggregation or degradation of the pharmaceutical product caused by unwanted materials (e.g., degradation products and/or aggregated products or multimers), as well as limiting off-target and adverse side effects caused by the unwanted materials.

As described in detail herein, the invention features substantially homogenous compositions containing Fc constructs that all have the same number of Fc domains, as well as methods of preparing such substantially homogenous compositions.

In some embodiments, the Fc constructs described herein include glycine spacers between Fc domains. As is well-known in the art, linkers containing both serines and glycines provide structural flexibility in a protein and are commonly used for joining two polypeptides. We have observed that linkers containing both serines and glycines undergo O-glycosylation (e.g., O-xylosylation) at multiple serines in the linker and proteolysis at the N-terminal side of serine. We aimed to optimize the linker sequence and length to further improve the homogeneity of the Fc constructs. We made Fc constructs in which all the linkers within the constructs are glycine spacers having only glycines (e.g., at least 12 glycines, e.g., 12-30 glycines; SEQ ID NO: 37 or 38). Having all glycine spacers in the Fc constructs further improved the homogeneity of the Fc constructs by removing O-glycosylation at serines and also decreasing the rate of proteolysis of the constructs. Consequently, we were able to achieve a more substantially homogenous population of Fc constructs by using all glycine spacers in the Fc constructs.

Homogeneity is the result of Fc construct components. For example, in a first approach ("approach (a)"), incorporation of linkers containing only glycines to join Fc domain monomers may be utilized. As we observed through experimentation, all-glycine spacers (e.g., at least 12 glycines, e.g., 12-30 glycines; SEQ ID NO: 37 or 38) in an Fc construct do not undergo O-glycosylation and are less susceptible to proteolysis as compared to traditional linkers that include serines and glycines.

In addition, in another approach ("approach (b)"), homogeneity of a composition containing an Fc construct described herein (e.g., an Fc construct having 5-10 Fc domains (e.g., 5 Fc domains)) is improved by removal of C-terminal lysines. Such C-terminal lysine residue are highly conserved in immunoglobulins across many species and may be fully or partially removed by the cellular machinery during protein production. Removal of the C-terminal lysines in the Fc constructs of the invention improves uniformity of the resulting composition and achieves a more homogenous Fc construct preparation. For example, in some embodiments of Fc constructs described herein (e.g., an Fc construct having 5-10 Fc domains (e.g., 5 Fc domains)), the codon of the C-terminal lysine is removed, thus, generating Fc constructs having polypeptides without C-terminal lysine residues and a resultant homogenous population.

A further approach ("approach (c)") to improve the homogeneity of a composition containing an Fc construct described herein (e.g., an Fc construct having five Fc domains), two sets of heterodimerizing selectivity modules were utilized: (i) heterodimerizing selectivity modules having different reverse charge mutations and (ii) heterodimerizing selectivity modules having engineered cavities and protuberances. We have observed through experimentation that when trying to form a heterodimeric Fc domain in an Fc construct, having both (i) and (ii) further improved the homogeneity of the pharmaceutical composition produced by reducing uncontrolled association of Fc domain monomers, and therefore undesirable oligomers and multimers. In particular examples, an Fc domain monomer containing (i) at least one reverse charge mutation and (ii) at least one engineered cavity or at least one engineered protuberance may be produced and will selectively combine with another Fc domain monomer containing (i) at least one reverse charge mutation and (ii) at least one engineered protuberance or at least one engineered cavity to form an Fc domain. In another example, an Fc domain monomer containing reversed charge mutation K370D and engineered cavities Y349C, T366S, L368A, and Y407V and another Fc domain monomer containing reversed charge mutation E357K and engineered protuberances S354C and T366W may be produced and will selectively combine to form an Fc domain.

As described in detail herein, a substantially homogenous composition containing an Fc construct of the invention (e.g., an Fc construct having 5-10 Fc domains (e.g., 5 Fc domains)) may be achieved by using all-glycine spacers between two Fc domain monomers in the Fc construct (approach (a)), by using polypeptides that lack C-terminal lysines in the Fc construct (approach (b)), and/or by using two sets of heterodimerizing selectivity modules ((i) heterodimerizing selectivity modules having different reverse charge mutations and (ii) heterodimerizing selectivity modules having engineered cavities and protuberances) to promote heterodimeric Fc domain formation by some Fc domain monomers in the Fc construct (approach (c)).

In some embodiments, a substantially homogenous composition containing an Fc construct described herein (e.g., an Fc construct having 5-10 Fc domains (e.g., 5 Fc domains)) may be achieved through approach (a).

In some embodiments, a substantially homogenous composition containing an Fc construct described herein (e.g., an Fc construct having 5-10 Fc domains (e.g., 5 Fc domains)) may be achieved through approach (b).

In some embodiments, a substantially homogenous composition containing an Fc construct described herein (e.g., an Fc construct having 5-10 Fc domains (e.g., 5 Fc domains)) may be achieved through approach (c).

In some embodiments, a substantially homogenous composition containing an Fc construct described herein (e.g., an Fc construct having 5-10 Fc domains (e.g., 5 Fc domains)) may be achieved through a combination of approaches (a) and (b).

In some embodiments, a substantially homogenous composition containing an Fc construct described herein (e.g., an Fc construct having 5-10 Fc domains (e.g., 5 Fc domains)) may be achieved through a combination of approaches (a) and (c).

In some embodiments, a substantially homogenous composition containing an Fc construct described herein (e.g., an Fc construct having 5-10 Fc domains (e.g., 5 Fc domains)) may be achieved through a combination of approaches (b) and (c).

In some embodiments, a substantially homogenous composition containing an Fc construct described herein (e.g., an Fc construct having 5-10 Fc domains (e.g., 5 Fc domains)) may be achieved through a combination of approaches (a), (b), and (c).

In some embodiments, to further improve the homogeneity of the pharmaceutical composition containing an Fc construct described herein, the N-terminal Asp in one or more of the polypeptides in the Fc construct in the composition is mutated to Gln. In some embodiments of a composition including a substantially homogenous population of an Fc construct described herein, the N-terminal Asp in each of the polypeptides in the Fc construct in the composition is mutated to Gln.

Furthermore, in Fc constructs of the invention (e.g., an Fc construct having 5-10 Fc domains (e.g., 5 Fc domains)), the length of the linkers that join Fc domain monomers influences the folding efficiency of the Fc constructs. In some embodiments, a linker having at least 4, 8, or 12 glycines (e.g., 4-30, 8-30, 12-30 glycines; SEQ ID NO: 37 or 38) may be used to join Fc domain monomers in Fc constructs of the invention.

Figure 5:
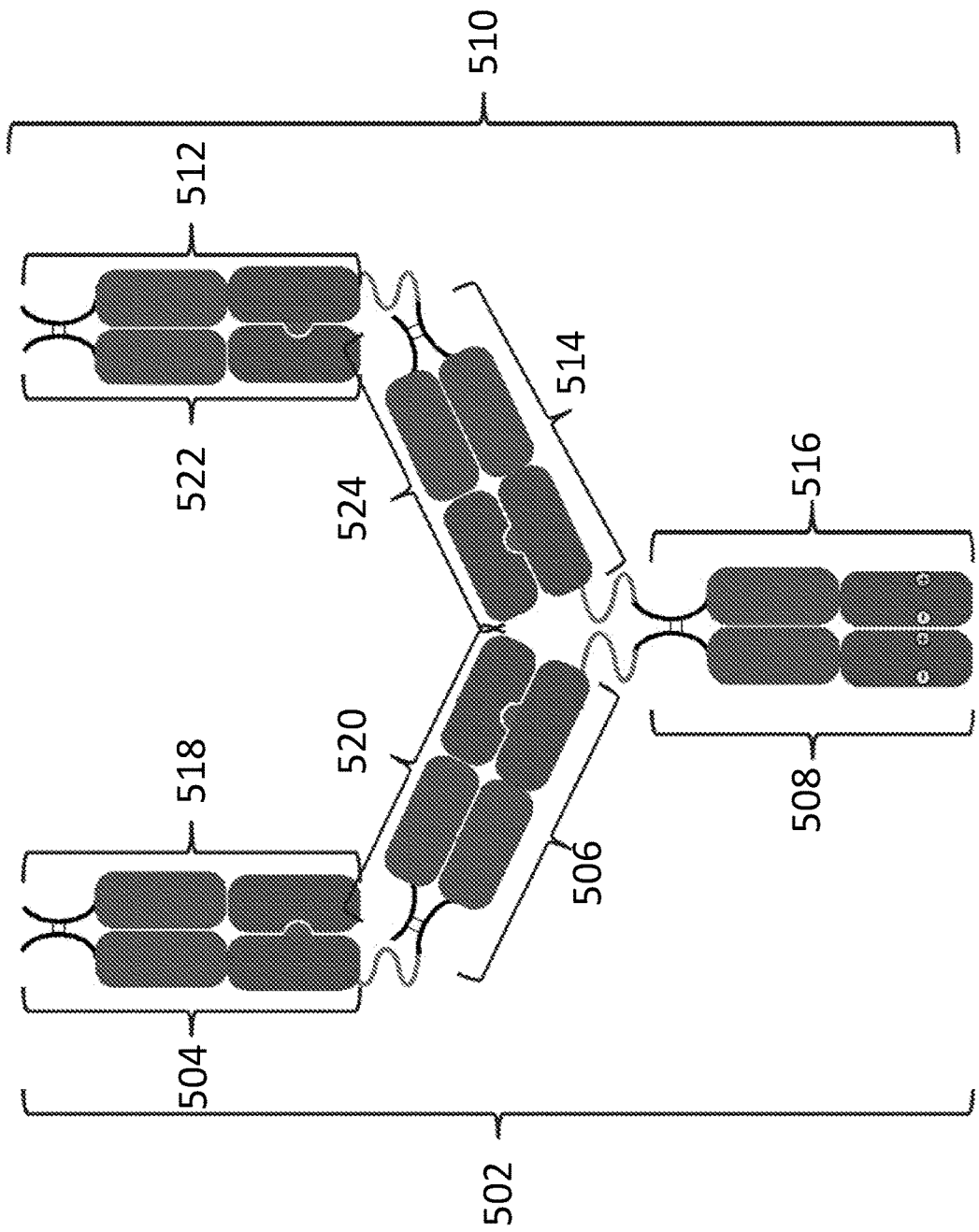
FIG. 5 is an illustration of an Fc construct containing five Fc domains formed from six polypeptides (Fc5Y). The first and second polypeptides (502 and 510) each contain three Fc domain monomers (504, 506, 508, and 512, 514, 516, respectively) joined in a tandem series. Specifically, in polypeptide 502 or 510, a first protuberance-containing Fc domain monomer (504 or 512) is connected to a second protuberance-containing Fc domain monomer (506 or 514), which is connected to a third Fc domain monomer containing different charged amino acids at the $C_H3$-$C_H3$ interface than the wild-type sequence (508 or 516). The third through sixth polypeptides (518, 520, 522, and 524) each contain a cavity-containing Fc domain monomer and form an Fc domain with each of Fc domain monomers 504, 506, 512, and 514, respectively.
Figure 6:
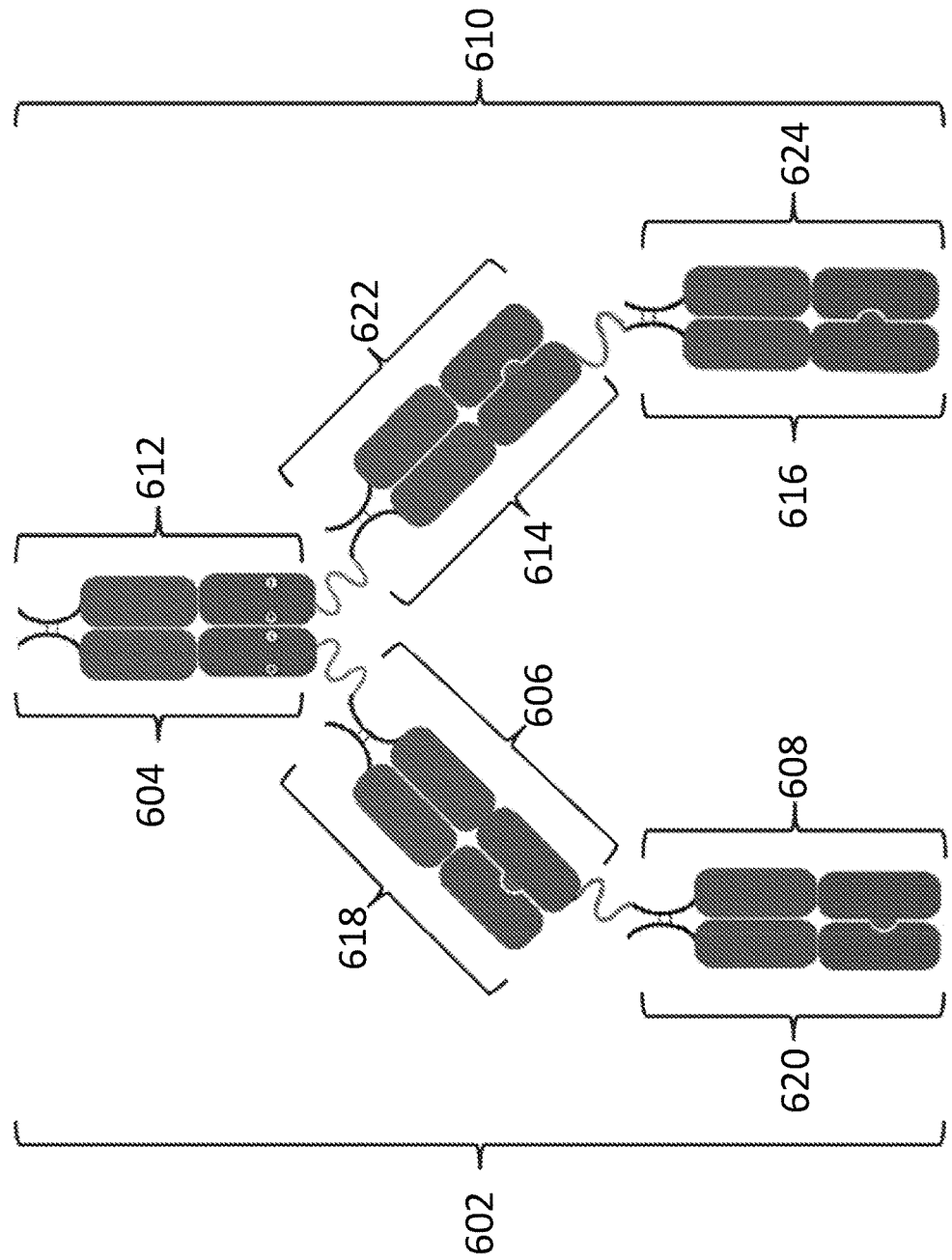
FIG. 6 is an illustration of an Fc construct containing five Fc domains formed from six polypeptides (Fc5Y-invert). The first and second polypeptides (602 and 610) each contain three Fc domain monomers (604, 606, 608, and 612, 614, 616, respectively) joined in a tandem series. Specifically, in polypeptide 602 or 610, a first Fc domain monomer containing different charged amino acids at the $C_H3$-$C_H3$ interface than the wild-type sequence (604 or 612) is connected to a second protuberance-containing Fc domain monomer (606 or 614), which is connected to a third protuberance-containing Fc domain monomer (608 or 616). The third through sixth polypeptides (618, 620, 622, and 624) each contain a cavity-containing Fc domain monomer and form an Fc domain with each of Fc domain monomers 606, 608, 614, and 616, respectively.

An Fc construct containing five Fc domains may form from six polypeptides (FIGS. 4-6). The first and second polypeptides (e.g., polypeptides 402 and 410 in FIG. 4; polypeptides 502 and 510 in FIG. 5; polypeptides 602 and 610 in FIG. 6) can be the same or different, as can the third, fourth, fifth, and sixth polypeptides (e.g., polypeptides 418, 420, 422, and 424 in FIG. 4; polypeptides 518, 520, 522, and 524 in FIG. 5; polypeptides 618, 620, 622, and 624 in FIG. 6).

In FIG. 4, the first and second polypeptides (402 and 410) each encodes three Fc domain monomers (e.g., Fc domain monomers 404, 406, and 408; Fc domain monomers 412, 414, and 416) connected by way of a linker in tandem series, wherein one Fc domain monomer contains charged amino acid substitutions in the $C_H3$ antibody constant domain (e.g., Fc domain monomers 406 and 414) while the other Fc domain monomer contains a protuberance in the $C_H3$ antibody constant domain (e.g., Fc domain monomers 404, 408, 412, and 416). The third, fourth, fifth, and sixth polypeptides each encodes an Fc domain monomer with a cavity (e.g., Fc domain monomers 418, 420, 422, and 424). A homodimeric Fc domain may be formed by combining Fc domain monomers 406 and 414, each of which contains the same reverse charge mutations in its $C_H3$ antibody constant domain (e.g., each of Fc domain monomers 406 and 414 contains D399K and K409D). A first heterodimeric Fc domain may be formed by combining Fc domain monomers 404 and 418 (e.g., Fc domain monomer 404 contains engineered protuberances S354C and T366W, and Fc domain monomer 418 contains engineered cavities Y349C, T366S, L368A, and Y409V). A second heterodimeric Fc domain may be formed by combining Fc domain monomers 408 and 420 (e.g., Fc domain monomer 408 contains engineered protuberances S354C and T366W, and Fc domain monomer 420 contains engineered cavities Y349C, T366S, L368A, and Y409V). A third heterodimeric Fc domain may be formed by combining Fc domain monomers 412 and 422 (e.g., Fc domain monomer 412 contains engineered protuberances S354C and T366W, and Fc domain monomer 422 contains engineered cavities Y349C, T366S, L368A, and Y409V). A fourth heterodimeric Fc domain may be formed by combining Fc domain monomers 416 and 424 (e.g., Fc domain monomer 416 contains engineered protuberances S354C and T366W, and Fc domain monomer 424 contains engineered cavities Y349C, T366S, L368A, and Y409V).

FIG. 5 is an illustration of an Fc construct containing five Fc domains formed from six polypeptides. The first and second polypeptides (502 and 510) each contain three Fc domain monomers (504, 506, 508, and 512, 514, 516, respectively) joined in a tandem series by way of a linker (e.g., a glycine spacer; SEQ ID NO: 37 or 38). Specifically, in polypeptide 502 or 510, a first protuberance-containing Fc domain monomer (504 or 512) is connected to a second protuberance-containing Fc domain monomer (506 or 514), which is connected to a third Fc domain monomer containing different charged amino acids at the $C_H3$-$C_H3$ interface (508 or 516) than the wild-type sequence. Fc domain monomers 508 and 516 may each contain the same reverse charge mutations (e.g., D399K/K409D) that promote formation of a homodimeric Fc domain. The third through sixth polypeptides (518, 520, 522, and 524) each contain a cavity-containing Fc domain monomer and form a heterodimeric Fc domain with each of Fc domain monomers 504, 506, 512 and 514, respectively. In some embodiments, each of the Fc domain monomers 504, 506, 512, 514, 518, 520, 522, and 524 may further contain reverse charge mutations to promote heterodimerization. For example, Fc domain monomer 504 having engineered protuberances and reverse charge mutations (e.g., E357K) may favorably form a heterodimeric Fc domain with Fc domain monomer 518 having engineered cavities and reverse charge mutations (e.g., K370D).

FIG. 6 is an illustration of another Fc construct containing five Fc domains formed from six polypeptides. The first and second polypeptides (602 and 610) each contain three Fc domain monomers (604, 606, 608, and 612, 614, 616, respectively) joined in a tandem series by way of a linker (e.g., a glycine spacer; SEQ ID NO: 37 or 38). Specifically, in polypeptide 602 or 610, a first Fc domain monomer containing different charged amino acids at the $C_H3$-$C_H3$ interface (604 or 612) than the wild-type sequence is connected to a second protuberance-containing Fc domain monomer (606 or 614), which is connected to a third protuberance-containing Fc domain monomer (608 or 616) than the wild-type sequence. Fc domain monomers 604 and 612 may each contain the same reverse charge mutations (e.g., D399K/K409D) that promote formation of a homodimeric Fc domain. The third through sixth polypeptides (618, 620, 622, and 624) each contain a cavity-containing Fc domain monomer and form a heterodimeric Fc domain with each of Fc domain monomers 606, 608, 614 and 616, respectively. In some embodiments, each of the Fc domain monomers 606, 608, 614, 616, 618, 620, 622, and 624 may further contain reverse charge mutations to promote heterodimerization. For example, Fc domain monomer 608 having engineered protuberances and reverse charge mutations (e.g., E357K) may favorably form a heterodimeric Fc domain with Fc domain monomer 620 having engineered cavities and reverse charge mutations (e.g., K370D).

In some embodiments, at least one of the first, second, third, fourth, fifth, and sixth Fc domains of any Fc construct of the invention includes an amino acid modification at position I253. In some embodiments, every one of the first, second, third, fourth, fifth, and sixth Fc domains includes an amino acid modification at position I253. In some embodiments, each of the amino acid modifications at position I253 is independently selected from the group consisting of I253A, I253C, I253D, I253E, I253F, I253G, I253H, I253I, I253K, I253L, I253M, I253N, I253P, I253Q, I253R, I253S, I253T, I253V, I253W, and I253Y. In some embodiments, each of the amino acid modifications at position I253 is independently I253A. In some embodiments, each of the amino acid modifications at position I253 is I253A. In some embodiments, the Fc construct includes at least one amino acid modification at position R292. In some embodiments, at least one of the first, second, third, fourth, fifth, and sixth Fc domains includes an amino acid modification at position R292. In some embodiments, every one of the first, second, third, fourth, fifth, and sixth Fc domains includes an amino acid modification at position R292. In some embodiments, each of the amino acid modifications at position R292 is independently selected from the group consisting of R292D, R292E, R292L, R292P, R292Q, R292R, R292T, and R292Y. In some embodiments, each of the amino acid modifications at position R292 is independently R292P. In some embodiments, each of the amino acid modifications at position R292 is R292P.

In some embodiments, at least one Fc domain of an Fc construct of the invention includes an amino acid modification at position I253 (e.g., I253A, I253C, I253D, I253E, I253F, I253G, I253H, I253I, I253K, I253L, I253M, I253N, I253P, I253Q, I253R, I253S, I253T, I253V, I253W, or I253Y) and/or at position R292 (e.g., R292P, R292D, R292E, R292L, R292Q, R292R, R292T, and R292Y). In some instances, at least one Fc domain includes an amino acid modification at position I253, e.g., I253A. In some instances, at least one Fc domain includes an amino acid modification at position R292, e.g., R292P. An Fc domain may include both an amino acid modification at position I253 (e.g., I253A) and at position R292 (e.g., R292P). For example, an Fc construct having five Fc domains may include an amino acid modification at position I253 (e.g., I253A) in one, two, three, four, or all five Fc domains and may additionally, or alternatively, include an amino acid modification at position R292 (e.g., R292P) in one, two, three, four, or all five Fc domains.

In some embodiments, Fc domain modifications that alter half-life may decrease the binding of a modified Fc domain to FcRn, for example, by modification of the Fc domain at position I253. Modifications at position I253 may include an amino acid substitution, wherein the amino acid at position I253 is substituted with a natural or non-natural amino acid; a deletion of the amino acid at position I253; or an insertion of one or more amino acid residues at position I253 of the Fc domain. Modification of amino acid I253 can be as part of a combination including multiple modifications (e.g., at other residue positions, e.g., R292), for example, a combination of one or more amino acid substitutions, deletions, and/or insertions. In particular embodiments, an Fc construct may contain, e.g., five Fc domains wherein at least one Fc domain contains a modification at position I253. For example, the wild-type amino acid residue, e.g., isoleucine (I), at position I253 may be substituted for a natural or non-natural amino acid, e.g., alanine (A). In some instances, each amino acid modification at position I253 is independently selected from, e.g., I253A, I253C, I253D, I253E, I253F, I253G, I253H, I253I, I253K, I253L, I253M, I253N, I253P, I253Q, I253R, I253S, I253T, I253V, I253W, and I253Y.

In other embodiments, Fc domain modifications that alter half-life may alter the binding of a modified Fc domain to FcγRIIb, for example, by modification of the Fc domain at position R292. Modifications at position R292 may include an amino acid substitution, wherein the amino acid at position R292 is substituted with a natural or non-natural amino acid; a deletion of the amino acid at position R292; or an insertion of one or more amino acid residues at position R292 of the Fc domain. Modification of amino acid 292 can be as part of a combination including multiple modifications (e.g., at other residue positions, e.g., I253), for example, a combination of one or more amino acid substitutions, deletions, and/or insertions. In particular embodiments, an Fc construct may contain, e.g., five Fc domains wherein at least one Fc domain contains a modification at position R292. For example, the wild-type amino acid residue, e.g., arginine (R), at position 292 may be substituted for a natural or non-natural amino acid, e.g., proline (P). In some instances, each amino acid modification at position R292 is independently selected from, e.g., R292P, R292D, R292E, R292L, R292Q, R292R, R292T, and R292Y.

In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer containing reversed charge mutation K370D and engineered cavities Y349C, T366S, L368A, and Y407V and another Fc domain monomer containing reversed charge mutation E357K and engineered protuberances S354C and T366W may selectively combine to form an Fc domain.

In some embodiments, one or more Fc polypeptides in an Fc construct (e.g., Fc constructs in FIGS. 4-6) lack a C-terminal lysine residue. In some embodiments, all of the Fc polypeptides in an Fc construct lack a C-terminal lysine residue. In some embodiments, the absence of a C-terminal lysine in one or more Fc polypeptides in an Fc construct may improve the homogeneity of a population of an Fc construct (e.g., an Fc construct having 5-10 Fc domains (e.g., 5 Fc domains)), e.g., a population of an Fc construct having five Fc domains that is substantially homogeneous. In one example, the C-terminal lysine residue in an Fc polypeptide having the sequence of any one of SEQ ID NOs: 40, 43, 44, and 46 may be removed to generate a corresponding Fc polypeptide that does not contain a C-terminal lysine residue.

In some embodiments, the N-terminal Asp in one or more of the polypeptides in an Fc construct described herein (e.g., polypeptides 402, 410, 418, 420, 422, and 424 in FIG. 4; 502, 510, 518, 520, 522, and 524 in FIG. 5; 602, 610, 618, 620, 622, and 624 in FIG. 6) may be mutated to Gln. In some embodiments, the N-terminal Asp in each of the polypeptides in an Fc construct described herein is mutated to Gln. In other embodiments, an Fc construct described herein (e.g., an Fc construct having five Fc domains) may include one or more Fc domain monomers having N-terminal Asp be mutated to Gln. In some embodiments, the mutation of N-terminal Asp to Gln in one or more of the polypeptides in an Fc construct described herein may improve the homogeneity of a population of an Fc construct (e.g., an Fc construct having five Fc domains), e.g., a population of an Fc construct having five Fc domains that is substantially homogeneous.

In some embodiments, Fc constructs can contain five Fc domains formed from six polypeptides. Three examples are depicted in FIGS. 4-6. While these depicted Fc constructs each includes six polypeptides, four of the polypeptides can be encoded by the same nucleic acid, and the remaining two polypeptides can also be encoded by the same nucleic acid. As a result, these Fc constructs can be produced by the expression of two nucleic acids in a suitable host cell.

In some embodiments, in an Fc construct including: a) a first polypeptide having the formula A-L1-B-L2-C; wherein i) A includes a first Fc domain monomer; ii) L1 is a linker; iii) B includes a second Fc domain monomer; iv) L2 is a linker; and v) C includes a third Fc domain monomer; b) a second polypeptide having the formula A'-L1'-B'-L2'-C'; wherein i) A' includes a fourth Fc domain monomer; ii) L1' is a linker; iii) B' includes a fifth Fc domain monomer; iv) L2' is a linker; and v) C' includes a sixth Fc domain monomer; c) a third polypeptide that includes a seventh Fc domain monomer; d) a fourth polypeptide that includes an eighth Fc domain monomer; e) a fifth polypeptide that includes a ninth Fc domain monomer; and f) a sixth polypeptide that includes a tenth Fc domain monomer; wherein A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain. Examples of some amino acid mutations that can be incorporated into the Fc domain monomers in the Fc construct are shown in Tables 3A-3D. In some embodiments, each of the first, second, third, fourth, fifth, and sixth polypeptides in the Fc construct lacks a C-terminal lysine. In some embodiments, the N-terminal Asp in each of the first, second, third, fourth, fifth, and sixth polypeptides in the Fc construct is mutated to Gln. In some embodiments, each of L1, L2, L1', and L2' has the sequence GGGGGGGGGGGGGGGGGGGG (SEQ ID NO: 38).

TABLE 3A

| Fc domain monomer | Amino acid mutations (each column represents a set of mutations in an Fc construct having five Fc domains) | | | | | | | | |
|---|---|---|---|---|---|---|---|---|---|
| A, C, A', and C' | Engineered protuberance reversed charge mutation(s) | S354C T366W E357K | S354C T366W E357R | S354C T366W E357K | S354C T366W E357K | S354C T366W E357R | S354C T366W E357R | S354C T366W E357K | S354C T366W E357R |
| L1, L2, L1', and L2' | | GGGGGGGGGGGGGGGGGGGG (SEQ ID NO: 38) | | | | | | | |
| B and B' | reversed charge mutation(s) | D399K K409D | D399K K409D | D399R K409D | D399K K409E | D399R K409D | D399K K409E | D399R K409E | D399R K409E |
| 7th, 8th, 9th, and 10th Fc domain monomers | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | K370D | K370D | K370D | K370D | K370D | K370D | K370D | K370D |

| Fc domain monomer | Amino acid mutations (each column represents a set of mutations in an Fc construct having five Fc domains) | | | | | | | |
|---|---|---|---|---|---|---|---|---|
| A, C, A', and C' | S354C T366W E357K | S354C T366W E357R | S354C T366W E357K | S354C T366W E357K | S354C T366W E357R | S354C T366W E357R | S354C T366W E357K | S354C T366W E357R |
| L1, L2, L1', and L2' | GGGGGGGGGGGGGGGGGGGG (SEQ ID NO: 38) | | | | | | | |
| B and B' | D399K K409D | D399K K409D | D399R K409D | D399K K409E | D399R K409D | D399K K409E | D399R K409E | D399R K409E |
| 7th, 8th, 9th, and 10th Fc domain monomers | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E | Y349C T366S L368A Y407V K370E |

TABLE 3B

| Fc domain monomer | Amino acid mutations (each column represents a set of mutations in an Fc construct having five Fc domains) | | | | | | | | |
|---|---|---|---|---|---|---|---|---|---|
| A, C, A', and C' | Engineered protuberance reversed charge mutation(s) | S354C T366W K370D | S354C T366W K370D | S354C T366W K370D | S354C T366W K370D | S354C T366W K370D | S354C T366W K370D | S354C T366W K370D | S354C T366W K370D |
| L1, L2, L1', and L2' | | GGGGGGGGGGGGGGGGGGGG (SEQ ID NO: 38) | | | | | | | |
| B and B' | reversed charge mutation(s) | D399K K409D | D399K K409D | D399R K409D | D399K K409E | D399R K409D | D399K K409E | D399R K409E | D399R K409E |
| 7th, 8th, 9th, and 10th Fc domain monomers | Engineered cavity | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V | Y349C T366S L368A Y407V |
| | reversed charge mutation(s) | E357K | E357R | E357K | E357K | E357R | E357R | E357K | E357R |

TABLE 3B-continued

| Fc domain monomer | Amino acid mutations (each column represents a set of mutations in an Fc construct having five Fc domains) | | | | | | | |
|---|---|---|---|---|---|---|---|---|
| A, C, A', and C' | S354C T366W K370E | S354C T366W K370E | S354C T366W K370E | S354C T366W K370E | S354C T366W K370E | S354C T366W K370E | S354C T366W K370E | S354C T366W K370E |
| L1, L2, L1', and L2' | GGGGGGGGGGGGGGGGGGGG (SEQ ID NO: 38) | | | | | | | |
| B and B' | D399K K409D | D399K K409D | D399R K409D | D399K K409E | D399R K409D | D399K K409E | D399R K409E | D399R K409E |
| 7$^{th}$, 8$^{th}$, 9$^{th}$, and 10$^{th}$ Fc domain monomers | Y349C T366S L368A Y407V E357K | Y349C T366S L368A Y407V E357R | Y349C T366S L368A Y407V E357K | Y349C T366S L368A Y407V E357K | Y349C T366S L368A Y407V E357R | Y349C T366S L368A Y407V E357R | Y349C T366S L368A Y407V E357K | Y349C T366S L368A Y407V E357R |

TABLE 3C

| Fc domain monomer | | Amino acid mutations (each column represents a set of mutations in an Fc construct having five Fc domains) | | | | | | | |
|---|---|---|---|---|---|---|---|---|---|
| A, C, A', and C' | Engineered cavity reversed charge mutation(s) | Y349C T366S L368A Y407V E357K | Y349C T366S L368A Y407V E357R | Y349C T366S L368A Y407V E357K | Y349C T366S L368A Y407V E357K | Y349C T366S L368A Y407V E357R | Y349C T366S L368A Y407V E357R | Y349C T366S L368A Y407V E357K | Y349C T366S L368A Y407V E357R |
| L1, L2, L1', and L2' | | GGGGGGGGGGGGGGGGGGGG (SEQ ID NO: 38) | | | | | | | |
| B and B' | reversed charge mutation(s) | D399K K409D | D399K K409D | D399R K409D | D399K K409E | D399R K409D | D399K K409E | D399R K409E | D399R K409E |
| 7$^{th}$, 8$^{th}$, 9$^{th}$ and 10$^{th}$ Fc domain monomers | Engineered protuberance reversed charge mutation(s) | S354C T366W K370D | S354C T366W K370D | S354C T366W K370D | S354C T366W K370D | S354C T366W K370D | S354C T366W K370D | S354C T366W K370D | S354C T366W K370D |

| Fc domain monomer | Amino acid mutations (each column represents a set of mutations in an Fc construct having five Fc domains) | | | | | | | |
|---|---|---|---|---|---|---|---|---|
| A, C, A', and C' | Y349C T366S L368A Y407V E357K | Y349C T366S L368A Y407V E357R | Y349C T366S L368A Y407V E357K | Y349C T366S L368A Y407V E357K | Y349C T366S L368A Y407V E357R | Y349C T366S L368A Y407V E357R | Y349C T366S L368A Y407V E357K | Y349C T366S L368A Y407V E357R |
| L1, L2, L1', and L2' | GGGGGGGGGGGGGGGGGGGG (SEQ ID NO: 38) | | | | | | | |
| B and B' | D399K K409D | D399K K409D | D399R K409D | D399K K409E | D399R K409D | D399K K409E | D399R K409E | D399R K409E |
| 7$^{th}$, 8$^{th}$, 9$^{th}$ and 10$^{th}$ Fc domain monomers | S354C T366W K370E | S354C T366W K370E | S354C T366W K370E | S354C T366W K370E | S354C T366W K370E | S354C T366W K370E | S354C T366W K370E | S354C T366W K370E |

TABLE 3D

| Fc domain monomer | | Amino acid mutations (each column represents a set of mutations in an Fc construct having five Fc domains) | | | | | | | |
|---|---|---|---|---|---|---|---|---|---|
| A, C, A', and C' | Engineered cavity | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V |
| | reversed charge mutation(s) | K370D | K370D | K370D | K370D | K370D | K370D | K370D | K370D |
| L1, L2, L1', and L2' | | GGGGGGGGGGGGGGGGGGGG (SEQ ID NO: 38) | | | | | | | |
| B and B' | reversed charge mutation(s) | D399K<br>K409D | D399K<br>K409D | D399R<br>K409D | D399K<br>K409E | D399R<br>K409D | D399K<br>K409E | D399R<br>K409E | D399R<br>K409E |
| 7th, 8th, 9th and 10th Fc domain monomers | Engineered protuberance reversed charge mutation(s) | S354C<br>T366W<br>E357K | S354C<br>T366W<br>E357R | S354C<br>T366W<br>E357K | S354C<br>T366W<br>E357K | S354C<br>T366W<br>E357R | S354C<br>T366W<br>E357R | S354C<br>T366W<br>E357K | S354C<br>T366W<br>E357R |

| Fc domain monomer | Amino acid mutations (each column represents a set of mutations in an Fc construct having five Fc domains) | | | | | | | |
|---|---|---|---|---|---|---|---|---|
| A, C, A', and C' | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E |
| L1, L2, L1', and L2' | GGGGGGGGGGGGGGGGGGGG (SEQ ID NO: 38) | | | | | | | |
| B and B' | D399K<br>K409D | D399K<br>K409D | D399R<br>K409D | D399K<br>K409E | D399R<br>K409D | D399K<br>K409E | D399R<br>K409E | D399R<br>K409E |
| 7th, 8th, 9th and 10th Fc domain monomers | S354C<br>T366W<br>E357K | S354C<br>T366W<br>E357R | S354C<br>T366W<br>E357K | S354C<br>T366W<br>E357K | S354C<br>T366W<br>E357R | S354C<br>T366W<br>E357R | S354C<br>T366W<br>E357K | S354C<br>T366W<br>E357R |

Table 4 below provides exemplary sequences of the Fc polypeptides in the Fc construct shown in FIGS. 4, 5, and 6.

| Fc polypeptide | Amino Acid Sequence |
|---|---|
| | Fc construct in FIG. 4 |
| 402/410 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDKLTKNQVSLWCLVKGFYPSDIAVEWESNGQPENNY<br>KTIPPVLDSDGSFFLYSKLTVDKSRWQQGNVFSCSVMHEALHNHYTQKSLSLSPGK<br>GGGGGGGGGGGGGGGGGGGGDKTHTCPPCPAPELLGGPSVFLFPPKPKDTLMISR<br>TPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQVSLTCLV<br>KGFYPSDIAVEWESNGQPENNYKTTPPVLKSDGSFFLYSDLTVDKSRWQQGNVFSC<br>SVMHEALHNHYTQKSLSLSPGKGGGGGGGGGGGGGGGGGGGGDKTHTCPPCPAP<br>ELLGGPSVFLFPPKPKDILMISRTPEVICVVVDVSHEDPEVKFNWYVDGVEVHNAKT<br>KPREEQYNSTYRVVSVLTVLHQDWLNGKEYKCKVSNKALPAPIEKTISKAKGQPREP<br>QVYTLPPCRDKLTKNQVSLWCLVKGFYPSDIAVEWESNGQPENNYKTTPPVLDSDGS<br>FFLYSKLTVDKSRWQQGNVFSCSVMHEALHNHYTQKSLSLSPG<br>(SEQ ID NO: 47) |
| 418/420/422/424 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVDGFYPSDIAVEWESNGQPENNY<br>KTIPPVLDSDGSFFLVSKLTVDKSRWQQGNVFSCSVMHEALHNHYTQKSLSLSPG<br>(SEQ ID NO: 42) |

| Fc polypeptide | Amino Acid Sequence |
|---|---|
| Fc construct in FIG. 5 | |
| 502/510 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDKLTKNQVSLWCLVKGFYPSDIAVEWESNGQPENNY<br>KTIPPVLDSDGSFFLYSKLTVDKSRWQQGNVFSCSVMHEALHNHYTQKSLSLSPGK<br>GGGGGGGGGGGGGGGGGGGDKTHTCPPCPAPELLGGPSVFLFPPKPKDTLMISR<br>TPEVTCVVVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPCRDKLTKNQVSLWCL<br>VKGFYPSDIAVEWESNGQPENNYKTTPPVLDSDGSFFLYSKLTVDKSRWQQGNVFS<br>CSVMHEALHNHYTQKSLSLSPGKGGGGGGGGGGGGGGGGGGGDKTHTCPPCPA<br>PELLGGPSVFLFPPKPKDILMISRTPEVICVVVDVSHEDPEVKFNWYVDGVEVHNAK<br>TKPREEQYNSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPPVLKSDGS<br>FFLYSDLTVDKSRWQQGNVFSCSVMHEALHNHYTQKSLSLSPG<br>(SEQ ID NO: 48) |
| 518/520/522/524 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVDGFYPSDIAVEWESNGQPENNY<br>KTIPPVLDSDGSFFLVSKLTVDKSRWQQGNVFSCSVMHEALHNHYTQKSLSLSPG<br>(SEQ ID NO: 42) |
| Fc construct in FIG. 6 | |
| 602/610 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPSRDELTKNQVSLICLVKGFYPSDIAVEVVESNGQPENNY<br>KTTPPVLKSDGSFFLYSDLTVDKSRWQQGNVFSCSVMHEALHNHYTQKSLSLSPGK<br>GGGGGGGGGGGGGGGGGGGDKTHTCPPCPAPELLGGPSVFLFPPKPKDTLMISR<br>TPEVTCVVVDVSHEDPEVKFNVVYVDGVEVHNAKTKPREEQYNSTYRVVSVLTVLHQ<br>DWLNGKEYKCKVSNKALPAPIEKTISKAKGQPREPQVYTLPPCRDKLTKNQVSLWCL<br>VKGFYPSDIAVEWESNGQPENNYKTTPPVLDSDGSFFLYSKLTVDKSRWQQGNVFS<br>CSVMHEALHNHYTQKSLSLSPGKGGGGGGGGGGGGGGGGGGGDKTHTCPPCPA<br>PELLGGPSVFLFPPKPKDILMISRTPEVICVVVDVSHEDPEVKFNVVYVDGVEVHNAK<br>TKPREEQYNSTYRVVSVLTVLHQDWLNGKEYKCKVSNKALPAPIEKTISKAKGQPREP<br>QVYTLPPCRDKLIKNQVSLWCLVKGFYPSDIAVEVVESNGQPENNYKTTPPVLDSDGS<br>FFLYSKLTVDKSRWQQGNVFSCSVMHEALHNHYTQKSLSLSPG<br>(SEQ ID NO: 49) |
| 618/620/622/624 | DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVDGFYPSDIAVEWESNGQPENNY<br>KTTPPVLDSDGSFFLVSKLTVDKSRWQQGNVFSCSVMHEALHNHYTQKSLSLSPG<br>(SEQ ID NO: 42) |

In some embodiments, one or more Fc polypeptides in an Fc construct (e.g., Fc constructs in FIGS. 4-6) lack a C-terminal lysine residue. In some embodiments, all of the Fc polypeptides in an Fc construct lack a C-terminal lysine residue. In some embodiments, the absence of a C-terminal lysine in one or more Fc polypeptides in an Fc construct may improve the homogeneity of a population of an Fc construct (e.g., an Fc construct having five Fc domains), e.g., a population of an Fc construct having five Fc domains that is substantially homogeneous.

In some embodiments, an Fc domain monomer in an Fc construct described herein (e.g., an Fc construct having five Fc domains) may have a sequence that is at least 95% identical (e.g., at least 97%, 99%, or 99.5% identical) to the sequence of a wild-type Fc domain monomer (e.g., SEQ ID NO: 39). In some embodiments, an Fc domain monomer in an Fc construct described herein (e.g., an Fc construct having five Fc domains) may have a sequence that is at least 95% identical (e.g., at least 97%, 99%, or 99.5% identical) to the sequence of any one of SEQ ID NOs: 40-46. In certain embodiments, an Fc domain monomer in the Fc construct may have a sequence that is at least 95% identical (e.g., at least 97%, 99%, or 99.5% identical) to the sequence of SEQ ID NO: 42, 45, and 46.

In some embodiments, a polypeptide having three Fc domain monomers in an Fc construct described herein (e.g., polypeptides 402 and 410 in FIG. 4; polypeptides 502 and 510 in FIG. 5; polypeptides 602 and 610 in FIG. 6) may have a sequence that is at least 95% identical (e.g., at least 97%, 99%, or 99.5% identical) to the sequence of any one of SEQ ID NOs: 47-49. In certain embodiments, a polypeptide having three Fc domain monomers in an Fc construct described herein may have a sequence that is at least 95% identical (e.g., at least 97%, 99%, or 99.5% identical) to the sequence of SEQ ID NOs: 47. In some embodiments, the amino acid mutations in a polypeptide having three Fc domain monomers in an Fc construct described herein (e.g., polypeptides 402 and 410 in FIG. 4; polypeptides 502 and 510 in FIG. 5; polypeptides 602 and 610 in FIG. 6) occur only in the Fc domain monomers and do not occur in the spacer.

In some embodiments, the N-terminal Asp in one or more of the first, second, third, fourth, fifth, and sixth polypeptides in an Fc construct described herein (e.g., polypeptides 402, 410, 418, 420, 422, and 424 in FIG. 4; polypeptides 502, 510, 518, 520, 522, and 524 in FIG. 5; polypeptides 602, 610, 618, 620, 622, and 624 in FIG. 6) may be mutated to Gln. In some embodiments, the N-terminal Asp in each of the first, second, third, fourth, fifth, and sixth polypeptides in an Fc construct described herein is mutated to Gln. In other embodiments, an Fc construct described herein (e.g., an Fc construct having five Fc domains) may include one or more Fc domain monomers having N-terminal Asp be mutated to Gln. In some embodiments, the mutation of N-terminal Asp to Gln in one or more of the first, second, third, fourth, fifth, and sixth polypeptides in an Fc construct described herein may improve the homogeneity of a population of an Fc construct (e.g., an Fc construct having five Fc domains), e.g., a population of an Fc construct having five Fc domains that is substantially homogeneous.

XIV. Host Cells and Protein Production

In the present invention, a host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (transformation, transfection, electroporation, calcium phosphate precipitation, direct microinjection, etc.). Host cells can be of mammalian, bacterial origin, fungal, or insect. Mammalian host cells include, but are not limited to, CHO (or CHO-derived cell strains, e.g., CHO-K1, CHO-DXB11 CHO-DG44), murine host cells (e.g., NS0, Sp2/0), VERY, HEK (e.g., HEK293), BHK, HeLa, COS, MDCK, 293, 3T3, W138, BT483, Hs578T, HTB2, BT20 and T47D, CRL7030 and HsS78Bst cells. Host cells can also be chosen that modulate the expression of the protein constructs, or modify and process the protein product in the specific fashion desired. Different host cells have characteristic and specific mechanisms for the post-translational processing and modification of protein products. Appropriate cell lines or host systems can be chosen to ensure the correct modification and processing of the protein expressed.

For expression and secretion of protein products from their corresponding DNA plasmid constructs, host cells may be transfected or transformed with DNA controlled by appropriate expression control elements known in the art, including promoter, enhancer, sequences, transcription terminators, polyadenylation sites, and selectable markers. Methods for expression of therapeutic proteins are known in the art. See, for example, Paulina Balbas, Argelia Lorence (eds.) *Recombinant Gene Expression: Reviews and Protocols (Methods in Molecular Biology)*, Humana Press; 2nd ed. 2004 edition (Jul. 20, 2004); Vladimir Voynov and Justin A. Caravella (eds.) *Therapeutic Proteins: Methods and Protocols (Methods in Molecular Biology)* Humana Press; 2nd ed. 2012 edition (Jun. 28, 2012).

XV. Purification

An Fc construct can be purified by any method known in the art of protein purification, for example, by chromatography (e.g., ion exchange, affinity (e.g., Protein A affinity), and size-exclusion column chromatography), centrifugation, differential solubility, or by any other standard technique for the purification of proteins. For example, an Fc construct can be isolated and purified by appropriately selecting and combining affinity columns such as Protein A column with chromatography columns, filtration, ultra-filtration, and/or salting-out and dialysis procedures (see, e.g., *Process Scale Purification of Antibodies*, Uwe Gottschalk (ed.) John Wiley & Sons, Inc., 2009; and Subramanian (ed.) *Antibodies—Volume I—Production and Purification*, Kluwer Academic/Plenum Publishers, New York (2004)).

In some instances, an Fc construct can be conjugated to one or more purification peptides to facilitate purification and isolation of the Fc construct from, e.g., a whole cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct include, but are not limited to, a hexa-histidine peptide, a FLAG peptide, a myc peptide, and a hemagglutinin (HA) peptide. A hexa-histidine peptide (HHHHHH (SEQ ID NO: 26)) binds to nickel-functionalized agarose affinity column with micromolar affinity. In some embodiments, a FLAG peptide includes the sequence DYKDDDDK (SEQ ID NO: 27). In some embodiments, a FLAG peptide includes integer multiples of the sequence DYKDDDDK in tandem series, e.g., 3xDYKDDDDK. In some embodiments, a myc peptide includes the sequence EQKLISEEDL (SEQ ID NO: 28). In some embodiments, a myc peptide includes integer multiples of the sequence EQKLISEEDL in tandem series, e.g., 3xEQKLISEEDL. In some embodiments, an HA peptide includes the sequence YPYDVPDYA (SEQ ID NO: 29). In some embodiments, an HA peptide includes integer multiples of the sequence YPYDVPDYA in tandem series, e.g., 3xYPYDVPDYA. Antibodies that specifically recognize and bind to the FLAG, myc, or HA purification peptide are well-known in the art and often commercially available. A solid support (e.g., a matrix, a resin, or agarose beads) functionalized with these antibodies may be used to purify an Fc construct that includes a FLAG, myc, or HA peptide.

For the Fc constructs, as an alternative or adjunct method, Protein A column chromatography may be employed as a purification process. Protein A ligands interact with Fc constructs through the Fc region, making Protein A chromatography a highly selective capture process that is able to remove most of the host cell proteins. In the present invention, Fc constructs may be purified using Protein A column chromatography.

XVI. Pharmaceutical Compositions/Preparations

Fc constructs having 5-10 Fc domains (e.g., 5, 6, 7, 8, 9, or 10 Fc domains (e.g., 5 Fc domains)) may be formulated in a pharmaceutical composition for use in the methods described herein. In one embodiment, a pharmaceutical composition includes a substantially homogenous population of Fc constructs that are identical or substantially identical in structure. In various examples, the pharmaceutical composition includes a substantially homogenous population of Fc constructs, e.g., Fc constructs having 5-10 Fc domains (e.g., 5 Fc domains; Fc5X (FIG. 4); Fc5Y (FIG. 5); or Fc5Y-invert (FIG. 6)). In some embodiments, Fc constructs having 5-10 Fc domains (e.g., 5, 6, 7, 8, 9, or 10 Fc domains (e.g., 5 Fc domains)) may be formulated in a pharmaceutical composition alone. In some embodiments, Fc constructs having 5-10 Fc domains (e.g., 5, 6, 7, 8, 9, or 10 Fc domains (e.g., 5 Fc domains)) may be formulated in combination with an anti-cancer agent in a pharmaceutical composition. In some embodiments, Fc constructs having 5-10 Fc domains (e.g., 5, 6, 7, 8, 9, or 10 Fc domains (e.g., 5 Fc domains)) may be formulated in combination with an anti-infective agent in a pharmaceutical composition.

A therapeutic protein construct, e.g., an Fc construct having 5-10 Fc domains (e.g., 5, 6, 7, 8, 9, or 10 Fc domains (e.g., 5 Fc domains)), can be incorporated into a pharmaceutical composition, either alone, or in combination with an anti-cancer agent or an anti-infective agent. Pharmaceutical compositions including therapeutic proteins can be formulated by methods know to those skilled in the art. The pharmaceutical composition can be administered parenterally in the form of an injectable formulation including a sterile solution or suspension in water or another pharmaceutically acceptable liquid. For example, the pharmaceutical composition can be formulated by suitably combining the Fc construct with pharmaceutically acceptable vehicles or media, such as sterile water for injection (WFI), physiological saline, emulsifier, suspension agent, surfactant, stabilizer, diluent, binder, excipient, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50, and the like commonly known in the art. Formulation methods for therapeutic protein products are known in the art, see e.g., Banga (ed.) *Therapeutic Peptides and Proteins: Formulation, Processing and Delivery Systems* (2d ed.) Taylor & Francis Group, CRC Press (2006).

XVII. Dosage

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, oral dosage forms such as ingestible solutions and drug release capsules. The appropriate dosage for the individual subject depends on the therapeutic objectives, the route of administration, and the condition of the subject. Generally, recombinant proteins are dosed at 1-200 mg/kg, e.g., 1-100 mg/kg, e.g., 20-100 mg/kg. Accordingly, it will be necessary for a healthcare provider to tailor and titer the dosage and modify the route of administration as required to obtain the optimal therapeutic effect.

EXAMPLES

Example 1—Experimental Methods

Fc Construct Production

Genes were subcloned into the pcDNA3.4 A_357 mammalian expression vector (ThermoFisher Scientific). Plasmids were transfected into EXP1293 cells (ThermoFisher Scientific) according to the manufacturer's instructions with minor modifications. EXP1293 cells were grown to a density of $4.5$-$6.0\times10^6$ cells/mL in EXP1293 media at 8% $CO_2$. Immediately prior to transfection, cultures were diluted to $3\times10^6$ cells/mL with fresh EXP1293 media. For transfection, plasmid DNA and ExpiFectamine (ThermoFisher Scientific) transfection reagent were diluted in EXP1293 media. At 14-20 h post-transfection ExpiFectamine enhancers 1 and 2 were added to the cultures. On the next day, transfected cells were supplemented with an additional 20% volume of fresh EXP1293 media. Typically, cultures were maintained for 8 days unless cell viability dropped below 50%. Cells were removed from media by centrifugation at 15,900×g for 30 min. Media supernatant was clarified and sterilized by sequential passage through 0.45 m and 0.22 nm cellulose acetate filters. Samples were purified by protein A capture (POROS MabCapture A, ThermoFisher Scientific), followed by cation exchange (Poros XS, ThermoFisher Scientific) to removed high and low MW variants assembled from the same polypeptide chains as the target molecule. Samples were exchanged into PBS.

SDS-PAGE

Media supernatants and purified Fc constructs were denatured for 10 min at 95° C. in the presence of Laemmli buffer (Bio-Rad, Hercules, CA). Samples were separated on 4%-15% TGX stain-free acrylamide pre-cast gels (Bio-Rad) using the Bio-Rad Criterion gel electrophoresis vertical cell following the manufacturer's instructions. Proteins were visualized by either rapid fluorescent detection or by staining with Coomassie R-250 brilliant blue stain (Bio-Rad). Images were acquired with the ChemiDoc MP imaging system (Bio-Rad).

Analytical Size Exclusion Chromatography (SEC)

Samples were analyzed at 1 mg/mL concentration on an Agilent 1200 system (Agilent Technologies, Santa Clara, CA) using a Zenix-C 4.6×300 mm 3 m particle size column (Sepax Technologies, Newark, DE) at an isocratic flow of 0.35 mL/min with 150 mM sodium phosphate (pH 7.0) as the running buffer and column thermostated to 30° C. The total run time was around 12-15 min with UV detection at 280 nm. The totally excluded volume was at approximately 4 min.

Capillary Electrophoresis-Sodium Dodecyl Sulfate (CE-SDS) Assay

Samples at 1 mg/mL were mixed with the denaturing buffer supplied in the HT Protein Express Reagent kit (PerkinElmer, Waltham, MA). The mixture was heated at 40° C. for 20 min. Samples were transferred to a 96-well plate after adding 70 μL of water and then injected on a Caliper GXII instrument (PerkinElmer) equipped with the HT Protein Express LabChip (PerkinElmer). The relative abundance of each size variant was calculated based on fluorescence intensity.

Cell-Based FcγR Binding

Relative binding of Fc constructs and controls to FcγRs were measured using cell-based homogeneous time-resolved fluorescence (HTRF) competition assays (Cisbio Bioassays, Bedford, MA). Kits used were CD16aV158 Cat. 62C16PAG, CD16aF158 Cat. 6FR3APAg, CD32aR131 Cat. 6FRARPAG, CD32aH131 Cat. 6FRAHPAG, CD32b Cat. 6FR2BPAG, and CD64 Cat. 6FC64PAG. Assay reagents were prepared according to the manufacturer's instructions. To prepare dilution plates, the highest sample concentrations to be used were prepared manually in Tag-Lite buffer (Cisbio Bioassays) in a 96-well plate. A 10-point, 3-fold serial dilution series, plus one blank per sample, was generated using an automated liquid handler (Freedom EVOware 150, Tecan, Morrisville, NC). Assay plates were prepared by the liquid handler at room temperature in white, 384-well, flat-bottomed plates (Sigma-Aldrich). Assay plates were read on a PHERAstar fluorescent reader (BMG Labtech GmbH, Ortenberg, Germany) at 665 and 620 nm. Each sample concentration was X log-transformed and plotted against its respective HTRF signal ratio (665 nm/620 nm). A four-parameter nonlinear regression analysis (least squares fit) was performed on the XY-plot to calculate $IC_{50}$ of the unlabeled sample, with IC50 being inversely proportional to the sample's affinity for FcγR.

Immunoblot Detection of Phosphorylated Proteins in Primary Monocytes

Primary monocytes ($3 \times 10^5$ cells/well, 96-well plate) were stimulated with 100 μg/mL IVIg, or IgG1 (goat IgG and rabbit anti goat IgG, 285 μg/mL), or an Fc construct for 10 min at 37° C. Cells were lysed, and samples were resolved on SDS-PAGE and transferred to nitrocellulose membrane. Membranes were stained for phosphorylated and total Syk (Cell Signaling 2710S, EMD Millipore, Billerica, MA), Aid (Cell Signaling 4060S and 2920, EMD Millipore), and Erk1/2 (Cell Signaling 4370S and 4696, EMD Millipore). Membranes were scanned and densitometry measured using Odyssey CLx (LI-COR, Lincoln, NB).

Calcium Influx in Primary Monocytes $1.5 \times 10^5$ primary monocytes (suspended 1:2 Roswell Park Memorial Institute medium [RPMI]+1% bovine serum albumin [BSA]: calcium 4 dye) were plated in clear-bottom poly-D-lysine 96-well plates. The cells were treated with IgG1 (285 μg/mL), or IVIg (100 μg/mL), or an Fc construct and fluorescence (ex. 485 nm, em. 525 nm) was measured using a FlexStation 3 Microplate Reader (Molecular Devices, Sunnyvale, CA). Baseline was recorded for 20 s before test compounds were added; upon stimulation, measurements were acquired every 2 s for 3 min. Maximum response achieved over 3 min was normalized to the baseline and plotted as relative fluorescence units (Max-Min).

Figure 1E:
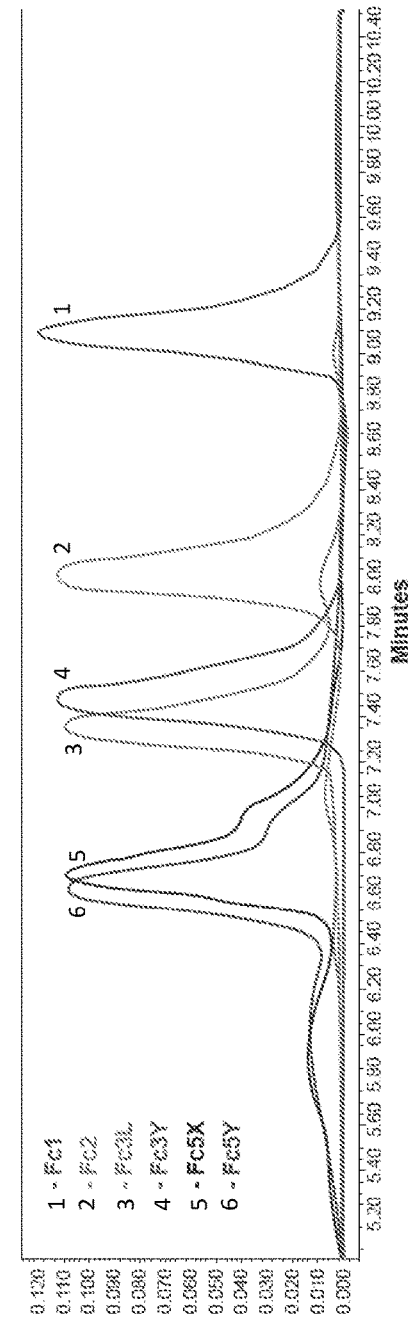
FIG. 1E shows a size-exclusion chromatograph (SEC) analysis of Fc constructs Fc1, Fc2, Fc3L, Fc3Y, Fc5X, and Fc5Y.

Example 2—Fc Constructs with Discrete Sizes Define the Threshold for Cellular Activation To define the specific threshold for activation of FcγRs, a panel of Fc constructs of discrete sizes and configurations was engineered. Obtaining discrete MWs required the use of mutations to control the manner in which peptide subunits assemble to form Fc domains as constructs that contain multiple wild-type Fc domains produce ladders of high MW oligomers through uncontrolled association (FIG. 1A). Two approaches were adopted to control Fc configurations assembled from hetero-oligomerization of peptide chains. First, the peptide sequences were encoded on separate plasmids, allowing control over the expression of each individual construct. Then mutations were incorporated into the Fc domains that favored either heterodimerization or homodimerization, based on knobs-into-holes or electrostatic steering approaches, respectively. The judicious placement of homodimerizing and heterodimerizing Fc domain subunits within the constructs permitted controlled assembly of Fc constructs with different sizes and configurations (Fc constructs Fc1, Fc2, Fc3L, Fc3Y, Fc5X, and Fc5Y; FIG. 1B). The resulting Fc constructs are denoted as Fc2, Fc3, or Fc5 to indicate the number of Fc domains each contains (2, 3, or 5, respectively); branching differences are denoted by an additional letter as indicated in FIG. 1B. In FIG. 1B, wild-type Fc $C_H2$ and $C_H3$ domains are labeled with "wt;" $C_H3$ domains engineered with knobs and holes for heterodimerization are labeled with "kh;" and $C_H3$ domains engineered with homodimerizing electrostatic steering mutations are labeled with "es." Non-reducing sodium dodecyl sulfate polyacrylamide gel electrophoresis demonstrated that each sample was primarily composed of an Fc construct of the anticipated MW (FIG. 1C). Additional analytical measurements confirmed that the expected species were generated (FIGS. 1D and 1E). FIG. 1D shows that capillary electrophoresis-SDS (CE-SDS) analysis of Fc constructs Fc1, Fc2, Fc3L, Fc3Y, Fc5X, and Fc5Y confirms the size distributions of these Fc constructs determined by the non-reducing SDS-PAGE in FIG. 1C. FIG. 1E shows that size-exclusion chromatography (SEC) analysis of Fc constructs Fc1, Fc2, Fc3L, Fc3Y, Fc5X, and Fc5Y also confirms the size distributions of these Fc constructs measured by the non-reducing SDS-PAGE in FIG. 1C. FIG. 1E also demonstrates that these Fc constructs contain little non-covalent aggregation. Note that the retention time in SEC is inversely proportional to the size of the molecule, so Fc constructs elute in the order: Fc5<Fc3<Fc2<Fc1.

Figure 2A:
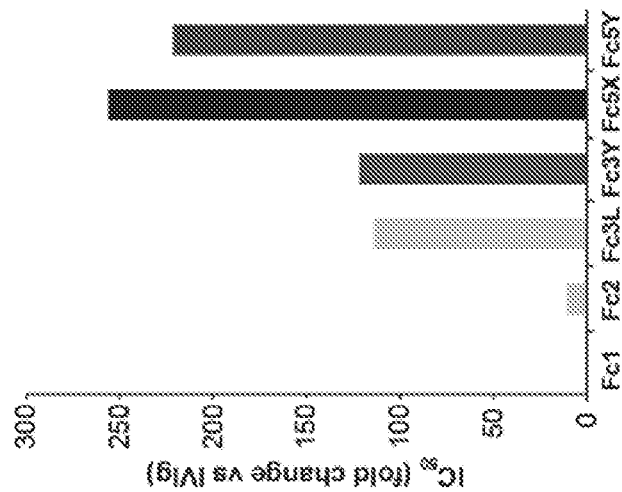
FIG. 2A shows the relative binding of Fc constructs Fc1, Fc2, Fc3L, Fc3Y, Fc5X, and Fc5Y to FcγRIIa-H131 using the time-resolved fluorescence resonance energy transfer competitive binding assay.

The binding of these engineered Fc constructs to FcγRIIa, the principal low affinity FcγR in monocytes, was determined by a cell-based, time-resolved fluorescence resonance energy transfer competitive binding assay (FIG. 2A). The Fc constructs displayed greatly enhanced binding to all FcγRs (FcγRI, FcγRIIa-H131, FcγRIIa-R131, FcγRIIb, FcγRIIIa-F158, and FcγRIIIa-V158) compared with IVIg, with $IC_{50}$ being dependent on the number of Fc domains (FIG. 2B). Binding could not be compared between different receptors due to differential expression of FcγRs.

Figure 3A:
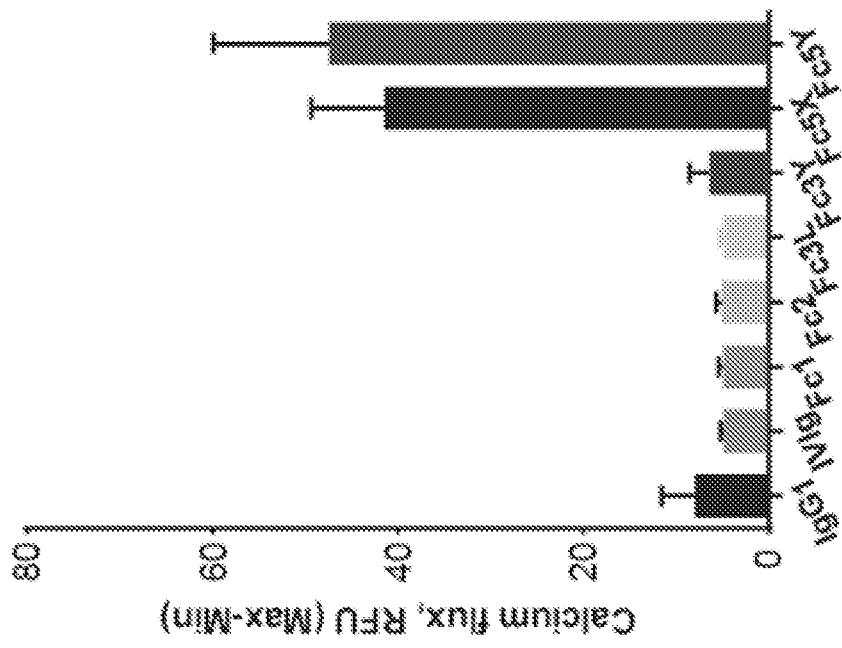
FIG. 3A shows the induction of Syk phosphorylation in THP-1 monocytes by Fc constructs Fc1, Fc2, Fc3L, Fc3Y, Fc5X, and Fc5Y as measured by immunoblotting.
Figure 3B:
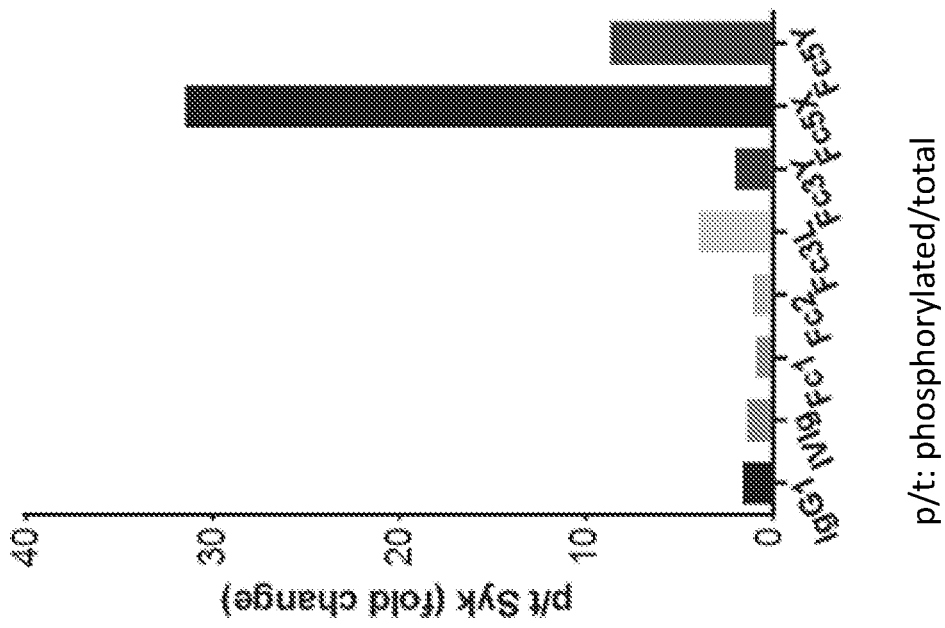
FIG. 3B shows the induction of calcium flux in primary monocytes by Fc constructs Fc1, Fc2, Fc3L, Fc3Y, Fc5X, and Fc5Y.

Interestingly, despite the significant increase in FcγR binding, Fc3L and Fc3Y behaved similarly to the IgG1 isotype control, IVIg, Fc1, and Fc2L in monocyte activation assays. Fc3L and Fc3Y neither induced Syk phosphorylation in THP-1 monocytes (FIG. 3A) nor calcium flux in primary monocytes (FIG. 3B). In contrast, the Fc5X and Fc5Y pentamers dramatically increased pSyk formation (FIG. 3A) and calcium flux (FIG. 3B). Furthermore, differences in the configuration of Fc domain linkages were noted, with Fc5X inducing a greater fold change in pSyk formation compared with that of Fc5Y (FIG. 3A).

Figure 3C:
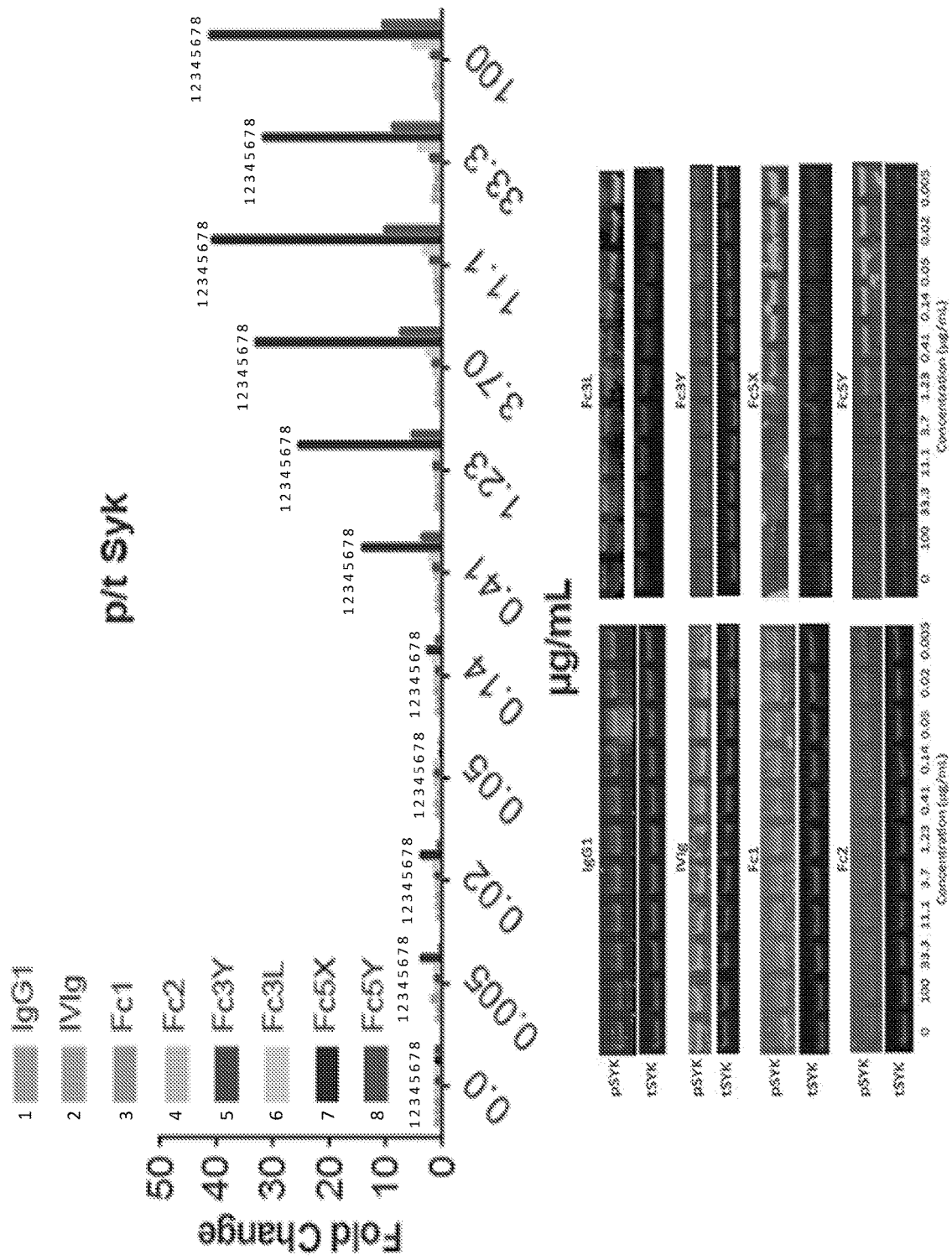
FIG. 3C shows the dose-dependent induction of Syk phosphorylation in THP-1 monocytes by Fc constructs Fc1, Fc2, Fc3L, Fc3Y, Fc5X, and Fc5Y as measured by immunoblotting.
Figure 3D:
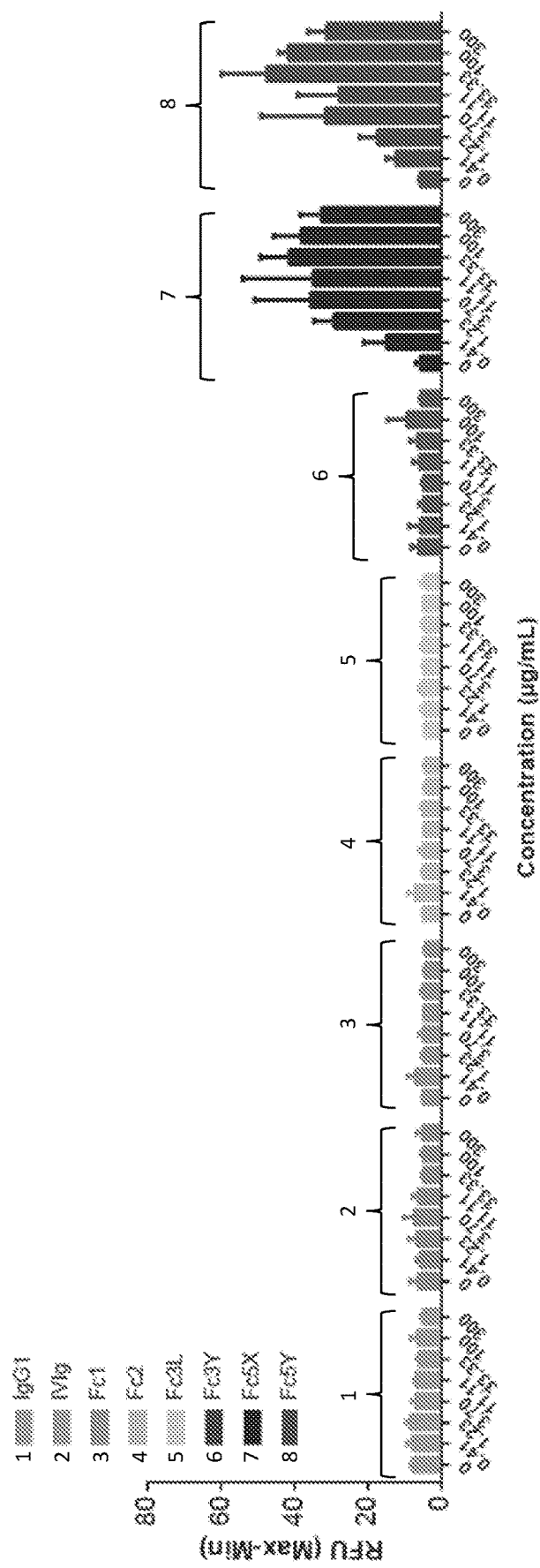
FIG. 3D shows the dose-dependent induction of calcium flux in primary monocytes by Fc constructs Fc1, Fc2, Fc3L, Fc3Y, Fc5X, and Fc5Y.

Fc5X and Fc5Y induction of Syk phosphorylation and calcium flux were potent and dose-dependent, inducing signals at concentrations as low as 0.41 μg/mL (FIG. 3C). Conversely, Fc2, Fc3L, and Fc3Y did not significantly increase pSyk or calcium flux at doses ranging from 0.005 to 300 μg/mL (FIG. 3D).

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety.

Other embodiments are within the following claims.

```
                          SEQUENCE LISTING

<160> NUMBER OF SEQ ID NOS: 49

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Gly Gly Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic construct

<400> SEQUENCE: 2

Gly Gly Ser Gly
1

<210> SEQ ID NO 3
<211> LENGTH: 4
<212> TYPE: PRT
<213> ORGANISM: Artificial Sequence
<220> FEATURE:
<223> OTHER INFORMATION: synthetic construct

<400> SEQUENCE: 3

Ser Gly Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: synthetic construct

<400> SEQUENCE: 4

Gly Ser Gly Ser
1

<210> SEQ ID NO 5
<211> LENGTH: 6
<212> TYPE: PRT
<213> ORGANISM: Artificial Sequence
<220> FEATURE:
<223> OTHER INFORMATION: synthetic construct

<400> SEQUENCE: 5

Gly Ser Gly Ser Gly Ser
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic construct

<400> SEQUENCE: 6
```

```
Gly Ser Gly Ser Gly Ser Gly Ser
1               5

<210> SEQ ID NO 7
<211> LENGTH: 10
<212> TYPE: PRT
<213> ORGANISM: Artificial Sequence
<220> FEATURE:
<223> OTHER INFORMATION: synthetic construct

<400> SEQUENCE: 7

Gly Ser Gly Ser Gly Ser Gly Ser Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic construct

<400> SEQUENCE: 8

Gly Ser Gly Ser Gly Ser Gly Ser Gly Ser Gly Ser
1               5                   10

<210> SEQ ID NO 9
<211> LENGTH: 6
<212> TYPE: PRT
<213> ORGANISM: Artificial Sequence
<220> FEATURE:
<223> OTHER INFORMATION: synthetic construct

<400> SEQUENCE: 9

Gly Gly Ser Gly Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic construct

<400> SEQUENCE: 10

Gly Gly Ser Gly Gly Ser Gly Gly Ser
1               5

<210> SEQ ID NO 11
<211> LENGTH: 12
<212> TYPE: PRT
<213> ORGANISM: Artificial Sequence
<220> FEATURE:
<223> OTHER INFORMATION: synthetic construct

<400> SEQUENCE: 11

Gly Gly Ser Gly Gly Ser Gly Gly Ser Gly Gly Ser
1               5                   10

<210> SEQ ID NO 12
<211> LENGTH: 8
<212> TYPE: PRT
<213> ORGANISM: Artificial Sequence
<220> FEATURE:
<223> OTHER INFORMATION: synthetic construct

<400> SEQUENCE: 12

Gly Gly Ser Gly Gly Gly Ser Gly
```

```
<210> SEQ ID NO 13
<211> LENGTH: 12
<212> TYPE: PRT
<213> ORGANISM: Artificial Sequence
<220> FEATURE:
<223> OTHER INFORMATION: synthetic construct

<400> SEQUENCE: 13

Gly Gly Ser Gly Gly Gly Ser Gly Gly Gly Ser Gly
1               5                   10

<210> SEQ ID NO 14
<211> LENGTH: 15
<212> TYPE: PRT
<213> ORGANISM: Artificial Sequence
<220> FEATURE:
<223> OTHER INFORMATION: synthetic construct

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: synthetic construct

<400> SEQUENCE: 15

Gly Glu Asn Leu Tyr Phe Gln Ser Gly Gly
1               5                   10

<210> SEQ ID NO 16
<211> LENGTH: 8
<212> TYPE: PRT
<213> ORGANISM: Artificial Sequence
<220> FEATURE:
<223> OTHER INFORMATION: synthetic construct

<400> SEQUENCE: 16

Ser Ala Cys Tyr Cys Glu Leu Ser
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic construct

<400> SEQUENCE: 17

Arg Ser Ile Ala Thr
1               5

<210> SEQ ID NO 18
<211> LENGTH: 17
<212> TYPE: PRT
<213> ORGANISM: Artificial Sequence
<220> FEATURE:
<223> OTHER INFORMATION: synthetic construct

<400> SEQUENCE: 18

Arg Pro Ala Cys Lys Ile Pro Asn Asp Leu Lys Gln Lys Val Met Asn
1               5                   10                  15
```

His

<210> SEQ ID NO 19
<211> LENGTH: 36
<212> TYPE: PRT
<213> ORGANISM: Artificial Sequence
<220> FEATURE:
<223> OTHER INFORMATION: synthetic construct

<400> SEQUENCE: 19

```
Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35
```

<210> SEQ ID NO 20
<211> LENGTH: 17
<212> TYPE: PRT
<213> ORGANISM: Artificial Sequence
<220> FEATURE:
<223> OTHER INFORMATION: synthetic construct

<400> SEQUENCE: 20

```
Ala Ala Ala Asn Ser Ser Ile Asp Leu Ile Ser Val Pro Val Asp Ser
1               5                   10                  15

Arg
```

<210> SEQ ID NO 21
<211> LENGTH: 36
<212> TYPE: PRT
<213> ORGANISM: Artificial Sequence
<220> FEATURE:
<223> OTHER INFORMATION: synthetic construct

<400> SEQUENCE: 21

```
Gly Gly Ser Gly Gly Gly Ser Glu Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35
```

<210> SEQ ID NO 22
<211> LENGTH: 12
<212> TYPE: PRT
<213> ORGANISM: Artificial Sequence
<220> FEATURE:
<223> OTHER INFORMATION: synthetic construct

<400> SEQUENCE: 22

```
Gly Gly Gly Ser Gly Gly Gly Ser Gly Gly Gly Ser
1               5                   10
```

<210> SEQ ID NO 23
<211> LENGTH: 18
<212> TYPE: PRT
<213> ORGANISM: Artificial Sequence
<220> FEATURE:
<223> OTHER INFORMATION: synthetic construct

<400> SEQUENCE: 23

```
Gly Gly Ser Gly Gly Gly Ser Gly Gly Gly Ser Gly Gly Gly Ser Gly
1               5                   10                  15

Gly Ser

<210> SEQ ID NO 24
<211> LENGTH: 20
<212> TYPE: PRT
<213> ORGANISM: Artificial Sequence
<220> FEATURE:
<223> OTHER INFORMATION: synthetic construct

<400> SEQUENCE: 24

Ser Gly Gly Gly Ser Gly Gly Gly Ser Gly Gly Ser Gly Gly Gly
1               5                   10                  15

Ser Gly Gly Gly
            20

<210> SEQ ID NO 25
<211> LENGTH: 11
<212> TYPE: PRT
<213> ORGANISM: Artificial Sequence
<220> FEATURE:
<223> OTHER INFORMATION: synthetic construct

<400> SEQUENCE: 25

Asp Ile Cys Leu Pro Arg Trp Gly Cys Leu Trp
1               5                   10

<210> SEQ ID NO 26
<211> LENGTH: 6
<212> TYPE: PRT
<213> ORGANISM: Artificial Sequence
<220> FEATURE:
<223> OTHER INFORMATION: synthetic construct

<400> SEQUENCE: 26

His His His His His His
1               5

<210> SEQ ID NO 27
<211> LENGTH: 8
<212> TYPE: PRT
<213> ORGANISM: Artificial Sequence
<220> FEATURE:
<223> OTHER INFORMATION: synthetic construct

<400> SEQUENCE: 27

Asp Tyr Lys Asp Asp Asp Asp Lys
1               5

<210> SEQ ID NO 28
<211> LENGTH: 10
<212> TYPE: PRT
<213> ORGANISM: Artificial Sequence
<220> FEATURE:
<223> OTHER INFORMATION: synthetic construct

<400> SEQUENCE: 28

Glu Gln Lys Leu Ile Ser Glu Glu Asp Leu
1               5                   10

<210> SEQ ID NO 29
<211> LENGTH: 9
<212> TYPE: PRT
<213> ORGANISM: Artificial Sequence
<220> FEATURE:
```

<223> OTHER INFORMATION: synthetic construct

<400> SEQUENCE: 29

Tyr Pro Tyr Asp Val Pro Asp Tyr Ala
1               5

<210> SEQ ID NO 30
<211> LENGTH: 4
<212> TYPE: PRT
<213> ORGANISM: Artificial Sequence
<220> FEATURE:
<223> OTHER INFORMATION: synthetic construct

<400> SEQUENCE: 30

Gly Gly Gly Gly
1

<210> SEQ ID NO 31
<211> LENGTH: 8
<212> TYPE: PRT
<213> ORGANISM: Artificial Sequence
<220> FEATURE:
<223> OTHER INFORMATION: synthetic construct

<400> SEQUENCE: 31

Gly Gly Gly Gly Gly Gly Gly Gly
1               5

<210> SEQ ID NO 32
<211> LENGTH: 12
<212> TYPE: PRT
<213> ORGANISM: Artificial Sequence
<220> FEATURE:
<223> OTHER INFORMATION: synthetic construct

<400> SEQUENCE: 32

Gly Gly Gly Gly Gly Gly Gly Gly Gly Gly Gly Gly
1               5                   10

<210> SEQ ID NO 33
<211> LENGTH: 16
<212> TYPE: PRT
<213> ORGANISM: Artificial Sequence
<220> FEATURE:
<223> OTHER INFORMATION: synthetic construct

<400> SEQUENCE: 33

Gly Gly Gly Gly Gly Gly Gly Gly Gly Gly Gly Gly Gly Gly Gly Gly
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: synthetic construct

<400> SEQUENCE: 34

Gly Gly Gly Gly Gly Gly Gly Gly Gly Gly Gly Gly Gly Gly Gly Gly
1               5                   10                  15

Gly Gly Gly Gly
            20

<210> SEQ ID NO 35
<211> LENGTH: 5
<212> TYPE: PRT

```
<213> ORGANISM: Artificial Sequence
<220> FEATURE:
<223> OTHER INFORMATION: synthetic construct

<400> SEQUENCE: 35

Gly Gly Gly Gly Gly
1               5

<210> SEQ ID NO 36
<211> LENGTH: 10
<212> TYPE: PRT
<213> ORGANISM: Artificial Sequence
<220> FEATURE:
<223> OTHER INFORMATION: synthetic construct

<400> SEQUENCE: 36

Gly Gly Gly Gly Gly Gly Gly Gly Gly Gly
1               5                   10

<210> SEQ ID NO 37
<211> LENGTH: 15
<212> TYPE: PRT
<213> ORGANISM: Artificial Sequence
<220> FEATURE:
<223> OTHER INFORMATION: synthetic construct

<400> SEQUENCE: 37

Gly Gly Gly Gly Gly Gly Gly Gly Gly Gly Gly Gly Gly Gly Gly
1               5                   10                  15

<210> SEQ ID NO 38
<211> LENGTH: 20
<212> TYPE: PRT
<213> ORGANISM: Artificial Sequence
<220> FEATURE:
<223> OTHER INFORMATION: synthetic construct

<400> SEQUENCE: 38

Gly Gly Gly Gly Gly Gly Gly Gly Gly Gly Gly Gly Gly Gly Gly
1               5                   10                  15

Gly Gly Gly Gly
            20

<210> SEQ ID NO 39
<211> LENGTH: 227
<212> TYPE: PRT
<213> ORGANISM: Homo sapiens

<400> SEQUENCE: 39

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 40
<211> LENGTH: 227
<212> TYPE: PRT
<213> ORGANISM: Artificial Sequence
<220> FEATURE:
<223> OTHER INFORMATION: synthetic construct

<400> SEQUENCE: 40

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225
```

<210> SEQ ID NO 41
<211> LENGTH: 226
<212> TYPE: PRT
<213> ORGANISM: Artificial Sequence
<220> FEATURE:
<223> OTHER INFORMATION: synthetic construct

<400> SEQUENCE: 41

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 42
<211> LENGTH: 226
<212> TYPE: PRT
<213> ORGANISM: Artificial Sequence
<220> FEATURE:
<223> OTHER INFORMATION: synthetic construct

<400> SEQUENCE: 42

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
```

Arg Val Val Ser Val Leu Thr Val Leu His Gln Asp Trp Leu Asn Gly
65                  70                  75                  80
                    85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Cys Thr Leu Pro Pro Ser Arg Asp Glu Leu Thr Lys Asn Gln Val Ser
        130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 43
<211> LENGTH: 227
<212> TYPE: PRT
<213> ORGANISM: Artificial Sequence
<220> FEATURE:
<223> OTHER INFORMATION: synthetic construct

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met

```
                195             200             205
His Glu Ala Leu His Asn His Tyr Thr Gln Lys Ser Leu Ser Leu Ser
    210                 215                 220

Pro Gly Lys
225

<210> SEQ ID NO 44
<211> LENGTH: 227
<212> TYPE: PRT
<213> ORGANISM: Artificial Sequence
<220> FEATURE:
<223> OTHER INFORMATION: synthetic construct

<400> SEQUENCE: 44

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 45
<211> LENGTH: 226
<212> TYPE: PRT
<213> ORGANISM: Artificial Sequence
<220> FEATURE:
<223> OTHER INFORMATION: synthetic construct

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
       130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 46
<211> LENGTH: 227
<212> TYPE: PRT
<213> ORGANISM: Artificial Sequence
<220> FEATURE:
<223> OTHER INFORMATION: synthetic construct

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Lys Leu Thr Lys Asn Gln Val Ser
       130                 135                 140

Leu Trp Cys Leu Val Lys Gly Phe Tyr Pro Ser Asp Ile Ala Val Glu
145                 150                 155                 160
```

Trp Glu Ser Asn Gly Gln Pro Glu Asn Asn Tyr Lys Thr Thr Pro Pro
              165                 170                 175

Val Leu Asp Ser Asp Gly Ser Phe Phe Leu Tyr Ser Lys Leu Thr Val
          180                 185                 190

Asp Lys Ser Arg Trp Gln Gln Gly Asn Val Phe Ser Cys Ser Val Met
      195                 200                 205

His Glu Ala Leu His Asn His Tyr Thr Gln Lys Ser Leu Ser Leu Ser
  210                 215                 220

Pro Gly Lys
225

<210> SEQ ID NO 47
<211> LENGTH: 720
<212> TYPE: PRT
<213> ORGANISM: Artificial Sequence
<220> FEATURE:
<223> OTHER INFORMATION: synthetic construct

<400> SEQUENCE: 47

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

-continued

Val Val Val Asp Val Ser His Glu Asp Pro Glu Val Lys Phe Asn Trp
            290             295             300

Tyr Val Asp Gly Val Glu Val His Asn Ala Lys Thr Lys Pro Arg Glu
305             310             315             320

Glu Gln Tyr Asn Ser Thr Tyr Arg Val Val Ser Val Leu Thr Val Leu
                325             330             335

His Gln Asp Trp Leu Asn Gly Lys Glu Tyr Lys Cys Lys Val Ser Asn
            340             345             350

Lys Ala Leu Pro Ala Pro Ile Glu Lys Thr Ile Ser Lys Ala Lys Gly
            355             360             365

Gln Pro Arg Glu Pro Gln Val Tyr Thr Leu Pro Pro Ser Arg Asp Glu
370             375             380

Leu Thr Lys Asn Gln Val Ser Leu Thr Cys Leu Val Lys Gly Phe Tyr
385             390             395             400

Pro Ser Asp Ile Ala Val Glu Trp Glu Ser Asn Gly Gln Pro Glu Asn
                405             410             415

Asn Tyr Lys Thr Thr Pro Pro Val Leu Lys Ser Asp Gly Ser Phe Phe
            420             425             430

Leu Tyr Ser Asp Leu Thr Val Asp Lys Ser Arg Trp Gln Gln Gly Asn
            435             440             445

Val Phe Ser Cys Ser Val Met His Glu Ala Leu His Asn His Tyr Thr
450             455             460

Gln Lys Ser Leu Ser Leu Ser Pro Gly Lys Gly Gly Gly Gly Gly Gly
465             470             475             480

Gly Gly Gly Gly Gly Gly Gly Gly Gly Gly Gly Gly Gly Asp Lys
                485             490             495

Thr His Thr Cys Pro Pro Cys Pro Ala Pro Glu Leu Leu Gly Gly Pro
            500             505             510

Ser Val Phe Leu Phe Pro Pro Lys Pro Lys Asp Thr Leu Met Ile Ser
            515             520             525

Arg Thr Pro Glu Val Thr Cys Val Val Val Asp Val Ser His Glu Asp
530             535             540

Pro Glu Val Lys Phe Asn Trp Tyr Val Asp Gly Val Glu Val His Asn
545             550             555             560

Ala Lys Thr Lys Pro Arg Glu Glu Gln Tyr Asn Ser Thr Tyr Arg Val
                565             570             575

Val Ser Val Leu Thr Val Leu His Gln Asp Trp Leu Asn Gly Lys Glu
            580             585             590

Tyr Lys Cys Lys Val Ser Asn Lys Ala Leu Pro Ala Pro Ile Glu Lys
            595             600             605

Thr Ile Ser Lys Ala Lys Gly Gln Pro Arg Glu Pro Gln Val Tyr Thr
            610             615             620

Leu Pro Pro Cys Arg Asp Lys Leu Thr Lys Asn Gln Val Ser Leu Trp
625             630             635             640

Cys Leu Val Lys Gly Phe Tyr Pro Ser Asp Ile Ala Val Glu Trp Glu
                645             650             655

Ser Asn Gly Gln Pro Glu Asn Asn Tyr Lys Thr Thr Pro Pro Val Leu
            660             665             670

Asp Ser Asp Gly Ser Phe Phe Leu Tyr Ser Lys Leu Thr Val Asp Lys
            675             680             685

Ser Arg Trp Gln Gln Gly Asn Val Phe Ser Cys Ser Val Met His Glu
690             695             700

Ala Leu His Asn His Tyr Thr Gln Lys Ser Leu Ser Leu Ser Pro Gly

<210> SEQ ID NO 48
<211> LENGTH: 720
<212> TYPE: PRT
<213> ORGANISM: Artificial Sequence
<220> FEATURE:
<223> OTHER INFORMATION: synthetic construct

<400> SEQUENCE: 48

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly

```
            355                 360                 365
Gln Pro Arg Glu Pro Gln Val Tyr Thr Leu Pro Pro Cys Arg Asp Lys
370                 375                 380

Leu Thr Lys Asn Gln Val Ser Leu Trp Cys Leu Val Lys Gly Phe Tyr
385                 390                 395                 400

Pro Ser Asp Ile Ala Val Glu Trp Glu Ser Asn Gly Gln Pro Glu Asn
                    405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys Gly Gly Gly Gly Gly Gly
465                 470                 475                 480

Gly Gly Gly Gly Gly Gly Gly Gly Gly Gly Gly Gly Asp Lys
                    485                 490                 495

Thr His Thr Cys Pro Pro Cys Pro Ala Pro Glu Leu Leu Gly Gly Pro
                500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
        530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                    565                 570                 575

Val Ser Val Leu Thr Val Leu His Gln Asp Trp Leu Asn Gly Lys Glu
                580                 585                 590

Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
        610                 615                 620

Leu Pro Pro Ser Arg Asp Glu Leu Thr Lys Asn Gln Val Ser Leu Thr
625                 630                 635                 640

Cys Leu Val Lys Gly Phe Tyr Pro Ser Asp Ile Ala Val Glu Trp Glu
                    645                 650                 655

Ser Asn Gly Gln Pro Glu Asn Asn Tyr Lys Thr Thr Pro Pro Val Leu
                660                 665                 670

Lys Ser Asp Gly Ser Phe Phe Leu Tyr Ser Asp Leu Thr Val Asp Lys
            675                 680                 685

Ser Arg Trp Gln Gln Gly Asn Val Phe Ser Cys Ser Val Met His Glu
        690                 695                 700

Ala Leu His Asn His Tyr Thr Gln Lys Ser Leu Ser Leu Ser Pro Gly
705                 710                 715                 720

<210> SEQ ID NO 49
<211> LENGTH: 720
<212> TYPE: PRT
<213> ORGANISM: Artificial Sequence
<220> FEATURE:
<223> OTHER INFORMATION: synthetic construct

<400> SEQUENCE: 49

Asp Lys Thr His Thr Cys Pro Pro Cys Pro Ala Pro Glu Leu Leu Gly
```

-continued

```
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
                35                  40                  45
Glu Asp Pro Glu Val Lys Phe Asn Trp Tyr Val Asp Gly Val Glu Val
     50                  55                  60
His Asn Ala Lys Thr Lys Pro Arg Glu Gln Tyr Asn Ser Thr Tyr
 65                  70                  75                  80
Arg Val Val Ser Val Leu Thr Val Leu His Gln Asp Trp Leu Asn Gly
                85                  90                  95
Lys Glu Tyr Lys Cys Lys Val Ser Asn Lys Ala Leu Pro Ala Pro Ile
                100                 105                 110
Glu Lys Thr Ile Ser Lys Ala Lys Gly Gln Pro Arg Glu Pro Gln Val
                115                 120                 125
Tyr Thr Leu Pro Pro Ser Arg Asp Glu Leu Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Lys Ser Asp Gly Ser Phe Phe Leu Tyr Ser Lys Leu Thr Val
                180                 185                 190
Asp Lys Ser Arg Trp Gln Gln Gly Asn Val Phe Ser Cys Ser Val Met
                195                 200                 205
His Glu Ala Leu His Asn His Tyr Thr Gln Lys Ser Leu Ser Leu Ser
     210                 215                 220
Pro Gly Lys Gly Gly Gly Gly Gly Gly Gly Gly Gly Gly Gly Gly Gly
225                 230                 235                 240
Gly Gly Gly Gly Gly Gly Asp Lys Thr His Thr Cys Pro Pro Cys
            245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
            275                 280                 285
Val Val Val Asp Val Ser His Glu Asp Pro Glu Val Lys Phe Asn Trp
            290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
                340                 345                 350
Lys Ala Leu Pro Ala Pro Ile Glu Lys Thr Ile Ser Lys Ala Lys Gly
                355                 360                 365
Gln Pro Arg Glu Pro Gln Val Tyr Thr Leu Pro Pro Cys Arg Asp Lys
            370                 375                 380
Leu Thr Lys Asn Gln Val Ser Leu Trp Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
                420                 425                 430
```

```
Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
        450                 455                 460

Gln Lys Ser Leu Ser Leu Ser Pro Gly Lys Gly Gly Gly Gly Gly Gly
465                 470                 475                 480

Gly Gly Gly Gly Gly Gly Gly Gly Gly Gly Gly Gly Gly Gly Asp Lys
                485                 490                 495

Thr His Thr Cys Pro Pro Cys Pro Ala Pro Glu Leu Leu Gly Gly Pro
                500                 505                 510

Ser Val Phe Leu Phe Pro Pro Lys Pro Lys Asp Thr Leu Met Ile Ser
            515                 520                 525

Arg Thr Pro Glu Val Thr Cys Val Val Val Asp Val Ser His Glu Asp
530                 535                 540

Pro Glu Val Lys Phe Asn Trp Tyr Val Asp Gly Val Glu Val His Asn
545                 550                 555                 560

Ala Lys Thr Lys Pro Arg Glu Glu Gln Tyr Asn Ser Thr Tyr Arg Val
                565                 570                 575

Val Ser Val Leu Thr Val Leu His Gln Asp Trp Leu Asn Gly Lys Glu
            580                 585                 590

Tyr Lys Cys Lys Val Ser Asn Lys Ala Leu Pro Ala Pro Ile Glu Lys
            595                 600                 605

Thr Ile Ser Lys Ala Lys Gly Gln Pro Arg Glu Pro Gln Val Tyr Thr
            610                 615                 620

Leu Pro Pro Cys Arg Asp Lys Leu Thr Lys Asn Gln Val Ser Leu Trp
625                 630                 635                 640

Cys Leu Val Lys Gly Phe Tyr Pro Ser Asp Ile Ala Val Glu Trp Glu
                645                 650                 655

Ser Asn Gly Gln Pro Glu Asn Asn Tyr Lys Thr Thr Pro Pro Val Leu
            660                 665                 670

Asp Ser Asp Gly Ser Phe Phe Leu Tyr Ser Lys Leu Thr Val Asp Lys
            675                 680                 685

Ser Arg Trp Gln Gln Gly Asn Val Phe Ser Cys Ser Val Met His Glu
            690                 695                 700

Ala Leu His Asn His Tyr Thr Gln Lys Ser Leu Ser Leu Ser Pro Gly
705                 710                 715                 720
```

What is claimed is:

1. A method of inducing immune cell activation in a subject, the method comprising administering to the subject a composition comprising an Fc construct comprising:
   a) a first polypeptide having the formula A-L1-B-L2-C; wherein
      i) A comprises a first Fc domain monomer;
      ii) L1 is a linker;
      iii) B comprises a second Fc domain monomer;
      iv) L2 is a linker; and
      v) C comprises a third Fc domain monomer;
   b) a second polypeptide having the formula A'-L1'-B'-L2'-C'; wherein
      i) A' comprises a fourth Fc domain monomer;
      ii) L1' is a linker;
      iii) B' comprises a fifth Fc domain monomer;
      iv) L2' is a linker; and
      v) C' comprises a sixth Fc domain monomer;
   c) a third polypeptide that comprises a seventh Fc domain monomer;
   d) a fourth polypeptide that comprises an eighth Fc domain monomer;
   e) a fifth polypeptide that comprises a ninth Fc domain monomer; and
   f) a sixth polypeptide that comprises a tenth Fc domain monomer;
   wherein A and the seventh Fc domain monomer combine to form a first Fc domain, B and B' combine to form a second Fc domain, C and the eighth Fc domain monomer combine to form a third Fc domain, A' and the ninth Fc domain monomer combine to form a fourth Fc domain, and C' and the tenth Fc domain monomer combine to form a fifth Fc domain;
   wherein each of the first and seventh Fc domain monomers comprises a complementary dimerization selectivity module that promote dimerization between the first Fc domain monomer and the seventh Fc domain monomer,
   each of the second and fifth Fc domain monomers comprises a complementary dimerization selectivity module that promote dimerization between the second Fc domain monomer and the fifth Fc domain monomer, each of the third and eighth Fc domain monomers comprises a complementary dimerization selectivity module that promote dimerization between the third Fc domain monomer and the eighth Fc domain monomer;

each of the fourth and ninth Fc domain monomers comprises a complementary dimerization selectivity module that promote dimerization between the fourth Fc domain monomer and the ninth Fc domain monomer; and each of the sixth and tenth Fc domain monomers comprises a complementary dimerization selectivity module that promote dimerization between the sixth Fc domain monomer and the tenth Fc domain monomer; and g) each of the first and second polypeptides comprise the sequence:

(SEQ ID NO: 47)
DKTHTCPPCPAPELLGGPSVFLEPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDKLTKNQVSLWCLVK

GFYPSDIAVEWESNGQPENNYKTTPPVLDSDGSFFLYSKLTVDKSRWQQG

NVFSCSVMHEALHNHYTQKSLSLSPGKGGGGGGGGGGGGGGGGGGDKT

HTCPPCPAPELLGGPSVFLEPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPSRDELTKNQVSLTCLVKGFY

PSDIAVEWESNGQPENNYKTTPPVLKSDGSFFLYSDLTVDKSRWQQGNVF

SCSVMHEALHNHYTQKSLSLSPGKGGGGGGGGGGGGGGGGGGGDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPCRDKLTKNQVSLWCLVKGEYPSD

IAVEWESNGQPENNYKTTPPVLDSDGSFFLYSKLTVDKSRWQQGNVFSCS

VMHEALHNHYTQKSLSLSPG;

and each of the third, fourth, fifth, and sixth polypeptides comprise the sequence:

(SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG.

2. A method of inducing immune cell activation in a subject, the method comprising administering to the subject a composition comprising an Fc construct comprising:

a) a first polypeptide having the formula A-L1-B-L2-C; wherein
i) A comprises a first Fc domain monomer;
ii) L1 is a linker;
iii) B comprises a second Fc domain monomer;
iv) L2 is a linker; and
v) C comprises a third Fc domain monomer;

b) a second polypeptide having the formula A'-L1'-B'-L2'-C'; wherein
i) A' comprises a fourth Fc domain monomer;
ii) L1' is a linker;
iii) B' comprises a fifth Fc domain monomer;
iv) L2' is a linker; and
v) C' comprises a sixth Fc domain monomer;

c) a third polypeptide that comprises a seventh Fc domain monomer;

d) a fourth polypeptide that comprises an eighth Fc domain monomer;

e) a fifth polypeptide that comprises a ninth Fc domain monomer; and f) a sixth polypeptide that comprises a tenth Fc domain monomer;

wherein C and C' combine to form a first Fc domain, B and the seventh Fc domain monomer combine to form a second Fc domain, A and the eighth Fc domain monomer combine to form a third Fc domain, B' and the ninth Fc domain monomer combine to form a fourth Fc domain, and A' and the tenth Fc domain monomer combine to form a fifth Fc domain;

wherein each of the third and sixth Fc domain monomers comprises complementary dimerization selectivity modules that promote dimerization between the third Fc domain monomer and the sixth Fc domain monomer, each of the second and seventh Fc domain monomers comprises complementary dimerization selectivity modules that promote dimerization between the second Fc domain monomer and the seventh Fc domain monomer, each of the first and eighth Fc domain monomers comprises complementary dimerization selectivity modules that promote dimerization between the first Fc domain monomer and the eighth Fc domain monomer;

each of the fifth and ninth Fc domain monomers comprises complementary dimerization selectivity modules that promote dimerization between the fifth Fc domain monomer and the ninth Fc domain monomer; and each of the fourth and tenth Fc domain monomers comprises complementary dimerization selectivity modules that promote dimerization between the fourth Fc domain monomer and the tenth Fc domain monomer; and (g) the first and second polypeptides comprise the sequence:

(SEQ ID NO: 48)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPCRDKLTKNQVSLWCLVK

GFYPSDIAVEWESNGQPENNYKTTPPVLDSDGSFFLYSKLTVDKSRWQQG

NVFSCSVMHEALHNHYTQKSLSLSPGKGGGGGGGGGGGGGGGGGGDKT

HTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPCRDKLTKNQVSLWCLVKGFY

PSDIAVEWESNGQPENNYKTTPPVLDSDGSFFLYSKLTVDKSRWQQGNVF

SCSVMHEALHNHYTQKSLSLSPGKGGGGGGGGGGGGGGGGGGGDKTHTC

-continued

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLKSDGSFFLYSDLTVDKSRWQQGNVFSCS

VMHEALHNHYTQKSLSLSPG;

and the third, fourth, fifth, and sixth polypeptides comprise the sequence:

(SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG.

3. A method of inducing immune cell activation in a subject, the method comprising administering to the subject a composition comprising an Fc construct comprising:
  a) a first polypeptide having the formula A-L1-B-L2-C; wherein
    i) A comprises a first Fc domain monomer;
    ii) L1 is a linker;
    iii) B comprises a second Fc domain monomer;
    iv) L2 is a linker; and
    v) C comprises a third Fc domain monomer;
  b) a second polypeptide having the formula A'-L1'-B'-L2'-C'; wherein
    i) A' comprises a fourth Fc domain monomer;
    ii) L1' is a linker;
    iii) B' comprises a fifth Fc domain monomer;
    iv) L2' is a linker; and
    v) C' comprises a sixth Fc domain monomer;
  c) a third polypeptide that comprises a seventh Fc domain monomer;
  d) a fourth polypeptide that comprises an eighth Fc domain monomer;
  e) a fifth polypeptide that comprises a ninth Fc domain monomer; and
  f) a sixth polypeptide that comprises a tenth Fc domain monomer;
  wherein A and A' combine to form a first Fc domain, B and the seventh Fc domain monomer combine to form a second Fc domain, C and the eighth Fc domain monomer combine to form a third Fc domain, B' and the ninth Fc domain monomer combine to form a fourth Fc domain, and C' and the tenth Fc domain monomer combine to form a fifth Fc domain;
  wherein each of the first and fourth Fc domain monomers comprises complementary dimerization selectivity modules that promote dimerization between the first Fc domain monomer and the fourth Fc domain monomer,
  each of the second and seventh Fc domain monomers comprises complementary dimerization selectivity modules that promote dimerization between the second Fc domain monomer and the seventh Fc domain monomer,
  each of the third and eighth Fc domain monomers comprises complementary dimerization selectivity modules that promote dimerization between the third Fc domain monomer and the eighth Fc domain monomer;
  each of the fifth and ninth Fc domain monomers comprises complementary dimerization selectivity modules that promote dimerization between the fifth Fc domain monomer and the ninth Fc domain monomer; and
  each of the sixth and tenth Fc domain monomers comprises complementary dimerization selectivity modules that promote dimerization between the sixth Fc domain monomer and the tenth Fc domain monomer; and
  (g) the first and second polypeptides comprises the sequence:

(SEQ ID NO: 49)
DKTHTCPPCPAPELLGGPSVFLEPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLKSDGSFFLYSDLTVDKSRWQQG

NVFSCSVMHEALHNHYTQKSLSLSPGKGGGGGGGGGGGGGGGGGGGGDKT

HTCPPCPAPELLGGPSVFLEPPKPKDTLMISRTPEVTCVVVDVSHEDPEV

KFNWYVDGVEVHNAKTKPREEQYNSTYRVVSVLTVLHQDWLNGKEYKCKV

SNKALPAPIEKTISKAKGQPREPQVYTLPPCRDKLTKNQVSLWCLVKGFY

PSDIAVEWESNGQPENNYKTTPPVLDSDGSFFLYSKLTVDKSRWQQGNVF

SCSVMHEALHNHYTQKSLSLSPGKGGGGGGGGGGGGGGGGGGGGDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPCRDKLTKNQVSLWCLVKGFYPSD

IAVEWESNGQPENNYKTTPPVLDSDGSFFLYSKLTVDKSRWQQGNVFSCS

VMHEALHNHYTQKSLSLSPG;

and the third, fourth, fifth, and sixth polypeptides comprises sequence:

(SEQ ID NO: 42)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVCTLPPSRDELTKNQVSLSCAVD

GFYPSDIAVEWESNGQPENNYKTTPPVLDSDGSFFLVSKLTVDKSRWQQG

NVFSCSVMHEALHNHYTQKSLSLSPG.

* * * * *